United States Patent [19]
Morrow et al.

[11] Patent Number: 5,817,512
[45] Date of Patent: Oct. 6, 1998

[54] ENCAPSIDATED RECOMBINANT VIRAL NUCLEIC ACID AND METHODS OF MAKING AND USING SAME

[75] Inventors: Casey D. Morrow; Donna C. Porter, both of Birmingham; David C. Ansardi, Warrior, all of Ala.

[73] Assignee: The UAB Research Foundation, Birmingham, Ala.

[21] Appl. No.: 389,459

[22] Filed: Feb. 15, 1995

Related U.S. Application Data

[63] Continuation-in-part of Ser. No. 87,009, Jul. 1, 1993, abandoned.

[51] Int. Cl.$^6$ ............................. C12N 15/43; C12P 21/02; A61K 39/13
[52] U.S. Cl. ..................... 435/320.1; 435/93; 435/172.3; 424/199.1; 424/217.1
[58] Field of Search ................................ 435/69.1, 172.1, 435/320.1; 424/199.1, 93.21, 217.1

[56] References Cited

PUBLICATIONS

Kantor et al. Antitumor activity and immune responses inducted by a recombinant carcinoembryonic antigen–vaccinia virus vaccine J. Natl. Cancer Institute vol. 84 1084–1091, 1992.

Knuth et al. Cellular and humoral immune responses against cancer: implications for cancer vaccines Current Opinion in Immunol. vol. 3 659–664 1991.

Fox No winners against AIDS Biotechnology vol. 12 128, 1994.

Choi et al. Expression of human immunodeficiency virus type 1 (HIV–1) gag, pol, and env proteins from chimeric HIV–1–poliovirus minireplicons J. Virol. vol. 65 2875–2883, 1991.

Ansardi, D.C. et al. (1994) "Characterization Poliovirus Repilicons Encoding Carcinoembryonic Antigen" *Cancer Research* 54:6359–6364.

Ansardi, D.C. et al. (1991) "Coinfection with Recombinant Vaccinia Viruses Expressing Poliovirus P1 and P3 Proteins Results in Polyprotein Processing and Formation of Empty Capsid Structures" *J. Virol.* 65(4):2088–2092.

Ansardi, D.C. et al. (1993) "Complementation of a Poliovirus Defective Genome by a Recombinant Vaccinia Virus Which Provides Poliovirus P1 Capsid Precursor in trans" *J. Virol.* 67(6):3684–3690.

Ansardi, D.C. et al. (1992) "Myristylation of Polivirus Capsid Precursor P1 Is Required for Assembly of Subviral Particles" *J. Virol.* 66(7):4556–4563;.

Choi, W.S. et al. (1991) "Expression of Human Immunodeficieny Virus Type 1 (HIV–1) gag, pol, and env Proteins from Chimeric HIV–1–Poliovirus Minireplicons"*J. Virol* 65(6):2875–2883.

Evans, D.J. et al. (1989) "An Engineered Poliovirus Chimaera Elicits Boradly Reactive HIV–1 Neutralizing Antibodies" *Nature* 339:385–388;.

Haynes, B.F. (1993) "Scientific and Social Issues of Human Immunodeficiency Virus Vaccine Development" *Science* 260: 1279–1286.

Jenkins, O. et al. (1990) "An Anitgen Chimera of Polivirus Induces Antibodies against Human Papillomavirus Type 16" *J. Virol.* 64(3):1201–1206.

McGhee, J.R. and Mestecky, J. (1992) "The Mucosal Immune System in HIV Infection and Prospects for Mucosal Immunity to AIDS" in *AIDS Research Reviews*, W.C. Koff et al. (eds.), New York: Marcel Dekker, Inc., 2:Ch. 15, 289–312.

Moldoveanu, Z. et al. (1995) "Immune Response s Induced by Administration of Encapsidated Poliovirus Replicons Which Express HIV–1 gag and env Proteins" *FASEB J.* 9(3):A214, No. 1247.

Morrow, C.D. et al. (1994) "New Approaches for Mucosal Vaccines for AIDS: Encapisadation and Serial Passage of Poliovirus Repilicons that Express HIV–1 Proteins on Infection" *AIDS Research and Human Retroviruses* 10 Suppl. 1:S61–S66.

Percy, N. et al. (1992) "A Poliovirus Replicon Containing the Chloramphenicol Acetytranferase Gene Can Be Used To Study the Replicon and Encapsidation of Poliovirus RNA" *J. Virol.* 66(8):5040–5046.

(List continued on next page.)

*Primary Examiner*—James Ketter
*Assistant Examiner*—John S. Brusca
*Attorney, Agent, or Firm*—Jean M. Silveri; Lahive & Cockfield, LLP

[57] ABSTRACT

The present invention pertains to a method of encapsidating a recombinant poliovirus nucleic acid to obtain a yield of encapsidated viruses which substantially comprises encapsidated recombinant poliovirus nucleic acid. The method of encapsidating a recombinant poliovirus nucleic acid includes contacting a host cell with a recombinant poliovirus nucleic acid which lacks the nucleotide sequence encoding at least a portion of a protein necessary for encapsidation and an expression vector comprising a nucleic acid which encodes at least a portion of one protein necessary for encapsidation under conditions appropriate for introduction of the recombinant poliovirus nucleic acid and the expression vector into the host cell and obtaining a yield of encapsidated viruses which substantially comprises an encapsidated recombinant poliovirus nucleic acid. A foreign nucleotide sequence is generally substituted for the nucleotide sequence of the poliovirus nucleic acid encoding at least a portion of a protein necessary for encapsidation. The invention further pertains to encapsidated recombinant poliovirus nucleic acids produced by the method of this invention and compositions containing the encapsidated or nonencapsidated recombinant poliovirus nucleic acid containing a foreign nucleotide sequence for use in a method of stimulating an immune response in a subject to the protein encoded by the foreign nucleotide sequence.

37 Claims, 21 Drawing Sheets

OTHER PUBLICATIONS

Porter, D.C. et al. (1993) "Encapsidation of Genetically Engineered Poliovirus Minireplicons Which Express Human Immunodeficiency Virus Type 1 Gag and Pol Proteins upon Infection" *J. Virol.* 67(7):3712–3719.

Porter, D.C. et al. (1993) "Expression of Poliovirus P3 Proteins Using a Recombinant Vaccinia Virus Results in Proteolytically Active 3CD Precursor Protein Without Further Processing to $3C^{pro}$ and $3D^{pol}$" *Virus Research* 29:241–254.

Porter, D.C. et al. (Mar. 13–18, 1993) "Encapsidation of Chimeric HIV–1–Poliovirus Minireplicons"*J. Cell Biochem. Suppl.* 17 (D): p. 26.

Ansardi, D.C. et al. (Mar. 13–18, 1993) "Molecular Analysis of Poliovirus Assembly Using Recombinant Vaccinia Viruses to Complement A Poliovirus Genome With A Capsid Gene Deletion" *J. Cell Biochem. Suppl.* 17 (D); p. 22.

Porter, D. et al., "Encapsidation of Poliovirus Replicons Encoding the Complete Human Immunodeficiency Virus Type 1 gag Gene by Using a Complementation System Which Provides the P1 Capsid Protein in trans," *Journal of Virology*, vol. 69, No. 3, 1548–1555 (Mar. 1995).

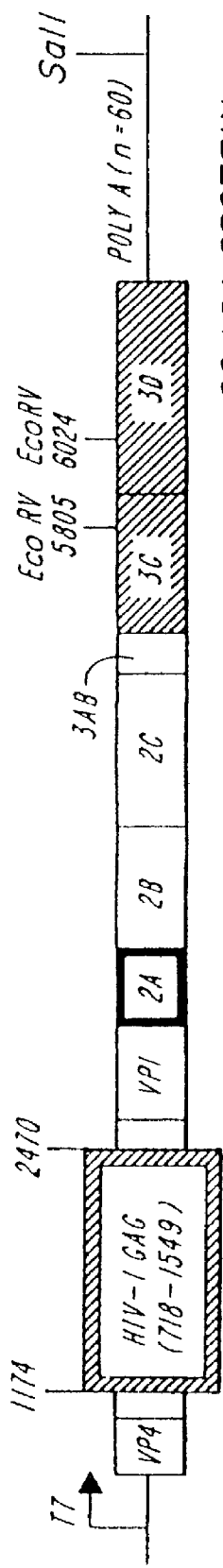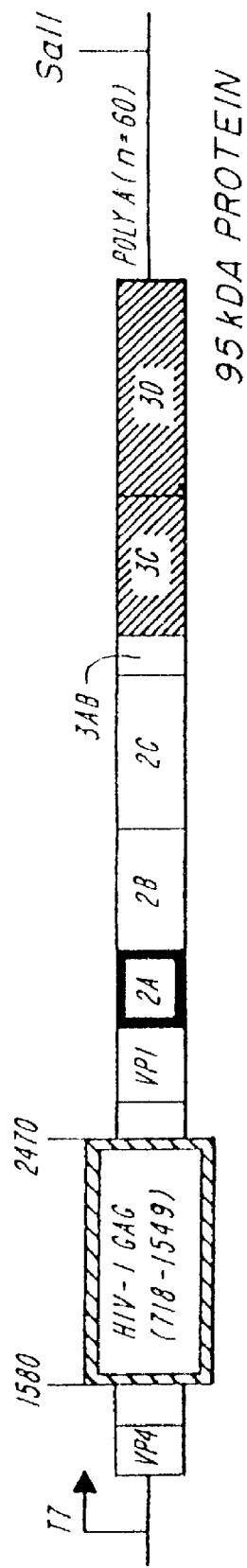

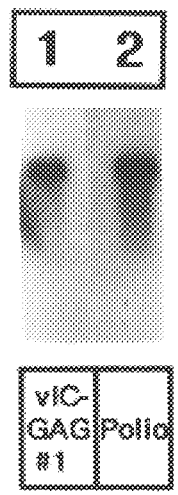
FIG.5
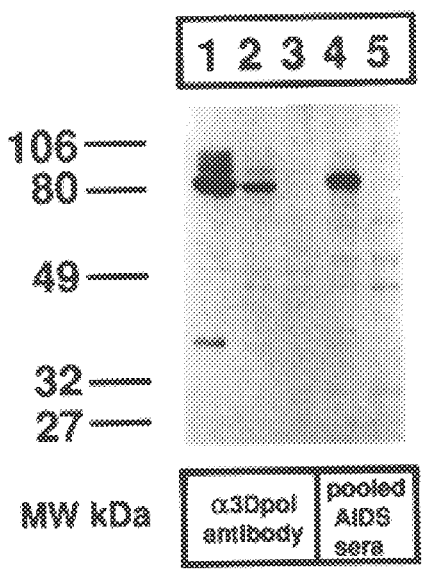
FIG.6
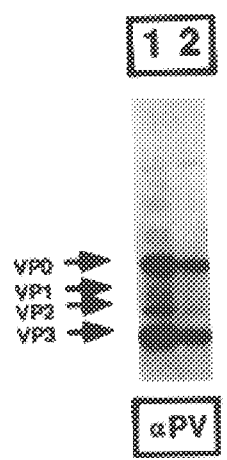
FIG.7A
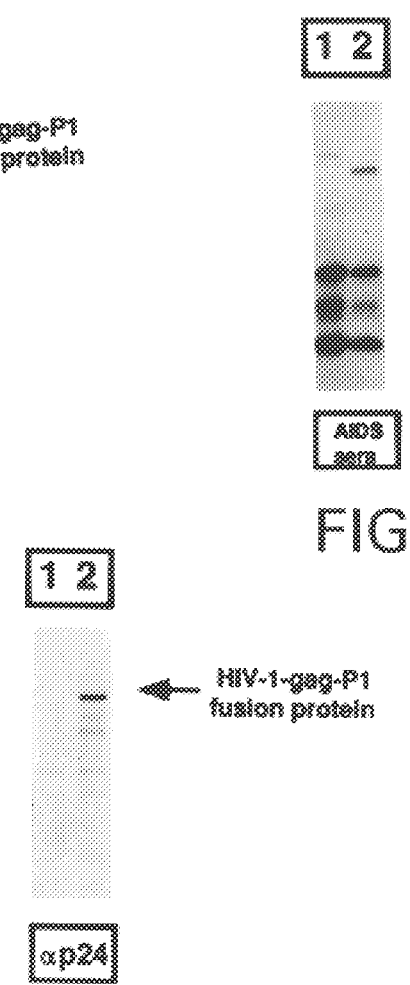
FIG.7B
FIG.7C

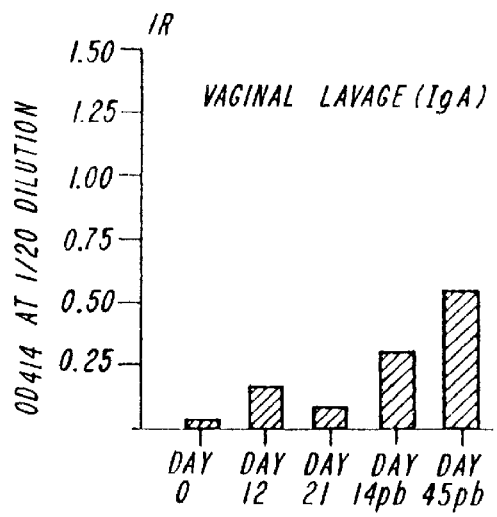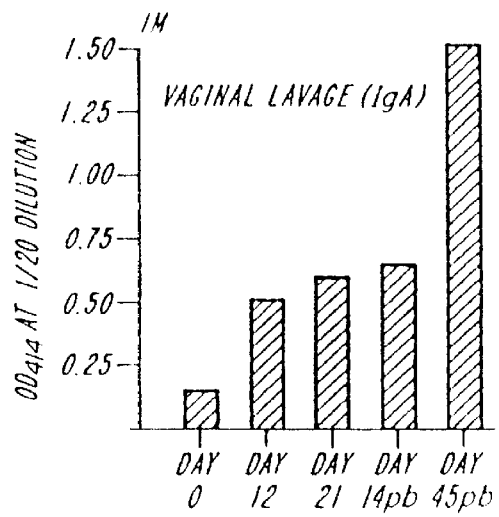
FIG. 14A  FIG. 14B
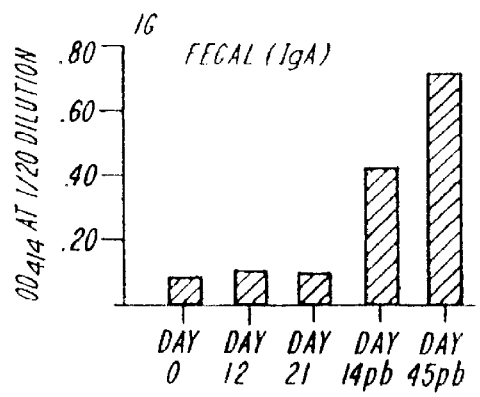
FIG. 15A
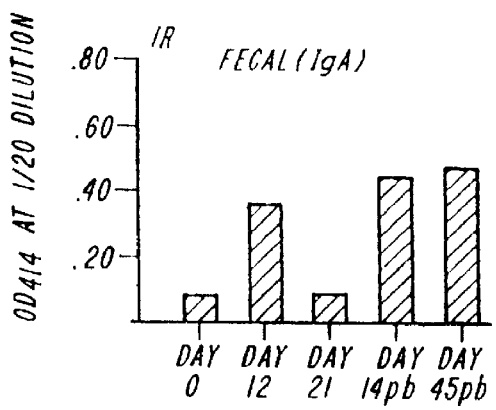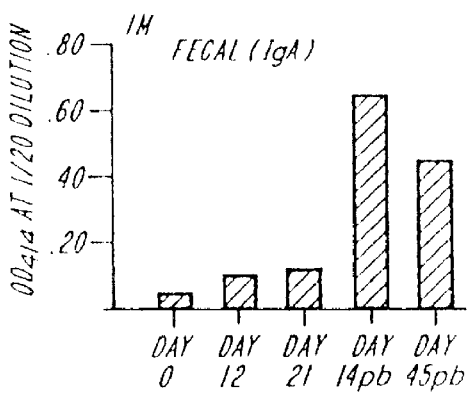
FIG. 15B  FIG. 15C pT7-IC:

pT7-IC-Pr55 gag:

pT7-IC-Pr55 gag (VP4/2A):

Phosphorimagery Quantitation of Samples
Analyzed by Northern Blot

| Samples | Values |
|---|---|
| pT7-IC-Pr55$^{gag}$ | 19,062 |
| pT7-IC-Pr55$^{gag}$ (VP4/2A) | 18,430 |
| pT7-IC-Gag 1 | 98,800 |

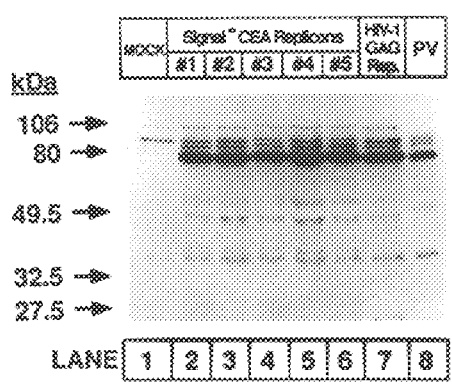
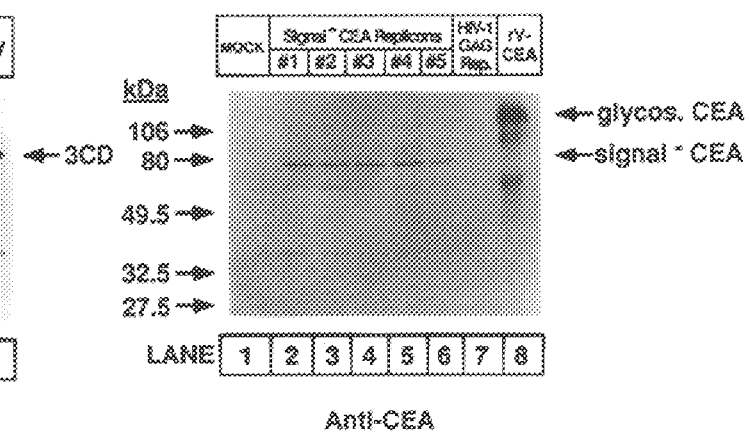
*FIG. 24A*  *FIG. 24B*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
TATTAGTAGA TCTG                                              14
```

( 2 ) INFORMATION FOR SEQ ID NO:2:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
TACAGATGTA CTAA                                              14
```

( 2 ) INFORMATION FOR SEQ ID NO:3:

( i ) SEQUENCE CHARACTERISTICS:
( A ) LENGTH: 845 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 20..845

( x i ) SEQUENCE DESCRIPTION: SEQ ID NO:3:

```
ACACAGCAAT CAGGTCAGC CAA AAT TAC CCT ATA GTG CAG AAC ATC CAG GGG      52
                     Gln Asn Tyr Pro Ile Val Gln Asn Ile Gln Gly
                      1               5                  10

CAA ATG GTA CAT CAG GCC ATA TCA CCT AGA ACT TTA AAT GCA TGG GTA      100
Gln Met Val His Gln Ala Ile Ser Pro Arg Thr Leu Asn Ala Trp Val
            15                  20                  25

AAA GTA GTA GAA GAG AAG GCT TTC AGC CCA GAA GTG ATA CCC ATG TTT      148
Lys Val Val Glu Glu Lys Ala Phe Ser Pro Glu Val Ile Pro Met Phe
```

```
TCA GCA TTA TCA GAA GGA GCC ACC CCA CAA GAT TTA AAC ACC ATG CTA     196
Ser Ala Leu Ser Glu Gly Ala Thr Pro Gln Asp Leu Asn Thr Met Leu
    45              50                      55

AAC ACA GTG GGG GGA CAT CAA GCA GCC ATG CAA ATG TTA AAA GAG ACC     244
Asn Thr Val Gly Gly His Gln Ala Ala Met Gln Met Leu Lys Glu Thr
60              65                      70                      75

ATC AAT GAG GAA GCT GCA GAA TGG GAT AGA GTG CAT CCA GTG CAT GCA     292
Ile Asn Glu Glu Ala Ala Glu Trp Asp Arg Val His Pro Val His Ala
                    80                      85                  90

GGG CCT ATT GCA CCA GGC CAG ATG AGA GAA CCA AGG GGA AGT GAC ATA     340
Gly Pro Ile Ala Pro Gly Gln Met Arg Glu Pro Arg Gly Ser Asp Ile
            95                      100                     105

GCA GGA ACT ACT AGT ACC CTT CAG GAA CAA ATA GGA TGG ATG ACA AAT     388
Ala Gly Thr Thr Ser Thr Leu Gln Glu Gln Ile Gly Trp Met Thr Asn
        110                     115                     120

AAT CCA CCT ATC CCA GTA GGA GAA ATT TAT AAA AGA TGG ATA ATC CTG     436
Asn Pro Pro Ile Pro Val Gly Glu Ile Tyr Lys Arg Trp Ile Ile Leu
    125                     130                     135

GGA TTA AAT AAA ATA GTA AGA ATG TAT AGC CCT ACC AGC ATT CTG GAC     484
Gly Leu Asn Lys Ile Val Arg Met Tyr Ser Pro Thr Ser Ile Leu Asp
140                     145                     150                 155

ATA AGA CAA GGA CCA AAG GAA CCC TTT AGA GAC TAT GTA GAC CGG TTC     532
Ile Arg Gln Gly Pro Lys Glu Pro Phe Arg Asp Tyr Val Asp Arg Phe
                        160                     165             170

TAT AAA ACT CTA AGA GCC GAG CAA GCT TCA CAG GAG GTA AAA AAT TGG     580
Tyr Lys Thr Leu Arg Ala Glu Gln Ala Ser Gln Glu Val Lys Asn Trp
                175                     180                     185

ATG ACA GAA ACC TTG TTG GTC CAA AAT GCG AAC CCA GAT TGT AAG ACT     628
Met Thr Glu Thr Leu Leu Val Gln Asn Ala Asn Pro Asp Cys Lys Thr
            190                     195                     200

ATT TTA AAA GCA TTG GGA CCA GCG GCT ACA CTA GAA GAA ATG ATG ACA     676
Ile Leu Lys Ala Leu Gly Pro Ala Ala Thr Leu Glu Glu Met Met Thr
        205                     210                     215

GCA TGT CAG GGA GTA GGA GGA CCC GGC CAT AAG GCA AGA GTT TTG GCT     724
Ala Cys Gln Gly Val Gly Gly Pro Gly His Lys Ala Arg Val Leu Ala
220                     225                     230                 235

GAA GCA ATG AGC CAA GTA ACA AAT TCA GCT ACC ATA ATG ATG CAG AGA     772
Glu Ala Met Ser Gln Val Thr Asn Ser Ala Thr Ile Met Met Gln Arg
                        240                     245             250

GGC AAT TTT AGG AAC CAA AGA AAG ATT GTT AAG TGT TTC AAT TGT GGC     820
Gly Asn Phe Arg Asn Gln Arg Lys Ile Val Lys Cys Phe Asn Cys Gly
                255                     260                     265

AAA GAA GGG CAC ACA GCC AGA AAG T                                   845
Lys Glu Gly His Thr Ala Arg Lys
            270                     275
```

(2) INFORMATION FOR SEQ ID NO:4:

(i) SEQUENCE CHARACTERISTICS:
       (A) LENGTH: 275 amino acids
       (B) TYPE: amino acid
       (D) TOPOLOGY: linear (ii) MOLECULE TYPE: protein (xi) SEQUENCE DESCRIPTION: SEQ ID NO:4:

```
Gln Asn Tyr Pro Ile Val Gln Asn Ile Gln Gly Gln Met Val His Gln
 1               5                   10                      15

Ala Ile Ser Pro Arg Thr Leu Asn Ala Trp Val Lys Val Val Glu Glu
            20                      25                      30
```

| | | | | | | | | | | | | | | |
|---|---|---|---|---|---|---|---|---|---|---|---|---|---|---|
| Lys | Ala | Phe | Ser | Pro | Glu | Val | Ile | Pro | Met | Phe | Ser | Ala | Leu | Ser | Glu |
| | | 35 | | | | 40 | | | | | 45 | | | | |
| Gly | Ala | Thr | Pro | Gln | Asp | Leu | Asn | Thr | Met | Leu | Asn | Thr | Val | Gly | Gly |
| | | 50 | | | | 55 | | | | | 60 | | | | |
| His | Gln | Ala | Ala | Met | Gln | Met | Leu | Lys | Glu | Thr | Ile | Asn | Glu | Glu | Ala |
| 65 | | | | | 70 | | | | | 75 | | | | | 80 |
| Ala | Glu | Trp | Asp | Arg | Val | His | Pro | Val | His | Ala | Gly | Pro | Ile | Ala | Pro |
| | | | | 85 | | | | | 90 | | | | | 95 | |
| Gly | Gln | Met | Arg | Glu | Pro | Arg | Gly | Ser | Asp | Ile | Ala | Gly | Thr | Thr | Ser |
| | | | 100 | | | | | 105 | | | | | 110 | | |
| Thr | Leu | Gln | Glu | Gln | Ile | Gly | Trp | Met | Thr | Asn | Asn | Pro | Pro | Ile | Pro |
| | | | 115 | | | | 120 | | | | | 125 | | | |
| Val | Gly | Glu | Ile | Tyr | Lys | Arg | Trp | Ile | Ile | Leu | Gly | Leu | Asn | Lys | Ile |
| | | 130 | | | | 135 | | | | | 140 | | | | |
| Val | Arg | Met | Tyr | Ser | Pro | Thr | Ser | Ile | Leu | Asp | Ile | Arg | Gln | Gly | Pro |
| 145 | | | | | 150 | | | | | 155 | | | | | 160 |
| Lys | Glu | Pro | Phe | Arg | Asp | Tyr | Val | Asp | Arg | Phe | Tyr | Lys | Thr | Leu | Arg |
| | | | | 165 | | | | | 170 | | | | | 175 | |
| Ala | Glu | Gln | Ala | Ser | Gln | Glu | Val | Lys | Asn | Trp | Met | Thr | Glu | Thr | Leu |
| | | | 180 | | | | | 185 | | | | | 190 | | |
| Leu | Val | Gln | Asn | Ala | Asn | Pro | Asp | Cys | Lys | Thr | Ile | Leu | Lys | Ala | Leu |
| | | | 195 | | | | | 200 | | | | | 205 | | |
| Gly | Pro | Ala | Ala | Thr | Leu | Glu | Glu | Met | Met | Thr | Ala | Cys | Gln | Gly | Val |
| | | 210 | | | | 215 | | | | | 220 | | | | |
| Gly | Gly | Pro | Gly | His | Lys | Ala | Arg | Val | Leu | Ala | Glu | Ala | Met | Ser | Gln |
| 225 | | | | | 230 | | | | | 235 | | | | | 240 |
| Val | Thr | Asn | Ser | Ala | Thr | Ile | Met | Met | Gln | Arg | Gly | Asn | Phe | Arg | Asn |
| | | | | 245 | | | | | 250 | | | | | 255 | |
| Gln | Arg | Lys | Ile | Val | Lys | Cys | Phe | Asn | Cys | Gly | Lys | Glu | Gly | His | Thr |
| | | | 260 | | | | | 265 | | | | | 270 | | |
| Ala | Arg | Lys |
| | | 275 |

( 2 ) INFORMATION FOR SEQ ID NO:5:

( i ) SEQUENCE CHARACTERISTICS:
        ( A ) LENGTH: 948 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 4..946

( x i ) SEQUENCE DESCRIPTION: SEQ ID NO:5:

| AAC | CAA | TGG | CCA | TTG | ACA | GAA | GAA | AAA | ATA | AAA | GCA | TTA | GTA | GAA | ATT | 48 |
|---|---|---|---|---|---|---|---|---|---|---|---|---|---|---|---|---|
| | Gln | Trp | Pro | Leu | Thr | Glu | Glu | Lys | Ile | Lys | Ala | Leu | Val | Glu | Ile | |
| | 1 | | | | 5 | | | | | 10 | | | | | 15 | |
| TGT | ACA | GAG | ATG | GAA | AAG | GAA | GGG | AAA | ATT | TCA | AAA | ATT | GGG | CCT | GAA | 96 |
| Cys | Thr | Glu | Met | Glu | Lys | Glu | Gly | Lys | Ile | Ser | Lys | Ile | Gly | Pro | Glu | |
| | | | | 20 | | | | | 25 | | | | | 30 | | |
| AAT | CCA | TAC | AAT | ACT | CCA | GTA | TTT | GCC | ATA | AAG | AAA | AAA | GAC | AGT | ACT | 144 |
| Asn | Pro | Tyr | Asn | Thr | Pro | Val | Phe | Ala | Ile | Lys | Lys | Lys | Asp | Ser | Thr | |
| | | | 35 | | | | | 40 | | | | | 45 | | | |
| AAA | TGG | AGA | AAA | TTA | GTA | GAT | TTC | AGA | GAA | CTT | AAT | AAG | AGA | ACT | CAA | 192 |
| Lys | Trp | Arg | Lys | Leu | Val | Asp | Phe | Arg | Glu | Leu | Asn | Lys | Arg | Thr | Gln | |
| | | 50 | | | | | 55 | | | | | 60 | | | | |

```
GAC  TTC  TGG  GAA  GTT  CAA  TTA  GGA  ATA  CCA  CAT  CCC  GCA  GGG  TTA  AAA       240
Asp  Phe  Trp  Glu  Val  Gln  Leu  Gly  Ile  Pro  His  Pro  Ala  Gly  Leu  Lys
      65                      70                  75

AAG  AAA  AAA  TCA  GTA  ACA  GTA  CTG  GAT  GTG  GGT  GAT  GCA  TAT  TTT  TCA       288
Lys  Lys  Lys  Ser  Val  Thr  Val  Leu  Asp  Val  Gly  Asp  Ala  Tyr  Phe  Ser
 80                     85                       90                            95

GTT  CCC  TTA  GAT  GAA  GAC  TTC  AGG  AAG  TAT  ACT  GCA  TTT  ACC  ATA  CCT       336
Val  Pro  Leu  Asp  Glu  Asp  Phe  Arg  Lys  Tyr  Thr  Ala  Phe  Thr  Ile  Pro
                     100                      105                     110

AGT  ATA  AAC  AAT  GAG  ACA  CCA  GGG  ATT  AGA  TAT  CAG  TAC  AAT  GTG  CTT       384
Ser  Ile  Asn  Asn  Glu  Thr  Pro  Gly  Ile  Arg  Tyr  Gln  Tyr  Asn  Val  Leu
               115                      120                      125

CCA  CAG  GGA  TGG  AAA  GGA  TCA  CCA  GCA  ATA  TTC  CAA  AGT  AGC  ATG  ACA       432
Pro  Gln  Gly  Trp  Lys  Gly  Ser  Pro  Ala  Ile  Phe  Gln  Ser  Ser  Met  Thr
          130                      135                      140

AAA  ATC  TTA  GAG  CCT  TTT  AGA  AAA  CAA  AAT  CCA  GAC  ATA  GTT  ATC  TAT       480
Lys  Ile  Leu  Glu  Pro  Phe  Arg  Lys  Gln  Asn  Pro  Asp  Ile  Val  Ile  Tyr
     145                      150                      155

CAA  TAC  ATG  GAT  GAT  TTG  TAT  GTA  GGA  TCT  GAC  TTA  GAA  ATA  GGG  CAG       528
Gln  Tyr  Met  Asp  Asp  Leu  Tyr  Val  Gly  Ser  Asp  Leu  Glu  Ile  Gly  Gln
160                      165                      170                      175

CAT  AGA  ACA  AAA  ATA  GAG  GAG  CTG  AGA  CAA  CAT  CTG  TTG  AGG  TGG  GGA       576
His  Arg  Thr  Lys  Ile  Glu  Glu  Leu  Arg  Gln  His  Leu  Leu  Arg  Trp  Gly
                    180                      185                      190

CTT  ACC  ACA  CCA  GAC  AAA  AAA  CAT  CAG  AAA  GAA  CCT  CCA  TTC  CTT  TGG       624
Leu  Thr  Thr  Pro  Asp  Lys  Lys  His  Gln  Lys  Glu  Pro  Pro  Phe  Leu  Trp
               195                      200                      205

ATG  GGT  TAT  GAA  CTC  CAT  CCT  GAT  AAA  TGG  ACA  GTA  CAG  CCT  ATA  GTG       672
Met  Gly  Tyr  Glu  Leu  His  Pro  Asp  Lys  Trp  Thr  Val  Gln  Pro  Ile  Val
          210                      215                      220

CTG  CCA  GAA  AAA  GAC  AGC  TGG  ACT  GTC  AAT  GAC  ATA  CAG  AAG  TTA  GTG       720
Leu  Pro  Glu  Lys  Asp  Ser  Trp  Thr  Val  Asn  Asp  Ile  Gln  Lys  Leu  Val
     225                      230                      235

GGG  AAA  TTG  AAT  TGG  GCA  AGT  CAG  ATT  TAC  CCA  GGG  ATT  AAA  GTA  AGG       768
Gly  Lys  Leu  Asn  Trp  Ala  Ser  Gln  Ile  Tyr  Pro  Gly  Ile  Lys  Val  Arg
240                      245                      250                      255

CAA  TTA  TGT  AAA  CTC  CTT  AGA  GGA  ACC  AAA  GCA  CTA  ACA  GAA  GTA  ATA       816
Gln  Leu  Cys  Lys  Leu  Leu  Arg  Gly  Thr  Lys  Ala  Leu  Thr  Glu  Val  Ile
                    260                      265                      270

CCA  CTA  ACA  GAA  GAA  GCA  GAG  CTA  GAA  CTG  GCA  GAA  AAC  AGA  GAG  ATT       864
Pro  Leu  Thr  Glu  Glu  Ala  Glu  Leu  Glu  Leu  Ala  Glu  Asn  Arg  Glu  Ile
               275                      280                      285

CTA  AAA  GAA  CCA  GTA  CAT  GGA  GTG  TAT  TAT  GAC  CCA  TCA  AAA  GAC  TTA       912
Leu  Lys  Glu  Pro  Val  His  Gly  Val  Tyr  Tyr  Asp  Pro  Ser  Lys  Asp  Leu
          290                      295                      300

ATA  GCA  GAA  ATA  CAG  AAG  CAG  GGG  CAA  GGC  CTCGAG                             948
Ile  Ala  Glu  Ile  Gln  Lys  Gln  Gly  Gln  Gly
               305                      310
```

( 2 ) INFORMATION FOR SEQ ID NO:6:

( i ) SEQUENCE CHARACTERISTICS:
           ( A ) LENGTH: 314 amino acids
           ( B ) TYPE: amino acid
           ( D ) TOPOLOGY: linear ( i i ) MOLECULE TYPE: protein ( x i ) SEQUENCE DESCRIPTION: SEQ ID NO:6:

```
Gln  Trp  Pro  Leu  Thr  Glu  Glu  Lys  Ile  Lys  Ala  Leu  Val  Glu  Ile  Cys
  1                 5                      10                           15
```

-continued

| | | | | | | | | | | | | | | |
|---|---|---|---|---|---|---|---|---|---|---|---|---|---|---|
| Thr | Glu | Met | Glu | Lys | Glu | Gly | Lys | Ile | Ser | Lys | Ile | Gly | Pro | Glu | Asn |
| | | | 20 | | | | 25 | | | | | 30 | | |
| Pro | Tyr | Asn | Thr | Pro | Val | Phe | Ala | Ile | Lys | Lys | Lys | Asp | Ser | Thr | Lys |
| | | 35 | | | | 40 | | | | | 45 | | | |
| Trp | Arg | Lys | Leu | Val | Asp | Phe | Arg | Glu | Leu | Asn | Lys | Arg | Thr | Gln | Asp |
| | | 50 | | | | 55 | | | | | | 60 | | | |
| Phe | Trp | Glu | Val | Gln | Leu | Gly | Ile | Pro | His | Pro | Ala | Gly | Leu | Lys | Lys |
| 65 | | | | | 70 | | | | | 75 | | | | | 80 |
| Lys | Lys | Ser | Val | Thr | Val | Leu | Asp | Val | Gly | Asp | Ala | Tyr | Phe | Ser | Val |
| | | | | 85 | | | | | 90 | | | | | 95 | |
| Pro | Leu | Asp | Glu | Asp | Phe | Arg | Lys | Tyr | Thr | Ala | Phe | Thr | Ile | Pro | Ser |
| | | | | 100 | | | | | 105 | | | | 110 | | |
| Ile | Asn | Asn | Glu | Thr | Pro | Gly | Ile | Arg | Tyr | Gln | Tyr | Asn | Val | Leu | Pro |
| | | | 115 | | | | | 120 | | | | | 125 | | |
| Gln | Gly | Trp | Lys | Gly | Ser | Pro | Ala | Ile | Phe | Gln | Ser | Ser | Met | Thr | Lys |
| | 130 | | | | | 135 | | | | | 140 | | | | |
| Ile | Leu | Glu | Pro | Phe | Arg | Lys | Gln | Asn | Pro | Asp | Ile | Val | Ile | Tyr | Gln |
| 145 | | | | | 150 | | | | | 155 | | | | | 160 |
| Tyr | Met | Asp | Asp | Leu | Tyr | Val | Gly | Ser | Asp | Leu | Glu | Ile | Gly | Gln | His |
| | | | | 165 | | | | | 170 | | | | | 175 | |
| Arg | Thr | Lys | Ile | Glu | Glu | Leu | Arg | Gln | His | Leu | Leu | Arg | Trp | Gly | Leu |
| | | | 180 | | | | | 185 | | | | | 190 | | |
| Thr | Thr | Pro | Asp | Lys | Lys | His | Gln | Lys | Glu | Pro | Pro | Phe | Leu | Trp | Met |
| | | | 195 | | | | | 200 | | | | | 205 | | |
| Gly | Tyr | Glu | Leu | His | Pro | Asp | Lys | Trp | Thr | Val | Gln | Pro | Ile | Val | Leu |
| | 210 | | | | | 215 | | | | | 220 | | | | |
| Pro | Glu | Lys | Asp | Ser | Trp | Thr | Val | Asn | Asp | Ile | Gln | Lys | Leu | Val | Gly |
| 225 | | | | | 230 | | | | | 235 | | | | | 240 |
| Lys | Leu | Asn | Trp | Ala | Ser | Gln | Ile | Tyr | Pro | Gly | Ile | Lys | Val | Arg | Gln |
| | | | | 245 | | | | | 250 | | | | | 255 | |
| Leu | Cys | Lys | Leu | Leu | Arg | Gly | Thr | Lys | Ala | Leu | Thr | Glu | Val | Ile | Pro |
| | | | 260 | | | | | 265 | | | | | 270 | | |
| Leu | Thr | Glu | Glu | Ala | Glu | Leu | Glu | Leu | Ala | Glu | Asn | Arg | Glu | Ile | Leu |
| | | 275 | | | | | 280 | | | | | 285 | | | |
| Lys | Glu | Pro | Val | His | Gly | Val | Tyr | Tyr | Asp | Pro | Ser | Lys | Asp | Leu | Ile |
| | 290 | | | | | 295 | | | | | 300 | | | | |
| Ala | Glu | Ile | Gln | Lys | Gln | Gly | Gln | Gly | Leu | | | | | | |
| 305 | | | | | 310 | | | | | | | | | | |

( 2 ) INFORMATION FOR SEQ ID NO:7:

( i ) SEQUENCE CHARACTERISTICS:
        ( A ) LENGTH: 1568 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 7..1565

( x i ) SEQUENCE DESCRIPTION: SEQ ID NO:7:

| | | | | | | | | | | | | |
|---|---|---|---|---|---|---|---|---|---|---|---|---|
| GGGGCC | TGT | CCA | AAG | GTA | TCC | TTT | GAG | CCA | ATT | CCC | ATA | CAT | TAT | TGT | 4 8 |
| | Cys | Pro | Lys | Val | Ser | Phe | Glu | Pro | Ile | Pro | Ile | His | Tyr | Cys | |
| | 1 | | | | 5 | | | | | 10 | | | | | |
| GCC | CCG | GCT | GGT | TTT | GCG | ATT | CTA | AAA | TGT | AAT | AAT | AAG | ACG | TTC | AAT | 9 6 |
| Ala | Pro | Ala | Gly | Phe | Ala | Ile | Leu | Lys | Cys | Asn | Asn | Lys | Thr | Phe | Asn |

```
        15                          20                           25                           30
GGA   ACA   GGA   CCA   TGT   ACA   AAT   GTC   AGC   ACA   GTA   CAA   TGT   ACA   CAT   GGA        144
Gly   Thr   Gly   Pro   Cys   Thr   Asn   Val   Ser   Thr   Val   Gln   Cys   Thr   His   Gly
                        35                      40                      45

ATT   AGG   CCA   GTA   GTA   TCA   ACT   CAA   CTG   CTG   TTA   AAT   GGC   AGT   CTA   GCA        192
Ile   Arg   Pro   Val   Val   Ser   Thr   Gln   Leu   Leu   Leu   Asn   Gly   Ser   Leu   Ala
                  50                      55                            60

GAA   GAA   GAG   GTA   GTA   ATT   AGA   TCT   GTC   AAT   TTC   ACG   GAC   AAT   GCT   AAA        240
Glu   Glu   Glu   Val   Val   Ile   Arg   Ser   Val   Asn   Phe   Thr   Asp   Asn   Ala   Lys
            65                            70                      75

ACC   ATA   ATA   GTA   CAG   CTG   AAC   ACA   TCT   GTA   GAA   ATT   AAT   TGT   ACA   AGA        288
Thr   Ile   Ile   Val   Gln   Leu   Asn   Thr   Ser   Val   Glu   Ile   Asn   Cys   Thr   Arg
            80                            85                      90

CCC   AAC   AAC   AAT   ACA   AGA   AAA   AGA   ATC   CGT   ATC   CAG   AGA   GGA   CCA   GGG        336
Pro   Asn   Asn   Asn   Thr   Arg   Lys   Arg   Ile   Arg   Ile   Gln   Arg   Gly   Pro   Gly
95                            100                     105                           110

AGA   GCA   TTT   GTT   ACA   ATA   GGA   AAA   ATA   GGA   AAT   ATG   AGA   CAA   GCA   CAT        384
Arg   Ala   Phe   Val   Thr   Ile   Gly   Lys   Ile   Gly   Asn   Met   Arg   Gln   Ala   His
                        115                     120                           125

TGT   AAC   ATT   AGT   AGA   GCA   AAA   TGG   AAT   AAC   ACT   TTA   AAA   CAG   ATA   GAT        432
Cys   Asn   Ile   Ser   Arg   Ala   Lys   Trp   Asn   Asn   Thr   Leu   Lys   Gln   Ile   Asp
                  130                           135                           140

AGC   AAA   TTA   AGA   GAA   CAA   TTC   GGA   AAT   AAT   AAA   ACA   ATA   ATC   TTT   AAG        480
Ser   Lys   Leu   Arg   Glu   Gln   Phe   Gly   Asn   Asn   Lys   Thr   Ile   Ile   Phe   Lys
            145                           150                           155

CAA   TCC   TCA   GGA   GGG   GAC   CCA   GAA   ATT   GTA   ACG   CAC   AGT   TTT   AAT   TGT        528
Gln   Ser   Ser   Gly   Gly   Asp   Pro   Glu   Ile   Val   Thr   His   Ser   Phe   Asn   Cys
            160                           165                           170

GGA   GGG   GAA   TTT   TTC   TAC   TGT   AAT   TCA   ACA   CAA   CTG   TTT   AAT   AGT   ACT        576
Gly   Gly   Glu   Phe   Phe   Tyr   Cys   Asn   Ser   Thr   Gln   Leu   Phe   Asn   Ser   Thr
175                           180                           185                           190

TGG   TTT   AAT   AGT   ACT   TGG   AGT   ACT   GAA   GGG   TCA   AAT   AAC   ACT   GAA   GGA        624
Trp   Phe   Asn   Ser   Thr   Trp   Ser   Thr   Glu   Gly   Ser   Asn   Asn   Thr   Glu   Gly
                        195                           200                           205

AGT   GAC   ACA   ATC   ACC   CTC   CCA   TGC   AGA   ATA   AAA   CAA   ATT   ATA   AAC   ATG        672
Ser   Asp   Thr   Ile   Thr   Leu   Pro   Cys   Arg   Ile   Lys   Gln   Ile   Ile   Asn   Met
                  210                           215                           220

TGG   CAG   AAA   GTA   GGA   AAA   GCA   ATG   TAT   GCC   CCT   CCC   ATC   AGT   GGA   CAA        720
Trp   Gln   Lys   Val   Gly   Lys   Ala   Met   Tyr   Ala   Pro   Pro   Ile   Ser   Gly   Gln
            225                           230                           235

ATT   AGA   TGT   TCA   TCA   AAT   ATT   ACA   GGG   CTG   CTA   TTA   ACA   AGA   GAT   GGT        768
Ile   Arg   Cys   Ser   Ser   Asn   Ile   Thr   Gly   Leu   Leu   Leu   Thr   Arg   Asp   Gly
            240                           245                           250

GGT   AAT   AGC   AAC   AAT   GAG   TCC   GAG   ATC   TTC   AGA   CTT   GGA   GGA   GGA   GAT        816
Gly   Asn   Ser   Asn   Asn   Glu   Ser   Glu   Ile   Phe   Arg   Leu   Gly   Gly   Gly   Asp
255                           260                           265                           270

ATG   AGG   GAC   AAT   TGG   AGA   AGT   GAA   TTA   TAT   AAA   TAT   AAA   GTA   GTA   AAA        864
Met   Arg   Asp   Asn   Trp   Arg   Ser   Glu   Leu   Tyr   Lys   Tyr   Lys   Val   Val   Lys
                        275                           280                           285

ATT   GAA   CCA   TTA   GGA   GTA   GCA   CCC   ACC   AAG   GCA   AAG   AGA   AGA   GTG   GTG        912
Ile   Glu   Pro   Leu   Gly   Val   Ala   Pro   Thr   Lys   Ala   Lys   Arg   Arg   Val   Val
                  290                           295                           300

CAG   AGA   GAA   AAA   AGA   GCA   GTG   GGA   ATA   GGA   GCT   TTG   TTC   CTT   GGG   TTC        960
Gln   Arg   Glu   Lys   Arg   Ala   Val   Gly   Ile   Gly   Ala   Leu   Phe   Leu   Gly   Phe
            305                           310                           315

TTG   GGA   GCA   GCA   GGA   AGC   ACT   ATG   GGC   GCA   GCC   TCA   ATG   ACG   CTG   ACG       1008
Leu   Gly   Ala   Ala   Gly   Ser   Thr   Met   Gly   Ala   Ala   Ser   Met   Thr   Leu   Thr
            320                           325                           330

GTA   CAG   GCC   AGA   CAA   TTA   TTG   TCT   GGT   ATA   GTG   CAG   CAG   CAG   AAC   AAT       1056
Val   Gln   Ala   Arg   Gln   Leu   Leu   Ser   Gly   Ile   Val   Gln   Gln   Gln   Asn   Asn
```

|  |  |  |  |  |  |  |  |  |  |  |  |  |  |  |  |  |
|---|---|---|---|---|---|---|---|---|---|---|---|---|---|---|---|---|
| 335 |  |  |  |  | 340 |  |  |  |  | 345 |  |  |  |  | 350 |  |
| TTG | CTG | AGG | GCT | ATT | GAG | GCG | CAA | CAG | CAT | CTG | TTG | CAA | CTC | ACA | GTC | 1104 |
| Leu | Leu | Arg | Ala | Ile | Glu | Ala | Gln | Gln | His | Leu | Leu | Gln | Leu | Thr | Val |  |
|  |  |  |  | 355 |  |  |  |  | 360 |  |  |  |  | 365 |  |  |
| TGG | GGC | ATC | AAG | CAG | CTC | CAA | GCA | AGA | ATC | CTA | GCT | GTG | GAA | AGA | TAC | 1152 |
| Trp | Gly | Ile | Lys | Gln | Leu | Gln | Ala | Arg | Ile | Leu | Ala | Val | Glu | Arg | Tyr |  |
|  |  |  | 370 |  |  |  |  | 375 |  |  |  |  | 380 |  |  |  |
| CTA | AAG | GAT | CAA | CAG | CTC | CTA | GGG | ATT | TGG | GGT | TGC | TCT | GGA | AAA | CTC | 1200 |
| Leu | Lys | Asp | Gln | Gln | Leu | Leu | Gly | Ile | Trp | Gly | Cys | Ser | Gly | Lys | Leu |  |
|  |  | 385 |  |  |  |  | 390 |  |  |  |  | 395 |  |  |  |  |
| ATT | TGC | ACC | ACT | GCT | GTG | CCT | TGG | AAT | GCT | AGT | TGG | AGT | AAT | AAA | TCT | 1248 |
| Ile | Cys | Thr | Thr | Ala | Val | Pro | Trp | Asn | Ala | Ser | Trp | Ser | Asn | Lys | Ser |  |
|  | 400 |  |  |  |  | 405 |  |  |  |  | 410 |  |  |  |  |  |
| CTG | GAA | CAG | ATC | TGG | AAT | CAC | ACG | ACC | TGG | ATG | GAG | TGG | GAC | AGA | GAA | 1296 |
| Leu | Glu | Gln | Ile | Trp | Asn | His | Thr | Thr | Trp | Met | Glu | Trp | Asp | Arg | Glu |  |
| 415 |  |  |  |  | 420 |  |  |  |  | 425 |  |  |  |  | 430 |  |
| ATT | AAC | AAT | TAC | ACA | AGC | TTA | ATA | CAC | TCC | TTA | ATT | GAA | GAA | TCG | CAA | 1344 |
| Ile | Asn | Asn | Tyr | Thr | Ser | Leu | Ile | His | Ser | Leu | Ile | Glu | Glu | Ser | Gln |  |
|  |  |  |  | 435 |  |  |  |  | 440 |  |  |  |  | 445 |  |  |
| AAC | CAG | CAA | GAA | AAG | AAT | GAA | CAA | GAA | TTA | TTG | GAA | TTA | GAT | AAA | TGG | 1392 |
| Asn | Gln | Gln | Glu | Lys | Asn | Glu | Gln | Glu | Leu | Leu | Glu | Leu | Asp | Lys | Trp |  |
|  |  |  | 450 |  |  |  |  | 455 |  |  |  |  | 460 |  |  |  |
| GCA | AGT | TTG | TGG | AAT | TGG | TTT | AAC | ATA | ACA | AAT | TGG | CTG | TGG | TAT | ATA | 1440 |
| Ala | Ser | Leu | Trp | Asn | Trp | Phe | Asn | Ile | Thr | Asn | Trp | Leu | Trp | Tyr | Ile |  |
|  |  | 465 |  |  |  |  | 470 |  |  |  |  | 475 |  |  |  |  |
| AAA | TTA | TTC | ATA | ATG | ATA | GTA | GGA | GGC | TTG | GTA | GGT | TTA | AGA | ATA | GTT | 1488 |
| Lys | Leu | Phe | Ile | Met | Ile | Val | Gly | Gly | Leu | Val | Gly | Leu | Arg | Ile | Val |  |
|  | 480 |  |  |  |  | 485 |  |  |  |  | 490 |  |  |  |  |  |
| TTT | GCT | GTA | CTT | TCT | ATA | GTG | AAT | AGA | GTT | AGG | CAG | GGA | TAT | TCA | CCA | 1536 |
| Phe | Ala | Val | Leu | Ser | Ile | Val | Asn | Arg | Val | Arg | Gln | Gly | Tyr | Ser | Pro |  |
| 495 |  |  |  |  | 500 |  |  |  |  | 505 |  |  |  |  | 510 |  |
| TTA | TCG | TTT | CAG | ACC | CAC | CTC | CCA | ATC | TCGAG |  |  |  |  |  |  | 1568 |
| Leu | Ser | Phe | Gln | Thr | His | Leu | Pro | Ile |  |  |  |  |  |  |  |  |
|  |  |  |  | 515 |  |  |  |  |  |  |  |  |  |  |  |  |

( 2 ) INFORMATION FOR SEQ ID NO:8:

( i ) SEQUENCE CHARACTERISTICS:
        ( A ) LENGTH: 519 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Cys | Pro | Lys | Val | Ser | Phe | Glu | Pro | Ile | Pro | Ile | His | Tyr | Cys | Ala | Pro |
|---|---|---|---|---|---|---|---|---|---|---|---|---|---|---|---|
| 1 |  |  |  | 5 |  |  |  |  | 10 |  |  |  |  | 15 |  |
| Ala | Gly | Phe | Ala | Ile | Leu | Lys | Cys | Asn | Asn | Lys | Thr | Phe | Asn | Gly | Thr |
|  |  |  | 20 |  |  |  |  | 25 |  |  |  |  | 30 |  |  |
| Gly | Pro | Cys | Thr | Asn | Val | Ser | Thr | Val | Gln | Cys | Thr | His | Gly | Ile | Arg |
|  |  | 35 |  |  |  |  | 40 |  |  |  |  | 45 |  |  |  |
| Pro | Val | Val | Ser | Thr | Gln | Leu | Leu | Leu | Asn | Gly | Ser | Leu | Ala | Glu | Glu |
|  | 50 |  |  |  |  | 55 |  |  |  |  | 60 |  |  |  |  |
| Glu | Val | Val | Ile | Arg | Ser | Val | Asn | Phe | Thr | Asp | Asn | Ala | Lys | Thr | Ile |
| 65 |  |  |  |  | 70 |  |  |  |  | 75 |  |  |  |  | 80 |
| Ile | Val | Gln | Leu | Asn | Thr | Ser | Val | Glu | Ile | Asn | Cys | Thr | Arg | Pro | Asn |
|  |  |  |  | 85 |  |  |  |  | 90 |  |  |  |  | 95 |  |
| Asn | Asn | Thr | Arg | Lys | Arg | Ile | Arg | Ile | Gln | Arg | Gly | Pro | Gly | Arg | Ala |
|  |  |  | 100 |  |  |  |  | 105 |  |  |  |  | 110 |  |  |
| Phe | Val | Thr | Ile | Gly | Lys | Ile | Gly | Asn | Met | Arg | Gln | Ala | His | Cys | Asn |

|     |     |     | 115 |     |     |     |     | 120 |     |     |     |     | 125 |     |     |
| --- | --- | --- | --- | --- | --- | --- | --- | --- | --- | --- | --- | --- | --- | --- | --- |
| Ile | Ser | Arg | Ala | Lys | Trp | Asn | Asn | Thr | Leu | Lys | Gln | Ile | Asp | Ser | Lys |
|     | 130 |     |     |     |     | 135 |     |     |     |     | 140 |     |     |     |     |
| Leu | Arg | Glu | Gln | Phe | Gly | Asn | Asn | Lys | Thr | Ile | Ile | Phe | Lys | Gln | Ser |
| 145 |     |     |     |     | 150 |     |     |     |     | 155 |     |     |     |     | 160 |
| Ser | Gly | Gly | Asp | Pro | Glu | Ile | Val | Thr | His | Ser | Phe | Asn | Cys | Gly | Gly |
|     |     |     |     | 165 |     |     |     |     | 170 |     |     |     |     | 175 |     |
| Glu | Phe | Phe | Tyr | Cys | Asn | Ser | Thr | Gln | Leu | Phe | Asn | Ser | Thr | Trp | Phe |
|     |     |     | 180 |     |     |     |     | 185 |     |     |     |     | 190 |     |     |
| Asn | Ser | Thr | Trp | Ser | Thr | Glu | Gly | Ser | Asn | Asn | Thr | Glu | Gly | Ser | Asp |
|     |     | 195 |     |     |     |     | 200 |     |     |     |     | 205 |     |     |     |
| Thr | Ile | Thr | Leu | Pro | Cys | Arg | Ile | Lys | Gln | Ile | Ile | Asn | Met | Trp | Gln |
|     | 210 |     |     |     |     | 215 |     |     |     |     | 220 |     |     |     |     |
| Lys | Val | Gly | Lys | Ala | Met | Tyr | Ala | Pro | Pro | Ile | Ser | Gly | Gln | Ile | Arg |
| 225 |     |     |     |     | 230 |     |     |     |     | 235 |     |     |     |     | 240 |
| Cys | Ser | Ser | Asn | Ile | Thr | Gly | Leu | Leu | Leu | Thr | Arg | Asp | Gly | Gly | Asn |
|     |     |     |     | 245 |     |     |     |     | 250 |     |     |     |     | 255 |     |
| Ser | Asn | Asn | Glu | Ser | Glu | Ile | Phe | Arg | Leu | Gly | Gly | Gly | Asp | Met | Arg |
|     |     |     | 260 |     |     |     |     | 265 |     |     |     |     | 270 |     |     |
| Asp | Asn | Trp | Arg | Ser | Glu | Leu | Tyr | Lys | Tyr | Lys | Val | Val | Lys | Ile | Glu |
|     |     | 275 |     |     |     |     | 280 |     |     |     |     | 285 |     |     |     |
| Pro | Leu | Gly | Val | Ala | Pro | Thr | Lys | Ala | Lys | Arg | Arg | Val | Val | Gln | Arg |
|     | 290 |     |     |     |     | 295 |     |     |     |     | 300 |     |     |     |     |
| Glu | Lys | Arg | Ala | Val | Gly | Ile | Gly | Ala | Leu | Phe | Leu | Gly | Phe | Leu | Gly |
| 305 |     |     |     |     | 310 |     |     |     |     | 315 |     |     |     |     | 320 |
| Ala | Ala | Gly | Ser | Thr | Met | Gly | Ala | Ala | Ser | Met | Thr | Leu | Thr | Val | Gln |
|     |     |     |     | 325 |     |     |     |     | 330 |     |     |     |     | 335 |     |
| Ala | Arg | Gln | Leu | Leu | Ser | Gly | Ile | Val | Gln | Gln | Asn | Asn | Leu | Leu |     |
|     |     |     | 340 |     |     |     |     | 345 |     |     |     |     | 350 |     |     |
| Arg | Ala | Ile | Glu | Ala | Gln | Gln | His | Leu | Leu | Gln | Leu | Thr | Val | Trp | Gly |
|     |     | 355 |     |     |     |     | 360 |     |     |     |     | 365 |     |     |     |
| Ile | Lys | Gln | Leu | Gln | Ala | Arg | Ile | Leu | Ala | Val | Glu | Arg | Tyr | Leu | Lys |
|     | 370 |     |     |     |     | 375 |     |     |     |     | 380 |     |     |     |     |
| Asp | Gln | Gln | Leu | Leu | Gly | Ile | Trp | Gly | Cys | Ser | Gly | Lys | Leu | Ile | Cys |
| 385 |     |     |     |     | 390 |     |     |     |     | 395 |     |     |     |     | 400 |
| Thr | Thr | Ala | Val | Pro | Trp | Asn | Ala | Ser | Trp | Ser | Asn | Lys | Ser | Leu | Glu |
|     |     |     |     | 405 |     |     |     |     | 410 |     |     |     |     | 415 |     |
| Gln | Ile | Trp | Asn | His | Thr | Thr | Trp | Met | Glu | Trp | Asp | Arg | Glu | Ile | Asn |
|     |     |     | 420 |     |     |     |     | 425 |     |     |     |     | 430 |     |     |
| Asn | Tyr | Thr | Ser | Leu | Ile | His | Ser | Leu | Ile | Glu | Glu | Ser | Gln | Asn | Gln |
|     |     | 435 |     |     |     |     | 440 |     |     |     |     | 445 |     |     |     |
| Gln | Glu | Lys | Asn | Glu | Gln | Glu | Leu | Leu | Glu | Leu | Asp | Lys | Trp | Ala | Ser |
|     | 450 |     |     |     |     | 455 |     |     |     |     | 460 |     |     |     |     |
| Leu | Trp | Asn | Trp | Phe | Asn | Ile | Thr | Asn | Trp | Leu | Trp | Tyr | Ile | Lys | Leu |
| 465 |     |     |     |     | 470 |     |     |     |     | 475 |     |     |     |     | 480 |
| Phe | Ile | Met | Ile | Val | Gly | Gly | Leu | Val | Gly | Leu | Arg | Ile | Val | Phe | Ala |
|     |     |     |     | 485 |     |     |     |     | 490 |     |     |     |     | 495 |     |
| Val | Leu | Ser | Ile | Val | Asn | Arg | Val | Arg | Gln | Gly | Tyr | Ser | Pro | Leu | Ser |
|     |     |     | 500 |     |     |     |     | 505 |     |     |     |     | 510 |     |     |
| Phe | Gln | Thr | His | Leu | Pro | Ile |     |     |     |     |     |     |     |     |     |
|     |     | 515 |     |     |     |     |     |     |     |     |     |     |     |     |     |

( 2 ) INFORMATION FOR SEQ ID NO:9:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

CACCCCTCTC CTACGTAACC AAGGATC                27

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GTACTGGTCA CCATATTGGT CAAC                    24

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGAGAGAGAT GGGAGCTCGA GCGTC                  25

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCCCCCTAT ACGTATTGTG                        20

( 2 ) INFORMATION FOR SEQ ID NO:13:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CCAGTGAATT CCTAATACGA CTCACTATAG GTTAAAACAG C        41

( 2 ) INFORMATION FOR SEQ ID NO:14:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:14:

```
CTCTATCCTG  AGCTCCATAT  GTGTCGAGCA  GTTTTTGGTT  TAGCATTG                    48
```

(2) INFORMATION FOR SEQ ID NO:15:

(i) SEQUENCE CHARACTERISTICS:
        (A) LENGTH: 8 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO:15:

```
Thr  Lys  Asp  Leu  Thr  Thr  Tyr  Gly
 1                    5
```

(2) INFORMATION FOR SEQ ID NO:16:

(i) SEQUENCE CHARACTERISTICS:
        (A) LENGTH: 2220 base pairs
        (B) TYPE: nucleic acid
        (C) STRANDEDNESS: single
        (D) TOPOLOGY: linear (i i) MOLECULE TYPE: cDNA (i x) FEATURE:
        (A) NAME/KEY: CDS
        (B) LOCATION: 1..2203

(x i) SEQUENCE DESCRIPTION: SEQ ID NO:16:

```
CGA  CCA  GCA  GAC  CAG  ACA  GTC  ACA  GCA  GCC  TTG  ACA  AAA  CGT  TCC  TGG        48
Arg  Pro  Ala  Asp  Gln  Thr  Val  Thr  Ala  Ala  Leu  Thr  Lys  Arg  Ser  Trp
 1                    5                   10                   15

AAC  TCA  AGC  ACT  TCT  CCA  CAG  AGG  AGG  ACA  GAG  CAG  ACA  GCA  GAG  ACC        96
Asn  Ser  Ser  Thr  Ser  Pro  Gln  Arg  Arg  Thr  Glu  Gln  Thr  Ala  Glu  Thr
                     20                   25                   30

ATG  GAG  TCT  CCC  TCG  GCC  CCT  CCC  CAC  AGA  TGG  TGC  ATC  CCC  TGG  CAG       144
Met  Glu  Ser  Pro  Ser  Ala  Pro  Pro  His  Arg  Trp  Cys  Ile  Pro  Trp  Gln
           35                   40                   45

AGG  CTC  CTG  CTC  ACA  GCC  TCA  CTT  CTA  ACC  TTC  TGG  AAC  CCG  CCC  ACC       192
Arg  Leu  Leu  Leu  Thr  Ala  Ser  Leu  Leu  Thr  Phe  Trp  Asn  Pro  Pro  Thr
      50                   55                   60

ACT  GCC  AAG  CTC  ACT  ATT  GAA  TCC  ACG  CCG  TTC  AAT  GTC  GCA  GAG  GGG       240
Thr  Ala  Lys  Leu  Thr  Ile  Glu  Ser  Thr  Pro  Phe  Asn  Val  Ala  Glu  Gly
 65                   70                   75                   80

AAG  GAG  GTG  CTT  CTA  CTT  GTC  CAC  AAT  CTG  CCC  CAG  CAT  CTT  TTT  GGC       288
Lys  Glu  Val  Leu  Leu  Leu  Val  His  Asn  Leu  Pro  Gln  His  Leu  Phe  Gly
                     85                   90                   95

TAC  AGC  TGG  TAC  AAA  GGT  GAA  AGA  GTG  GAT  GGC  AAC  CGT  CAA  ATT  ATA       336
Tyr  Ser  Trp  Tyr  Lys  Gly  Glu  Arg  Val  Asp  Gly  Asn  Arg  Gln  Ile  Ile
                100                  105                  110

GGA  TAT  GTA  ATA  GGA  ACT  CAA  CAA  GCT  ACC  CCA  GGG  CCC  GCA  TAC  AGT       384
Gly  Tyr  Val  Ile  Gly  Thr  Gln  Gln  Ala  Thr  Pro  Gly  Pro  Ala  Tyr  Ser
           115                  120                  125

GGT  CGA  GAG  ATA  ATA  TAC  CCC  AAT  GCA  TCC  CTG  CTG  ATC  CAG  AAC  ATC       432
Gly  Arg  Glu  Ile  Ile  Tyr  Pro  Asn  Ala  Ser  Leu  Leu  Ile  Gln  Asn  Ile
      130                  135                  140

ATC  CAG  AAT  GAC  ACA  GGA  TTC  TAC  ACC  CTA  CAC  GTC  ATA  AAG  TCA  GAT       480
Ile  Gln  Asn  Asp  Thr  Gly  Phe  Tyr  Thr  Leu  His  Val  Ile  Lys  Ser  Asp
145                  150                  155                  160
```

| | | | | | | | | | | | | | | | | |
|---|---|---|---|---|---|---|---|---|---|---|---|---|---|---|---|---|
| CTT | GTG | AAT | GAA | GAA | GCA | ACT | GGC | CAG | TTC | CGG | GTA | TAC | CCG | GAG | CTG | 528 |
| Leu | Val | Asn | Glu | Glu | Ala | Thr | Gly | Gln | Phe | Arg | Val | Tyr | Pro | Glu | Leu | |
| | | | 165 | | | | | 170 | | | | | 175 | | | |
| CCC | AAG | CCC | TCC | ATC | TCC | AGC | AAC | AAC | TCC | AAA | CCC | GTG | GAG | GAC | AAG | 576 |
| Pro | Lys | Pro | Ser | Ile | Ser | Ser | Asn | Asn | Ser | Lys | Pro | Val | Glu | Asp | Lys | |
| | | | 180 | | | | | 185 | | | | | 190 | | | |
| GAT | GCT | GTG | GCC | TTC | ACC | TGT | GAA | CCT | GAG | ACT | CAG | GAC | GCA | ACC | TAC | 624 |
| Asp | Ala | Val | Ala | Phe | Thr | Cys | Glu | Pro | Glu | Thr | Gln | Asp | Ala | Thr | Tyr | |
| | | | 195 | | | | | 200 | | | | | 205 | | | |
| CTG | TGG | TGG | GTA | AAC | AAT | CAG | AGC | CTC | CCG | GTC | AGT | CCC | AGG | CTG | CAG | 672 |
| Leu | Trp | Trp | Val | Asn | Asn | Gln | Ser | Leu | Pro | Val | Ser | Pro | Arg | Leu | Gln | |
| | | | 210 | | | | | 215 | | | | | 220 | | | |
| CTG | TCC | AAT | GGC | AAC | AGG | ACC | CTC | ACT | CTA | TTC | AAT | GTC | ACA | AGA | AAT | 720 |
| Leu | Ser | Asn | Gly | Asn | Arg | Thr | Leu | Thr | Leu | Phe | Asn | Val | Thr | Arg | Asn | |
| 225 | | | | | 230 | | | | | 235 | | | | | 240 | |
| GAC | ACA | GCA | AGC | TAC | AAA | TGT | GAA | ACC | CAG | AAC | CCA | GTG | AGT | GCC | AGG | 768 |
| Asp | Thr | Ala | Ser | Tyr | Lys | Cys | Glu | Thr | Gln | Asn | Pro | Val | Ser | Ala | Arg | |
| | | | | 245 | | | | | 250 | | | | | 255 | | |
| CGC | AGT | GAT | TCA | GTC | ATC | CTG | AAT | GTC | CTC | TAT | GGC | CCG | GAT | GCC | CCC | 816 |
| Arg | Ser | Asp | Ser | Val | Ile | Leu | Asn | Val | Leu | Tyr | Gly | Pro | Asp | Ala | Pro | |
| | | | 260 | | | | | 265 | | | | | 270 | | | |
| ACC | ATT | TCC | CCT | CTA | AAC | ACA | TCT | TAC | AGA | TCA | GGG | GAA | AAT | CTG | AAC | 864 |
| Thr | Ile | Ser | Pro | Leu | Asn | Thr | Ser | Tyr | Arg | Ser | Gly | Glu | Asn | Leu | Asn | |
| | | 275 | | | | | 280 | | | | | 285 | | | | |
| CTC | TCC | TGC | CAT | GCA | GCC | TCT | AAC | CCA | CCT | GCA | CAG | TAC | TCT | TGG | TTT | 912 |
| Leu | Ser | Cys | His | Ala | Ala | Ser | Asn | Pro | Pro | Ala | Gln | Tyr | Ser | Trp | Phe | |
| | 290 | | | | | 295 | | | | | 300 | | | | | |
| GTC | AAT | GGG | ACT | TTC | CAG | CAA | TCC | ACC | CAA | GAG | CTC | TTT | ATC | CCC | AAC | 960 |
| Val | Asn | Gly | Thr | Phe | Gln | Gln | Ser | Thr | Gln | Glu | Leu | Phe | Ile | Pro | Asn | |
| 305 | | | | | 310 | | | | | 315 | | | | | 320 | |
| ATC | ACT | GTG | AAT | AAT | AGT | GGA | TCC | TAT | ACG | TGC | CAA | GCC | CAT | AAC | TCA | 1008 |
| Ile | Thr | Val | Asn | Asn | Ser | Gly | Ser | Tyr | Thr | Cys | Gln | Ala | His | Asn | Ser | |
| | | | | 325 | | | | | 330 | | | | | 335 | | |
| GAC | ACT | GGC | CTC | AAT | AGG | ACC | ACA | GTC | ACG | ACG | ATC | ACA | GTC | TAT | GCA | 1056 |
| Asp | Thr | Gly | Leu | Asn | Arg | Thr | Thr | Val | Thr | Thr | Ile | Thr | Val | Tyr | Ala | |
| | | | 340 | | | | | 345 | | | | | 350 | | | |
| GAG | CCA | CCC | AAA | CCC | TTC | ATC | ACC | AGC | AAC | AAC | TCC | AAC | CCC | GTG | GAG | 1104 |
| Glu | Pro | Pro | Lys | Pro | Phe | Ile | Thr | Ser | Asn | Asn | Ser | Asn | Pro | Val | Glu | |
| | | 355 | | | | | 360 | | | | | 365 | | | | |
| GAT | GAG | GAT | GCT | GTA | GCC | TTA | ACC | TGT | GAA | CCT | GAG | ATT | CAG | AAC | ACA | 1152 |
| Asp | Glu | Asp | Ala | Val | Ala | Leu | Thr | Cys | Glu | Pro | Glu | Ile | Gln | Asn | Thr | |
| | 370 | | | | | 375 | | | | | 380 | | | | | |
| ACC | TAC | CTG | TGG | TGG | GTA | AAT | AAT | CAG | AGC | CTC | CCG | GTC | AGT | CCC | AGG | 1200 |
| Thr | Tyr | Leu | Trp | Trp | Val | Asn | Asn | Gln | Ser | Leu | Pro | Val | Ser | Pro | Arg | |
| 385 | | | | | 390 | | | | | 395 | | | | | 400 | |
| CTG | CAG | CTG | TCC | AAT | GAC | AAC | AGG | ACC | CTC | ACT | CTA | CTC | AGT | GTC | ACA | 1248 |
| Leu | Gln | Leu | Ser | Asn | Asp | Asn | Arg | Thr | Leu | Thr | Leu | Leu | Ser | Val | Thr | |
| | | | | 405 | | | | | 410 | | | | | 415 | | |
| AGG | AAT | GAT | GTA | GGA | CCC | TAT | GAG | TGT | GGA | ATC | CAG | AAC | GAA | TTA | AGT | 1296 |
| Arg | Asn | Asp | Val | Gly | Pro | Tyr | Glu | Cys | Gly | Ile | Gln | Asn | Glu | Leu | Ser | |
| | | | 420 | | | | | 425 | | | | | 430 | | | |
| GTT | GAC | CAC | AGC | GAC | CCA | GTC | ATC | CTG | AAT | GTC | CTC | TAT | GGC | CCA | GAC | 1344 |
| Val | Asp | His | Ser | Asp | Pro | Val | Ile | Leu | Asn | Val | Leu | Tyr | Gly | Pro | Asp | |
| | | 435 | | | | | 440 | | | | | 445 | | | | |
| GAC | CCC | ACC | ATT | TCC | CCC | TCA | TAC | ACC | TAT | TAC | CGT | CCA | GGG | GTG | AAC | 1392 |
| Asp | Pro | Thr | Ile | Ser | Pro | Ser | Tyr | Thr | Tyr | Tyr | Arg | Pro | Gly | Val | Asn | |
| | 450 | | | | | 455 | | | | | 460 | | | | | |
| CTC | AGC | CTC | TCC | TGC | CAT | GCA | GCC | TCT | AAC | CCA | CCT | GCA | CAG | TAT | TCT | 1440 |
| Leu | Ser | Leu | Ser | Cys | His | Ala | Ala | Ser | Asn | Pro | Pro | Ala | Gln | Tyr | Ser | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| TGG | CTG | ATT | GAT | GGG | AAC | ATC | CAG | CAA | CAC | ACA | CAA | GAG | CTC | TTT | ATC | 1488 |
| Trp | Leu | Ile | Asp | Gly | Asn | Ile | Gln | Gln | His | Thr | Gln | Glu | Leu | Phe | Ile | |
| | | | | 485 | | | | | 490 | | | | | 495 | | |
| TCC | AAC | ATC | ACT | GAG | AAG | AAC | AGC | GGA | CTC | TAT | ACC | TGC | CAG | GCC | AAT | 1536 |
| Ser | Asn | Ile | Thr | Glu | Lys | Asn | Ser | Gly | Leu | Tyr | Thr | Cys | Gln | Ala | Asn | |
| | | | 500 | | | | | 505 | | | | | 510 | | | |
| AAC | TCA | GCC | AGT | GGC | CAC | AGC | AGG | ACT | ACA | GTC | AAG | ACA | ATC | ACA | GTC | 1584 |
| Asn | Ser | Ala | Ser | Gly | His | Ser | Arg | Thr | Thr | Val | Lys | Thr | Ile | Thr | Val | |
| | | 515 | | | | | 520 | | | | | 525 | | | | |
| TCT | GCG | GAG | CTG | CCC | AAG | CCC | TCC | ATC | TCC | AGC | AAC | AAC | TCC | AAA | CCC | 1632 |
| Ser | Ala | Glu | Leu | Pro | Lys | Pro | Ser | Ile | Ser | Ser | Asn | Asn | Ser | Lys | Pro | |
| | | 530 | | | | 535 | | | | | 540 | | | | | |
| GTG | GAG | GAC | AAG | GAT | GCT | GTG | GCC | TTC | ACC | TGT | GAA | CCT | GAG | GCT | CAG | 1680 |
| Val | Glu | Asp | Lys | Asp | Ala | Val | Ala | Phe | Thr | Cys | Glu | Pro | Glu | Ala | Gln | |
| 545 | | | | | 550 | | | | | 555 | | | | | 560 | |
| AAC | ACA | ACC | TAC | CTG | TGG | TGG | GTA | AAT | GGT | CAG | AGC | CTC | CCA | GTC | AGT | 1728 |
| Asn | Thr | Thr | Tyr | Leu | Trp | Trp | Val | Asn | Gly | Gln | Ser | Leu | Pro | Val | Ser | |
| | | | | 565 | | | | | 570 | | | | | 575 | | |
| CCC | AGG | CTG | CAG | CTG | TCC | AAT | GGC | AAC | AGG | ACC | CTC | ACT | CTA | TTC | AAT | 1776 |
| Pro | Arg | Leu | Gln | Leu | Ser | Asn | Gly | Asn | Arg | Thr | Leu | Thr | Leu | Phe | Asn | |
| | | 580 | | | | | 585 | | | | | 590 | | | | |
| GTC | ACA | AGA | AAT | GAC | GCA | AGA | GCC | TAT | GTA | TGT | GGA | ATC | CAG | AAC | TCA | 1824 |
| Val | Thr | Arg | Asn | Asp | Ala | Arg | Ala | Tyr | Val | Cys | Gly | Ile | Gln | Asn | Ser | |
| | | 595 | | | | | 600 | | | | | 605 | | | | |
| GTG | AGT | GCA | AAC | CGC | AGT | GAC | CCA | GTC | ACC | CTG | GAT | GTC | CTC | TAT | GGG | 1872 |
| Val | Ser | Ala | Asn | Arg | Ser | Asp | Pro | Val | Thr | Leu | Asp | Val | Leu | Tyr | Gly | |
| | | 610 | | | | | 615 | | | | | 620 | | | | |
| CCG | GAC | ACC | CCC | ATC | ATT | TCC | CCC | CCA | GAC | TCG | TCT | TAC | CTT | TCG | GGA | 1920 |
| Pro | Asp | Thr | Pro | Ile | Ile | Ser | Pro | Pro | Asp | Ser | Ser | Tyr | Leu | Ser | Gly | |
| 625 | | | | | 630 | | | | | 635 | | | | | 640 | |
| GCG | AAC | CTC | AAC | CTC | TCC | TGC | CAC | TCG | GCC | TCT | AAC | CCA | TCC | CCG | CAG | 1968 |
| Ala | Asn | Leu | Asn | Leu | Ser | Cys | His | Ser | Ala | Ser | Asn | Pro | Ser | Pro | Gln | |
| | | | | 645 | | | | | 650 | | | | | 655 | | |
| TAT | TCT | TGG | CGT | ATC | AAT | GGG | ATA | CCG | CAG | CAA | CAC | ACA | CAA | GTT | CTC | 2016 |
| Tyr | Ser | Trp | Arg | Ile | Asn | Gly | Ile | Pro | Gln | Gln | His | Thr | Gln | Val | Leu | |
| | | | 660 | | | | | 665 | | | | | 670 | | | |
| TTT | ATC | GCC | AAA | ATC | ACG | CCA | AAT | AAT | AAC | GGG | ACC | TAT | GCC | TGT | TTT | 2064 |
| Phe | Ile | Ala | Lys | Ile | Thr | Pro | Asn | Asn | Asn | Gly | Thr | Tyr | Ala | Cys | Phe | |
| | | 675 | | | | | 680 | | | | | 685 | | | | |
| GTC | TCT | AAC | TTG | GCT | ACT | GGC | CGC | AAT | AAT | TCC | ATA | GTC | AAG | AGC | ATC | 2112 |
| Val | Ser | Asn | Leu | Ala | Thr | Gly | Arg | Asn | Asn | Ser | Ile | Val | Lys | Ser | Ile | |
| | | 690 | | | | | 695 | | | | | 700 | | | | |
| ACA | GTC | TCT | GCA | TCT | GGA | ACT | TCT | CCT | GGT | CTC | TCA | GCT | GGG | GCC | ACT | 2160 |
| Thr | Val | Ser | Ala | Ser | Gly | Thr | Ser | Pro | Gly | Leu | Ser | Ala | Gly | Ala | Thr | |
| 705 | | | | | 710 | | | | | 715 | | | | | 720 | |
| GTC | GGC | ATC | ATG | ATT | GGA | GTG | CTG | GTT | GGG | GTT | GCT | CTG | ATA | | | 2202 |
| Val | Gly | Ile | Met | Ile | Gly | Val | Leu | Val | Gly | Val | Ala | Leu | Ile | | | |
| | | | | 725 | | | | | 730 | | | | | | | |
| TAGCAGCCCTGGTGTAGT | | | | | | | | | | | | | | | | 2220 |

( 2 ) INFORMATION FOR SEQ ID NO:17:

( i ) SEQUENCE CHARACTERISTICS:
        ( A ) LENGTH: 734 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

Arg    Pro    Ala    Asp    Gln    Thr    Val    Thr    Ala    Ala    Leu    Thr    Lys    Arg    Ser    Trp

-continued

```
  1                    5                         10                        15
Asn  Ser  Ser  Thr  Ser  Pro  Gln  Arg  Arg  Thr  Glu  Gln  Thr  Ala  Glu  Thr
               20                       25                       30
Met  Glu  Ser  Pro  Ser  Ala  Pro  Pro  His  Arg  Trp  Cys  Ile  Pro  Trp  Gln
               35                       40                       45
Arg  Leu  Leu  Leu  Thr  Ala  Ser  Leu  Leu  Thr  Phe  Trp  Asn  Pro  Pro  Thr
               50                       55                       60
Thr  Ala  Lys  Leu  Thr  Ile  Glu  Ser  Thr  Pro  Phe  Asn  Val  Ala  Glu  Gly
 65                       70                       75                       80
Lys  Glu  Val  Leu  Leu  Leu  Val  His  Asn  Leu  Pro  Gln  His  Leu  Phe  Gly
                    85                       90                       95
Tyr  Ser  Trp  Tyr  Lys  Gly  Glu  Arg  Val  Asp  Gly  Asn  Arg  Gln  Ile  Ile
               100                      105                      110
Gly  Tyr  Val  Ile  Gly  Thr  Gln  Gln  Ala  Thr  Pro  Gly  Pro  Ala  Tyr  Ser
               115                      120                      125
Gly  Arg  Glu  Ile  Ile  Tyr  Pro  Asn  Ala  Ser  Leu  Leu  Ile  Gln  Asn  Ile
          130                      135                      140
Ile  Gln  Asn  Asp  Thr  Gly  Phe  Tyr  Thr  Leu  His  Val  Ile  Lys  Ser  Asp
145                      150                      155                      160
Leu  Val  Asn  Glu  Glu  Ala  Thr  Gly  Gln  Phe  Arg  Val  Tyr  Pro  Glu  Leu
                    165                      170                      175
Pro  Lys  Pro  Ser  Ile  Ser  Ser  Asn  Asn  Ser  Lys  Pro  Val  Glu  Asp  Lys
               180                      185                      190
Asp  Ala  Val  Ala  Phe  Thr  Cys  Glu  Pro  Glu  Thr  Gln  Asp  Ala  Thr  Tyr
               195                      200                      205
Leu  Trp  Trp  Val  Asn  Asn  Gln  Ser  Leu  Pro  Val  Ser  Pro  Arg  Leu  Gln
     210                      215                      220
Leu  Ser  Asn  Gly  Asn  Arg  Thr  Leu  Thr  Leu  Phe  Asn  Val  Thr  Arg  Asn
225                      230                      235                      240
Asp  Thr  Ala  Ser  Tyr  Lys  Cys  Glu  Thr  Gln  Asn  Pro  Val  Ser  Ala  Arg
                    245                      250                      255
Arg  Ser  Asp  Ser  Val  Ile  Leu  Asn  Val  Leu  Tyr  Gly  Pro  Asp  Ala  Pro
               260                      265                      270
Thr  Ile  Ser  Pro  Leu  Asn  Thr  Ser  Tyr  Arg  Ser  Gly  Glu  Asn  Leu  Asn
               275                      280                      285
Leu  Ser  Cys  His  Ala  Ala  Ser  Asn  Pro  Pro  Ala  Gln  Tyr  Ser  Trp  Phe
     290                      295                      300
Val  Asn  Gly  Thr  Phe  Gln  Gln  Ser  Thr  Gln  Glu  Leu  Phe  Ile  Pro  Asn
305                      310                      315                      320
Ile  Thr  Val  Asn  Asn  Ser  Gly  Ser  Tyr  Thr  Cys  Gln  Ala  His  Asn  Ser
                    325                      330                      335
Asp  Thr  Gly  Leu  Asn  Arg  Thr  Thr  Val  Thr  Thr  Ile  Thr  Val  Tyr  Ala
               340                      345                      350
Glu  Pro  Pro  Lys  Pro  Phe  Ile  Thr  Ser  Asn  Asn  Ser  Asn  Pro  Val  Glu
               355                      360                      365
Asp  Glu  Asp  Ala  Val  Ala  Leu  Thr  Cys  Glu  Pro  Glu  Ile  Gln  Asn  Thr
          370                      375                      380
Thr  Tyr  Leu  Trp  Trp  Val  Asn  Asn  Gln  Ser  Leu  Pro  Val  Ser  Pro  Arg
385                      390                      395                      400
Leu  Gln  Leu  Ser  Asn  Asp  Asn  Arg  Thr  Leu  Thr  Leu  Leu  Ser  Val  Thr
                    405                      410                      415
Arg  Asn  Asp  Val  Gly  Pro  Tyr  Glu  Cys  Gly  Ile  Gln  Asn  Glu  Leu  Ser
               420                      425                      430
```

```
Val  Asp  His  Ser  Asp  Pro  Val  Ile  Leu  Asn  Val  Leu  Tyr  Gly  Pro  Asp
          435                     440                     445

Asp  Pro  Thr  Ile  Ser  Pro  Ser  Tyr  Thr  Tyr  Tyr  Arg  Pro  Gly  Val  Asn
     450                     455                     460

Leu  Ser  Leu  Ser  Cys  His  Ala  Ala  Ser  Asn  Pro  Pro  Ala  Gln  Tyr  Ser
465                      470                     475                          480

Trp  Leu  Ile  Asp  Gly  Asn  Ile  Gln  Gln  His  Thr  Gln  Glu  Leu  Phe  Ile
               485                          490                         495

Ser  Asn  Ile  Thr  Glu  Lys  Asn  Ser  Gly  Leu  Tyr  Thr  Cys  Gln  Ala  Asn
               500                     505                     510

Asn  Ser  Ala  Ser  Gly  His  Ser  Arg  Thr  Thr  Val  Lys  Thr  Ile  Thr  Val
          515                     520                     525

Ser  Ala  Glu  Leu  Pro  Lys  Pro  Ser  Ile  Ser  Ser  Asn  Asn  Ser  Lys  Pro
          530                     535                     540

Val  Glu  Asp  Lys  Asp  Ala  Val  Ala  Phe  Thr  Cys  Glu  Pro  Glu  Ala  Gln
545                           550                     555                     560

Asn  Thr  Thr  Tyr  Leu  Trp  Trp  Val  Asn  Gly  Gln  Ser  Leu  Pro  Val  Ser
               565                     570                     575

Pro  Arg  Leu  Gln  Leu  Ser  Asn  Gly  Asn  Arg  Thr  Leu  Thr  Leu  Phe  Asn
               580                     585                     590

Val  Thr  Arg  Asn  Asp  Ala  Arg  Ala  Tyr  Val  Cys  Gly  Ile  Gln  Asn  Ser
          595                     600                     605

Val  Ser  Ala  Asn  Arg  Ser  Asp  Pro  Val  Thr  Leu  Asp  Val  Leu  Tyr  Gly
     610                     615                     620

Pro  Asp  Thr  Pro  Ile  Ile  Ser  Pro  Pro  Asp  Ser  Ser  Tyr  Leu  Ser  Gly
625                      630                     635                          640

Ala  Asn  Leu  Asn  Leu  Ser  Cys  His  Ser  Ala  Ser  Asn  Pro  Ser  Pro  Gln
               645                     650                     655

Tyr  Ser  Trp  Arg  Ile  Asn  Gly  Ile  Pro  Gln  Gln  His  Thr  Gln  Val  Leu
               660                     665                     670

Phe  Ile  Ala  Lys  Ile  Thr  Pro  Asn  Asn  Asn  Gly  Thr  Tyr  Ala  Cys  Phe
          675                     680                     685

Val  Ser  Asn  Leu  Ala  Thr  Gly  Arg  Asn  Asn  Ser  Ile  Val  Lys  Ser  Ile
     690                     695                     700

Thr  Val  Ser  Ala  Ser  Gly  Thr  Ser  Pro  Gly  Leu  Ser  Ala  Gly  Ala  Thr
705                      710                     715                          720

Val  Gly  Ile  Met  Ile  Gly  Val  Leu  Val  Gly  Val  Ala  Leu  Ile
                    725                     730
```

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CCAGTGAATT CCTAATACGA CTACCTATAG GTTAAAACAG C        41

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:19:

GATGAACCCT CGAGACCCAT TATG  24

(2) INFORMATION FOR SEQ ID NO:20:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:20:

CCACCAAGTA CGTAACCACA TATGG  25

(2) INFORMATION FOR SEQ ID NO:21:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:21:

GTGAGGACTG CTGG  14

(2) INFORMATION FOR SEQ ID NO:22:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:22:

CACCACTGCC CTCGAGAAGC TCACTATTG  29

(2) INFORMATION FOR SEQ ID NO:23:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:23:

CACCACTGCC CTCGAGAAGC TCACTATTG  29

ENCAPSIDATED RECOMBINANT VIRAL NUCLEIC ACID AND METHODS OF MAKING AND USING SAME

RELATED APPLICATIONS

This application is a continuation-in-part application of U.S. Ser. No. 08/087,009, filed Jul. 1, 1993, now abandoned, the contents of which are incorporated herein by reference.

GOVERNMENT SUPPORT

The work described herein was supported by Public Health Service contract (Mucosal Immunology Group) AI 15128, Public Health Service grant AI125005 from the National Institutes of Health, and National Cooperative Vaccine Development Grant (NCVDG) 2 UOI AI28147–06.

BACKGROUND OF THE INVENTION

The present invention relates to methods of encapsidating a recombinant viral nucleic acid having a foreign nucleotide sequence substituted for the nuclcotide sequence of the virus encoding at least a portion of a protein necessary for encapsidation. More particularly, the invention relates to methods and compositions for generating an immune response in a subject by using such a recombinant virus.

Live or attenuated viruses have long been used to stimulate the immune system in a subject. Poliovirus is an attractive candidate system for delivery of antigens to the mucosal immune system because of several biological features inherent to the virus. First, the pathogenesis of the poliovirus is well-studied and the important features identified. The poliovirus is naturally transmitted by an oral-fecal route and is stable in the harsh conditions of the intestinal tract. Primary replication occurs in the oropharynx and gastro-intestinal tract, with subsequent spread to the lymph nodes. Horstmann, D. M. et al. (1959) *JAMA* 170:1–8. Second, the attenuated strains of poliovirus are safe for humans, and are routinely administered to the general population in the form of the Sabin oral vaccine. The incorporation of foreign genes into the attenuated strains would be an attractive feature that should pose no more of a health risk than that associated with administration of the attenuated vaccines alone. Third, the entire poliovirus has been cloned, the nucleic acid sequence determined, and the viral proteins identified. An infectious cDNA is also available for poliovirus which has allowed further genetic manipulation of the virus. Further, previous studies using the attenuated vaccine strains of poliovirus have demonstrated that a long-lasting systemic and mucosal immunity is generated after administration of the vaccine. Sanders, D. Y. and Cramblett, H. G. (1974) *J Ped.* 84:406–408; Melnick, J. (1978) *Bull. World Health Organ.* 56:21–38; Racaniello, V. R. and Baltimore, D. (1981) *Science* 214:916–919; Ogra, P. L. (1984) *Rev. Infect. Dis.* 6:S361–S368.

Recent epidemiological data suggest that worldwide more than seventy percent of infections with human immunodeficiency virus (HIV) are acquired by heterosexual intercourse through mucosal surfaces of the genital tract and rectum. Most HIV vaccines developed to date have been designed to preferentially stimulate the systemic humoral immune system and have relied on immunization with purified, whole human immunodeficiency virus type 1 (HIV-1) and HIV-1 proteins (Haynes, B. F. (May 1993) *Science* 260:1279–1286.), or infection with a recombinant virus or microbe which expresses HIV-1 proteins (McGhee, J. R., and Mestecky, J. (1992) *AIDS Res. Rev.* 2:289–312). A general concern with these studies is that the method of presentation of the HIV-1 antigen to the immune system will not stimulate systemic and mucosal tissues to generate effective immunity at mucosal surfaces. Given the fact that the virus most often encounters a mucosal surface during sexual (vaginal or anal) transmission, a vaccine designed to stimulate both the systemic and mucosal immune systems is essential. McGhee, J. R., and Mestecky, J. (1992) *AIDS Res. Rev.* 2:289–312; Forrest, B. D. (1992) *AIDS Research and Human Retroviruses* 8:1523–1525.

In 1991, a group of researchers reported the construction and characterization of chimeric HIV-1-poliovirus genomes. Choi, W. S. et al. (June 1991) *J. Virol.* 65(6): 2875–2883. Segments of the HIV-1 proviral DNA containing the gag, pol, and env gene were inserted into the poliovirus cDNA so that the translational reading frame was conserved between the HIV-1 and poliovirus genes. The RNAs derived from the in vitro transcription of the genomes, when transfected into cells, replicated and expressed the appropriate HIV-1 protein as a fusion with the poliovirus P1 protein. Choi, W. S. et al. (June 1991) *J. Virol.* 65(6): 2875–2883. However, since the chimeric HIV-1-poliovirus genomes were constructed by replacing poliovirus capsid genes with the HIV-1 gag, pol, or env genes, the chimeric HIV-1-genomes were not capable of encapsidation after introduction into host cells. Choi, W. S. et al. (June 1991) *J. Virol.* 65(6): 2875–2883. Furthermore, attempts to encapsidate the chimeric genome by cotransfection with the poliovirus infectious RNA yielded no evidence of encapsidation. Choi, W. S. et al. (June 1991) *J. Virol.* 65(6): 2875–2883.

In 1992, another group of researchers reported the encapsidation of a poliovirus replicon which incorporated the reporter gene, chloramphenicol acetyltransferase (CAT), in place of the region coding for capsid proteins VP4, VP2, and a portion of VP3 in the genome of poliovirus type 3. Percy, N. et al. (Aug. 1992) *J. Virol.* 66(8): 5040–5046. Encapsidation of the poliovirus replicon was accomplished by first transfecting host cells with the poliovirus replicon and then infecting the host cells with type 3 poliovirus. Percy, N. et al. (Aug. 1992) *J. Virol.* 66(8): 5040, 5044. The formation of the capsid around the poliovirus genome is believed to be the result of interactions between capsid proteins and the poliovirus genome. Therefore, it is likely that the yield of encapsidated viruses obtained by Percy et al. consisted of a mixture of encapsidated poliovirus replicons and encapsidated nucleic acid from the type 3 poliovirus. The encapsidated type 3 poliovirus most likely represents a greater proportion of the encapsidated viruses than does the encapsidated poliovirus replicons. The Percy et al. method of encapsidating a poliovirus replicon is, therefore, an inefficient system for producing encapsidated recombinant poliovirus nucleic acid.

Accordingly, it would be desirable to provide a method of encapsidating a recombinant poliovirus genome which results in a stock of encapsidated viruses substantially composed of the recombinant poliovirus genome. Such a method would enable the efficient production of encapsidated poliovirus nucleic acid for use in compositions for stimulating an immune response to foreign proteins encoded by the recombinant poliovirus genome.

SUMMARY OF THE INVENTION

The present invention pertains to methods of encapsidating a recombinant poliovirus nucleic acid to obtain a yield of encapsidated viruses which substantially comprises encapsidated recombinant poliovirus nucleic acid. The methods of encapsidating a recombinant poliovirus nucleic acid include providing a recombinant poliovirus nucleic acid which lacks the nucleotide sequence encoding at least a portion of a protein necessary for encapsidation and an expression vector lacking an infectious poliovirus genome, the nucleic acid of which encodes at least a portion of one protein necessary for encapsidation; contacting a host cell with the recombinant poliovirus nucleic acid and the expression vector under conditions appropriate for introduction of the recombinant poliovirus nucleic acid and the expression vector into the host cell; and obtaining a yield of encapsidated viruses which substantially comprises an encapsidated recombinant poliovirus nucleic acid. The nucleic acid of the expression vector does not interact with the capsid proteins or portions of capsid proteins which it encodes, thereby allowing encapsidation of the recombinant poliovirus nucleic acid and avoiding encapsidation of the nucleic acid of the expression vector. The invention further pertains to encapsidated recombinant poliovirus nucleic acids produced by the methods of this invention.

In a preferred embodiment, the methods of encapsidating a recombinant poliovirus nucleic acid include providing a recombinant poliovirus nucleic acid in which the VP2 and VP3 genes of the P1 capsid precursor region of the poliovirus genome are replaced by a foreign nucleotide sequence encoding, in an expressible form, a protein or fragment thereof, such as an immunogenic protein or fragment thereof. Examples of immunogenic proteins which can be encoded by the foreign nucleotide sequence include human immunodeficiency virus type 1 proteins and tumor-associated antigens. A host cell, e.g., a mammalian host cell, is then contacted with this recombinant poliovirus nucleic acid and an expression vector lacking an infectious poliovirus genome, such as a vaccinia virus, which encodes the poliovirus P1 capsid precursor protein. Because the expression vector nucleic acid, e.g., vaccinia viral nucleic acid nucleic acid, does not compete with the recombinant poliovirus nucleic acid for the poliovirus capsid proteins, a yield of encapsidated viruses which substantially comprises encapsidated poliovirus nucleic acid is obtained. Further, the resulting encapsidated recombinant poliovirus nucleic acid is able to direct expression of the foreign protein or fragment thereof.

In another preferred embodiment, the methods of encapsidating a recombinant poliovirus nucleic acid include providing a recombinant poliovirus nucleic acid in which the entire P1 capsid precursor region of the poliovirus genome is replaced by a foreign nucleotide sequence encoding, in an expressible form, a protein or fragment thereof, such as an immunogenic protein or fragment thereof. A host cell, e.g., a mammalian host cell, is then contacted with this recombinant poliovirus nucleic acid and an expression vector lacking an infectious poliovirus genome, such as a vaccinia virus, which encodes the poliovirus P1 capsid precursor protein to thereby generate a yield of encapsidated viruses which substantially comprises encapsidated recombinant poliovirus nucleic acid. By these methods of encapsidating recombinant poliovirus nucleic acids, the upper size limit of the foreign nucleotide which can be inserted into the poliovirus nucleic acid is increased, thereby allowing expression of entire proteins, as well as fragments or portions of proteins. The present invention also pertains to encapsidated recombinant poliovirus nucleic acids which lack the entire P1 capsid precursor region.

The present invention further pertains to compositions for stimulating an immune response to an immunogenic protein or fragment thereof and a method for stimulating the immune response by administering the compositions to a subject. The compositions typically contain an encapsidated recombinant poliovirus nucleic acid, in a physiologically acceptable carrier, which encodes an immunogenic protein or fragment thereof and directs expression of the immunogenic protein, or fragment thereof. The compositions are administered to a subject in an amount effective to stimulate an immune response to the immunogenic protein or fragment thereof, e.g., in an amount effective to stimulate the production of antibodies against the immunogenic protein or fragment thereof in the subject.

The invention still further pertains to methods for generating cells that produce a foreign protein or fragment thereof. These methods include contacting host cells with an encapsidated recombinant poliovirus nucleic acid having a foreign nucleotide sequence substituted for the nucleotide sequence which encodes at least a portion of a protein necessary for encapsidating the recombinant poliovirus nucleic acid and an expression vector lacking an infectious poliovirus genome but which encodes and directs expression of at least a portion of a protein necessary for encapsidation of the recombinant poliovirus nucleic acid and directs expression of at least a portion of a protein necessary for encapsidating the recombinant poliovirus nucleic acid and maintaining the cultured host cells under conditions appropriate for introduction of the recombinant poliovirus nucleic acid and the expression vector into the host cells, thereby generating modified cells which produce a foreign protein or fragment thereof. Such modified cells can be reintroduced into the subject from which they were obtained to stimulate an immune response in the subject to the foreign protein or fragment thereof produced by the cells.

BRIEF DESCRIPTION OF THE DRAWINGS

FIGS. 2A, 2B, and 2C show chimeric HIV-1-poliovirus genomes containing regions of the HIV-1 gag orpol gene substituted for the poliovirus P1 gene.

FIG. 5 shows a Northern blot analysis of RNA isolated from a stock of encapsidated recombinant poliovirus nucleic acid.

FIG. 6 shows an SDS-polyacrylamide gel on which the neutralization of the poliovirus nucleic acid encapsidated by VV-P 1 with anti-poliovirus antibodies was analyzed.

FIGS. 7A, 7B, and 7C show SDS-polyacrylamide gels on which poliovirus- and HIV-1-specific protein expression from cells infected with a stock of poliovirus nucleic acid encapsidated by type 1 Sabin poliovirus was analyzed.

FIGS. 14A and 14B show anti-HIV-1-Gag IgA in vaginal lavages from mice after intragastric, intrarectal, and intramuscular administration of an encapsidated recombinant poliovirus nucleic acid encoding and expressing at least a portion of the gag protein of human immunodeficiency virus type 1.

FIGS. 15A, 15B, and 15C show anti-HIV-1-Gag IgA in feces from mice after intragastric, intrarectal, and intramuscular administration of an encapsidated recombinant poliovirus nucleic acid encoding and expressing at least a portion of the gag protein of human immunodeficiency virus type 1.

FIGS. 24A and 24B show expression, in transfected cells, of carcinoembryonic protein encoded by recombinant poliovirus nucleic acid containing the gene for carcinoembryonic antigen.

DETAILED DESCRIPTION OF THE INVENTION

The genome of poliovirus has been cloned and the nucleic acid sequence determined. The genomic RNA molecule is 7433 nucleotides long, polyadenylated at the 3' end and has a small covalently attached viral protein (VPg) at the 5' terminus. Kitamura, N. et al.(1981) *Nature* (London) 291:547–553; Racaniello, V. R. and Baltimore, D. (1981) *Proc. Natl. Acad. Sci.* USA 78:4887–4891. Expression of the poliovirus genome occurs via the translation of a single protein (polyprotein) which is subsequently processed by virus encoded proteases (2A and 3C) to give the mature structural (capsid) and nonstructural proteins. Kitamura, N. et al.(1981) *Nature* (London) 291:547–553; Koch, F. and Koch, G. (1985) The Molecular Biology of Poliovirus (Springer-Verlag, Vienna). Poliovirus replication is catalyzed by the virus-encoded RNA-dependent RNA polymerase ($3D^{pol}$), which copies the genomic RNA to give a complementary RNA molecule, which then serves as a template for further RNA production. Koch, F. and Koch, G. (1985) The Molecular Biology of the Poliovirus (Springer-Verlag, Vienna); Kuhn, R. J. and Wimmer, E. (1987) in D. J. Rowlands et al. (ed.) Molecular Biology of Positive Strand RNA viruses (Academic Press, Ltd., London).

Figure 1:
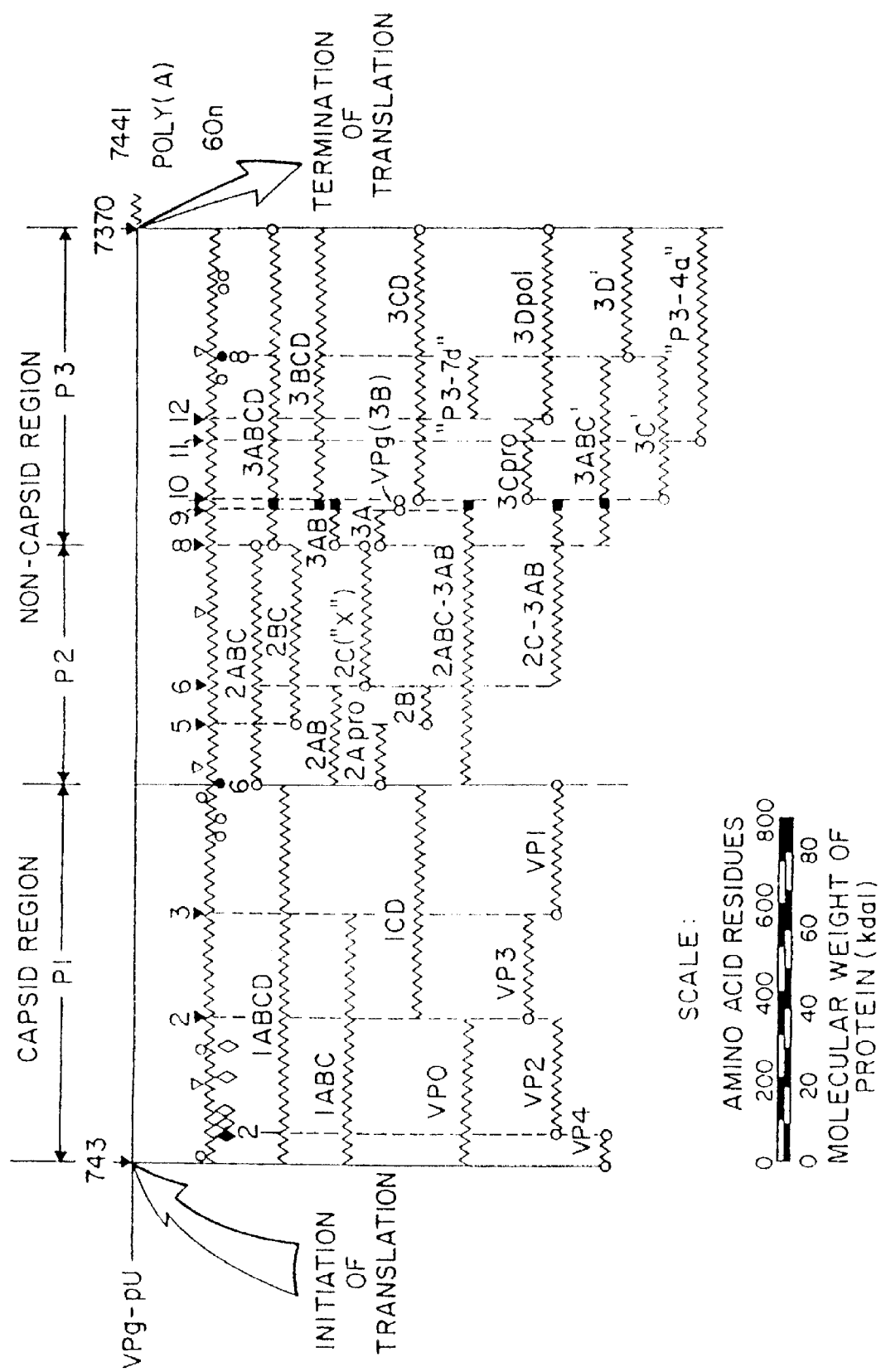
FIG. 1 shows a schematic of the translation and proteolytic processing of the poliovirus polyprotein.

The translation and proteolytic processing of the poliovirus polyprotein is depicted in FIG. 1 which is a figure from Nicklin, M. J. H. et al. (1986) *Bio/Technology* 4:33–42. With reference to the schematic in FIG. 1, the coding region and translation product of poliovirus RNA is divided into three primary regions (P1, P2, and P3), indicated at the top of the figure. The RNA is represented by a solid line and relevant nucleotide numbers are indicated by arrows. Protein products are indicated by waved lines. Cleavage sites are mapped onto the polyprotein (top waved line) as filled symbols; open symbols represent the corresponding sites which are not cleaved. ($\triangledown,\triangledown$) are QG pairs, (0,0) are YG pairs, and ($\Diamond,\Diamond$) are NS pairs. Cleaved sites are numbered according to the occurrence of that amino-acid pair in the translated sequence. Where the amino acid sequence of a terminus of a polypeptide has been determined directly, an open circle has been added to the relevant terminus.

The mature poliovirus proteins arise by a proteolytic cascade which occurs predominantly at Q-G amino acid pairs. Kitamura, N. et al. (1981) *Nature* (London) 291:547–553; Semler, B. L. et al. (1981) *Proc. Natl. Acad Sci.* USA 78:3763–3468; Semler, B. L. et al. (1981) *Virology* 114:589–594; Palmenberg, A. C. (1990) *Ann. Rev. Microbiol.* 44:603–623. A poliovirus-specific protein, $3C^{pro}$, is the protease responsible for the majority of the protease cleavages. Hanecak, R. et al. (1982) *Proc. Natl. Acad. Sci.* USA: 79–3973–3977; Hanecak, R. et al. (1984) *Cell* 37:1063–1073; Nicklin, M. J. H. et al. (1986) *Bio/Technology* 4:33–42; Harris, K. L et al. (1990) *Seminars in Virol.* 1:323–333. A second viral protease, $2A^{pro}$, autocatalytically cleaves from the viral polyprotein to release P1, the capsid precursor. Toyoda, H. et al. (1986) *Cell* 45:761–770.

A second, minor cleavage by 2A$^{pro}$ occurs within the 3D$^{pol}$ to give 3C' and 3D'. Lee, Y. F. and Wimmer, E. (1988) *Virology* 166:404–414. Another role of the 2A$^{pro}$ is the shut off of host cell protein synthesis by inducing the cleavage of a cellular protein required for cap-dependent translation. Bernstein, H. D. et al. (1985) *Mol. Cell Biol.* 5:2913–2923; Krausslich, H. G. et al. (1987) *J. Virol.* 61:2711–2718; Lloyd, R. E. et al. (1988) *J. Virol.* 62:4216–4223.

Previous studies have established that the entire poliovirus genome is not required for RNA replication. Hagino-Yamagishi, K., and Nomoto, A. (1989) *J. Virol.* 63:5386–5392. Naturally occurring defective interfering particles (DIs) of poliovirus have the capacity for replication. Cole, C. N. (1975) *Prog. Med. Virol.* 20:180–207; Kuge, S. et al. (1986) *J. Mol. Biol.* 192:473–487. The common feature of the poliovirus DI genome is a partial deletion of the capsid (P1) region that still maintains the translational reading frame of the single polyprotein through which expression of the entire poliovirus genome occurs. In recent years, the availability of infectious CDNA clones of the poliovirus genome has facilitated further study to define the regions required for RNA replication. Racaniello, V. and Baltimore, D. (1981) *Science* 214:916–919. Specifically, the deletion of 1,782 nucleotides of P1, corresponding to nucleotides 1174 to 2956, resulted in an RNA which can replicate upon transfection into tissue culture cells. Hagino-Yamagishi, K. and Nomoto, A. (1989) *J. Virol* 63:5386–5392.

Early studies identified three poliovirus types based on reactivity to antibodies. Koch, F. and Koch, G. The Molecular Biology of Poliovirus (Springer-Verlag, Vienna 1985). These three serological types, designated as type I, type II, and type III, have been further distinguished as having numerous nucleotide differences in both the non-coding regions and the protein coding regions. All three strains are suitable for use in the present invention. In addition, there are also available attenuated versions of all three strains of poliovirus. These include the Sabin type I, Sabin type II, and Sabin type III attenuated strains of poliovirus that are routinely given to the population in the form of an oral vaccine. These strains can also be used in the present invention.

The recombinant poliovirus nucleic acid of the present invention lacks the nucleotide sequence encoding at least a portion or a protein necessary for encapsidation of the recombinant poliovirus nucleic acid. The nucleotide sequence that is absent from the recombinant poliovirus nucleic acid can be any sequence at least a portion of which encodes at least a portion of a protein necessary for encapsidation, and the lack of which does not interfere with the ability of the poliovirus nucleic acid to replicate or to translate, in the correct reading frame, the single polyprotein through which expression of the entire poliovirus genome occurs. The recombinant poliovirus nucleic acid can be deoxyribonucleic acid (DNA) or ribonucleic acid (RNA). As the poliovirus genome is comprised of RNA which replicates in the absence of a DNA intermediate, it is typically introduced into a cell in the form of RNA. This avoids integration of the poliovirus genome into that of the host cell.

Proteins or portions of proteins necessary for encapsidation of a recombinant poliovirus nucleic acid include, for example, proteins or portions of proteins that are part of the capsid structure. Examples of such proteins are the proteins encoded by the VP1, VP2, VP3, and VP4 genes of the poliovirus P1 capsid precursor region, the Vpg protein, and those proteins that are necessary for proper processing of structural proteins of the capsid structure, such as the proteases responsible for cleaving the viral polyprotein.

The nucleotide sequence lacking from the recombinant poliovirus nucleic acid can be the result of a deletion of poliovirus nucleotide sequences or a deletion of poliovirus nucleotide sequences and insertion of a foreign nucleotide sequence in the place of the deleted sequences. Generally, the nucleotide sequence lacking from the recombinant poliovirus nucleic acid is the P1 region of the poliovirus genome or a portion thereof, which is replaced by a foreign gene. As used herein, the phrase "which lacks the entire P1 capsid precursor region" when used to refer to a recombinant poliovirus nucleic acid is intended to include recombinant poliovirus nucleic acids in which the nucleotide sequence encoding the P1 capsid precursor protein has been deleted or altered such that the proteins which are normally encoded by this nucleotide sequence are not expressed or are expressed in a form which does not function normally. The proteins that are normally encoded by the P1 capsid precursor region of the poliovirus genome include the proteins encoded by the VP 1, VP2, VP3, and VP4 genes. A recombinant poliovirus nucleic acid which lacks the entire P1 capsid precursor region, therefore, either does not include a nucleotide sequence which encodes the proteins encoded by the VP1, VP2, VP3, and VP4 genes or includes a nucleotide sequence which encodes, in unexpressible form or in expressible but not functional form, the proteins encoded by the VP1, VP2, VP3, and VP4 genes. In the present invention, it is specifically contemplated that recombinant poliovirus nucleic acids which lack the entire P1 capsid precursor region can include nucleotide sequences which encode amino acids which are included in the proteins encoded by the VP1, VP2, VP3, and VP4 genes so long as the nucleotide sequence encoding these amino acids of the capsid proteins do not encode the capsid proteins in expressible form or if in expressible form, not functional form. For example, in one embodiment of the invention, the entire P1 capsid precursor region of the poliovirus genome, with the exception of a nucleotide sequence which encodes the first two amino acids (i.e., Met-Gly) of the poliovirus P1 capsid precursor protein, is deleted and replaced with a foreign nucleotide sequence. It is also specifically contemplated that additional nucleotide sequences from the poliovirus genome, e.g., nucleotide sequences which encode amino acid sequences which provide cleavage sites for poliovirus enzymes, e.g., 2A protease, or nucleotide sequences which encode other proteins required for proper processing of a protein encoded by the poliovirus nucleic acid, can be included in recombinant poliovirus nucleic acids which lack the entire P1 capsid precursor region. Additional nucleotide sequences which encode amino acids which are used as spacers within the poliovirus polyprotein to provide an amino acid sequence of the proper length and of the proper sequence for processing of the poliovirus polyprotein can also be included in recombinant poliovirus nucleic acids which lack the entire P1 capsid precursor region.

The foreign nucleotide sequence (or gene) which is substituted for a poliovirus nucleotide sequence preferably is one that encodes, in an expressible form, a foreign protein or fragment thereof. For example, foreign genes that can be inserted into the deleted region of the poliovirus nucleic acid can be those that encode immunogenic proteins. Such immunogenic proteins include, for example, tumor-associated antigens, e.g., human tumor-associated antigens, such as carcinoembryonic antigen (CEA), the ganglioside antigens GM2, GD2, and GD3 from melanoma cells, the antigen Jen CRG from colorectal and lung cancer cells, synthetic peptides of immunoglobulin epitope from B cell malignancies, antigens which are products of oncogenes such as erb, neu, and sis, or any other tumor-associated antigen, antigens obtained from various pathogens, such as hepatitis B surface antigen, influenza virus hemaglutinin and neuraminidase, human immunodeficiency viral proteins, such as gag, pol, and env, respiratory syncycial virus G protein, and the VP4 and VP1 proteins of rotavirus, bacterial antigens such as fragments of tetanus toxin, diphtheria toxin, and cholera toxin, mycobacterium tuberculosis protein antigen B, and urease protein from Heliobactor pylori. In addition, portions of the foreign genes which encode immunogenic proteins can be inserted into the deleted region of the poliovirus nucleic acid. These genes can encode linear polypeptides consisting of B and T cell epitopes. As these are the epitopes with which B and T cells interact, the polypeptides stimulate an immune response. It is also possible to insert chimeric foreign genes into the deleted region of the poliovirus nucleic acid which encode fusion proteins or peptides consisting of both B cell and T cell epitopes. Similarly, any foreign nucleotide sequence encoding an antigen from an infectious agent can be inserted into the deleted region of the poliovirus nucleic acid.

The foreign gene inserted into the deleted region of the poliovirus nucleic acid can also encode, in an expressible form, immunological response modifiers such as interleukins (e.g. interleukin-1, interleukin-2, interleukin-6, etc.), tumor necrosis factor (e.g. tumor necrosis factor-α, tumor necrosis factor-β), or additional cytokines (granulocyte-monocyte colony stimulating factor, interferon-γ). As an expression system for lymphokines or cytokines, the encapsidated poliovirus nucleic acid encoding the lymphokine or cytokine provides for limited expression (by the length of time it takes for the replication of the genome) and can be locally administered to reduce toxic side effects from systemic administration. In addition, genes encoding antisense nucleic acid, such as antisense RNA, or genes encoding ribozymes (RNA molecules with endonuclease or polymerase activities) can be inserted into the deleted region of the poliovirus nucleic acid. The antisense RNA or ribozymes can be used to modulate gene expression or act as anti-viral agents. Genes encoding herpes simplex thymidine kinase, which can be used for tumor therapy, SV40 T antigen, which can be used for cell immortalization, and protein products from herpes simplex virus, e.g., ICP-27, or adeno-associated virus, e.g., Rep, which can be used to complement defective viral genomes can be inserted into the deleted region of the poliovirus nucleic acid.

Foreign genes encoding, in an expressible form, cell surface proteins, secretory proteins, or proteins necessary for proper cellular function which supplement a nonexistent, deficient, or nonfunctional cellular supply of the protein can also be inserted into the deleted region of the poliovirus nucleic acid. The nucleic acid of genes encoding secretory proteins comprises a structural gene encoding the desired protein in a form suitable for processing and secretion by the target cell. For example, the gene can be one that encodes appropriate signal sequences which provide for cellular secretion of the product. The signal sequence can be the natural sequence of the protein or exogenous sequences. In some cases, however, the signal sequence can interfere with the production of the desired protein. In such cases, the nucleotide sequence which encodes the signal sequence of the protein can be removed. See Example 7, below. The structural gene is linked to appropriate genetic regulatory elements required for expression of the gene product by the target cell. These include a promoter and optionally an enhancer element along with the regulatory elements necessary for expression of the gene and secretion of the gene encoded product.

In one embodiment, the foreign genes that are substituted for the capsid genes of the P1 capsid precursor region of the poliovirus genome are the gag (SEQ ID NO: 3; the sequence of the corresponding gag protein is represented by SEQ ID NO: 4), pol (SEQ ID NO: 5; the sequence of the corresponding pol protein is represented by SEQ ID NO: 6), or env (SEQ ID NO: 7; the sequence of the corresponding env protein is represented by SEQ ID NO: 8) genes, or portions thereof, of the human immunodeficiency virus type 1 (HIV-1). See Example 5, below. Portions of these genes are typically inserted in the poliovirus between nucleotides 1174 and 2956. The entire genes are typically inserted in the poliovirus between nucleotides 743 and 3359. The translational reading frame is thus conserved between the HIV-1 genes and the poliovirus genes. The chimeric HIV-1-poliovirus RNA genomes replicate and express the appropriate HIV-1-P1 fusion proteins upon transfection into tissue culture. Choi, W. S. et al. (June 1991) *J. Virol.* 65(6): 2875–2883. In another embodiment, foreign genes encoding tumor-associated antigens or portions thereof, such as carcinoembryonic antigen or portions thereof can be substituted for the capsid genes of the P1 capsid precursor region of the poliovirus genome. See Example 7, below.

Deletion or replacement of the P1 capsid region of the poliovirus genome or a portion thereof results in a poliovirus nucleic acid which is incapable of encapsidating itself. Choi, W. S. et al. (June 1991) *J. Virol.* 65(6): 2875–2883. Typically, capsid proteins or portions thereof mediate viral entry into cells. Therefore, poliovirus nucleic acid which is not enclosed in a capsid enters cells on which there is a poliovirus receptor less efficiently than encapsidated poliovirus nucleic acid. It is preferred, but not required, therefore, that essential capsid proteins from another source be provided for encapsidation and delivery of the foreign genes to cells. In the method of this invention, essential poliovirus capsid proteins are provided by an expression vector which is introduced into the host cell along with the recombinant poliovirus nucleic acid. The expression vectors can be introduced into the host cell prior to, concurrently with, or subsequent to the introduction of the recombinant poliovirus nucleic acid. In an alternative embodiment, nonencapsidated recombinant poliovirus nucleic acid can be delivered directly to target cells, e.g., by direct injection into, for example, muscle cells (see, for example, Acsadi et al. (1991) *Nature* 332:815–818; Wolff et al. (1 990) *Science* 247:1465–1468), or by electroporation, transfection mediated by calcium phosphate, transfection mediated by DEAE-dextran, liposome-mediated transfection (Nicolau et al. (1987) *Meth. Enz.* 149:157–176; Wang and Huang (1987) *Proc. Natl. Acad. Sci. U.S.A* 84:7851–7855; Brigham et al. (1989) *Am. J. Med. Sci.* 298:278; and Gould-Fogerite et al. (1989) *Gene* 84:429–438), or receptor-mediated nucleic acid uptake (see for example Wu, G. and Wu, C. H. (1988) *J. Biol. Chem.* 263:14621; Wilson et al. (1992) *J. Biol. Chem.* 267:963–967; and U.S. Pat. No. 5,166,320), or other methods of delivering naked nucleic acids to target cells, both in vivo and in vitro, known to those of ordinary skill in the art.

In a preferred method of encapsidating the recombinant poliovirus nucleic acid, the expression vector is introduced into the host cell prior to the introduction of the recombinant poliovirus nucleic acid. The introduction of the expression vector into the host cell prior to the introduction of the recombinant poliovirus nucleic acid allows the initial expression of the protein or portion of the protein necessary for encapsidation by the expression vector. Previous studies have established that the replication and expression of the poliovirus genes in cells results in the shutoff of host cell protein synthesis which is accomplished by the $2A^{pro}$ protein of poliovirus. Thus, in order for efficient encapsidation, the expression vector must express the protein necessary for encapsidation. In order for this to occur, the expression vector is generally introduced into the cell prior to the addition of the recombinant poliovirus nucleic acid.

Expression vectors suitable for use in the present invention include plasmids and viruses, the nucleic acids of which encode at least a portion of a protein necessary for encapsidation of the recombinant poliovirus nucleic acid and direct expression of the nucleotide sequence encoding at least a portion of a protein necessary for encapsidation of the recombinant poliovirus nucleic acid. In addition, the nucleic acid of the expression vectors of the present invention does not substantially associate with poliovirus capsid proteins or portions thereof. Therefore, expression vectors of the present invention, when introduced into a host cell along with the recombinant poliovirus nucleic acid, result in a host cell yield of encapsidated viruses which is substantially composed of encapsidated recombinant poliovirus nucleic acid. As used herein, the phrases "substantially composed" or "substantially comprises" when used to refer to a yield of encapsidated recombinant poliovirus nucleic acids is intended to include a yield of encapsidated recombinant poliovirus nucleic acid which is greater than a yield of encapsidated recombinant poliovirus nucleic acid which is generated through the use of an expression vector which encodes poliovirus capsid proteins but also includes an infectious poliovirus genome. Infectious poliovirus genomes can compete with the recombinant poliovirus nucleic acid for poliovirus capsid proteins, thereby decreasing the yield of encapsidated recombinant poliovirus nucleic acid. Generally, the nucleic acid of the expression vector encodes and directs expression of the nucleotide sequence coding for a capsid protein which the recombinant poliovirus nucleic acid is not capable of expressing. For example, the expression vector can encode the entire P1 capsid precursor protein.

Plasmid expression vectors can typically be designed and constructed such that they contain a gene encoding, in an expressible form, a protein or a portion of a protein necessary for encapsidation of the recombinant poliovirus nucleic acid. Generally, construction of such plasmids can be performed using standard methods, such as those described in Sambrook, J. et al. Molecular Cloning: A Laboratory Manual, 2nd edition (CSHL Press, Cold Spring Harbor, N. Y. 1989). A plasmid expression vector which expresses a protein or a portion of a protein necessary for encapsidation of the poliovirus nucleic acid is constructed by first positioning the gene to be inserted (e.g. VP1, VP2, VP3, VP4 or the entire P1 region) after a DNA sequence known to act as a promoter when introduced into cells. The gene to be inserted is typically positioned downstream (3') from the promoter sequence. The promoter sequence consists of a cellular or viral DNA sequence which has been previously demonstrated to attract the necessary host cell components required for initiation of transcription. Examples of such promoter sequences include the long terminal repeat (LTR) regions of Rous Sarcoma Virus, the origin of replication for the SV40 tumor virus (SV4-ori), and the promoter sequence for the CMV (cytomegalovirus) immediate early protein. Plasmids containing these promoter sequences are available from a number of companies which sell molecular biology products (e.g. Promega (Madison, Wis.), Stratagene Cloning Systems (LaJolla, Calif.), and Clontech (Palo Alto, Calif.).

Construction of these plasmid expression vectors typically requires excision of a DNA fragment containing the gene to be inserted and ligation of this DNA fragment into an expression plasmid cut with restriction enzymes that are compatible with those contained on the 5' and 3' ends of the gene to be inserted. Following ligation of the DNA in vitro, the plasmid is transformed into E. coli and the resulting bacteria is plated onto an agar plate containing an appropriate selective antibiotic. The E. coli colonies are then grown and the plasmid DNA characterized for the insertion of the particular gene. To confirm that the gene has been ligated into the plasmid, the DNA sequence of the plasmid containing the insert is determined. The plasmid expression vector can be transfected into tissue culture cells using standard techniques and the protein encoded by the inserted gene expressed.

The conditions under which plasmid expression vectors are introduced into a host cell vary depending on certain factors. These factors include, for example, the size of the nucleic acid of the plasmid, the type of host cell, and the desired efficiency of transfection. There are several methods of introducing the recombinant poliovirus nucleic acid into the host cells which are well-known and commonly employed by those of ordinary skill in the art. These transfection methods include, for example, calcium phosphate-mediated uptake of nucleic acids by a host cell and DEAE-dextran facilitated uptake of nucleic acid by a host cell. Alternatively, nucleic acids can be introduced into cells through electroporation, (Neumann, E. et al. (1982) EMBO J. 1:841–845), which is the transport of nucleic acids directly across a cell membrane by means of an electric current or through the use of cationic liposomes (e.g. lipofection, Gibco/BRL (Gaithersburg, MD)). The methods that are most efficient in each case are typically determined empirically upon consideration of the above factors.

As with plasmid expression vectors, viral expression vectors can be designed and constructed such that they contain a foreign gene encoding a foreign protein or fragment thereof and the regulatory elements necessary for expressing the foreign protein. Viruses suitable for use in the method of this invention include viruses that contain nucleic acid that does not substantially associate with poliovirus capsid proteins. Examples of such viruses include retroviruses, adenoviruses, herpes virus, and Sindbis virus. Retroviruses, upon introduction into a host cell, establish a continuous cell line expressing a foreign protein. Adenoviruses are large DNA viruses which have a host range in human cells similar to that of poliovirus. Sindbis virus is an RNA virus that replicates, like poliovirus, in the cytoplasm of cells and, therefore, offers a convenient system for expressing poliovirus capsid proteins. A preferred viral expression vector is a vaccinia virus. Vaccinia virus is a DNA virus which replicates in the cell cytoplasm and has a similar host range to that of poliovirus. In addition, vaccinia virus can accommodate large amounts of foreign DNA and can replicate efficiently in the same cell in which poliovirus replicates. A preferred nucleotide sequence that is inserted in the vaccinia is the nucleotide sequence encoding and expressing, upon infection of a host cell, the poliovirus P1 capsid precursor polyprotein.

The construction of this vaccinia viral vector is described by Ansardi, D. C. et al. (Apr. 1991) J. Virol. 65(4): 2088–2092. Briefly, type I Mahoney poliovirus cDNA sequences were digested with restriction enzyme Nde I, releasing sequences corresponding to poliovirus nucleotides 3382–6427 from the plasmid and deleting the P2 and much of the P3 encoding regions. Two synthetic oligonucleotides, (5'-TAT-TAG-TAG-ATC-TG (SEQ ID NO: 1)) and 5'-T-ACA-GAT-GTA-CTA-A (SEQ ID NO: 2)) were annealed together and ligated into the Nde I digested DNA. The inserted synthetic sequence is places two translational termination codons (TAG) immediately downstream from the codon for the synthetic P1 carboxy terminal tyrosine residue. Thus, the engineered poliovirus sequences encode an authentic P1 protein with a carboxy terminus identical to that generated when $2A^{pro}$ releases the P1 polyprotein from the nascent poliovirus polypeptide. An additional modification was also generated by the positioning of a Sal I restriction enzyme site at nucleotide 629 of the poliovirus genome. This was accomplished by restriction enzyme digest (BalI) followed by ligation of synthetic Sal I linkers. The DNA fragment containing the poliovirus P1 gene was subcloned into the vaccinia virus recombination plasmid, pSC11. Chackrabarti, S. et at. (1985) *Mol. Cell Biol.* 5:3403–3409. Coexpression of beta-galactosidase provides for visual screening of recombinant virus plaques.

The entry of viral expression vectors into host cells generally requires addition of the virus to the host cell media followed by an incubation period during which the virus enters the cell. Incubation conditions, such as the length of incubation and the temperature under which the incubation is carried out, vary depending on the type of host cell and the type of viral expression vector used. Determination of these parameters is well known to those having ordinary skill in the art. In most cases, the incubation conditions for the infection of cells with viruses typically involves the incubation of the virus in serum-free medium (minimal volume) with the tissue culture cells at 37° C. for a minimum of thirty minutes. For some viruses, such as retroviruses, a compound to facilitate the interaction of the virus with the host cell is added. Examples of such infection facilitators include polybrine and DEAE.

A host cell useful in the present invention is one into which both a recombinant poliovirus nucleic acid and an expression vector can be introduced. Common host cells are mammalian host cells, such as, for example, HeLa cells (ATCC Accession No. CCL 2), HeLa S3 (ATCC Accession No. CCL 2.2), the African Green Monkey cells designated BSC-40 cells, which are derived from BSC-1 cells (ATCC Accession No. CCL 26), and HEp-2 cells (ATCC Accession No. CCL 23). Other useful host cells include chicken cells. Because the recombinant poliovirus nucleic acid is encapsidated prior to serial passage, host cells for such serial passage are preferably permissive for poliovirus replication. Cells that are permissive for poliovirus replication are cells that become infected with the recombinant poliovirus nucleic acid, allow viral nucleic acid replication, expression of viral proteins, and formation of progeny virus particles. In vitro, poliovirus causes the host cell to lyse. However, in vivo the poliovirus may not act in a lytic fashion. Nonpermissive cells can be adapted to become permissive cells, and such cells are intended to be included in the category of host cells which can be used in this invention. For example, the mouse cell line L929, a cell line normally nonpermissive for poliovirus replication, has been adapted to be permissive for poliovirus replication by transfection with the gene encoding the poliovirus receptor. Mendelsohn, C.L. et al. (1989) *Cell* 56:855–865; Mendelsohn, C. L. et al. (1986) *Proc. Natl. Acad. Sci.* USA 83:7845–7849.

The encapsidated recombinant poliovirus nucleic acid of the invention can be used as a vaccine in the form of a composition for stimulating a mucosal as well as a systemic immune response to the foreign protein encoded and expressed by the encapsidated recombinant poliovirus nucleic acid in a subject. Examples of genes encoding proteins that can be inserted into the poliovirus nucleic acid are described above. The mucosal immune response is an important immune response because it offers a first line of defense against infectious agents, such an human immunodeficiency virus, which can enter host cells via mucosal cells. At least a portion of a capsid protein of the encapsidated recombinant poliovirus nucleic acid is supplied by an expression vector which lacks an infectious poliovirus genome. Expression vectors suitable for supplying a capsid protein or a portion thereof are described above. Upon administration of the encapsidated recombinant poliovirus nucleic acid, the subject generally responds to the immunizations by producing both anti-poliovirus antibodies and antibodies to the foreign protein or fragmemt thereof which is expressed by the recombinant poliovirus nucleic acid. The antibodies produced against the foreign protein or fragment thereof provide protection against the disease or detrimental condition caused by the source of the protein or fragment thereof, e.g., virus, bacteria, or tumor cell. The protection against disease or detrimental conditions offered by these antibodies is greater than the protection offered by the subject's immune system absent administration of the recombinant poliovirus nucleic acids of the invention. The recombinant poliovirus nucleic acid, in either its DNA or RNA form, can also be used in a composition for stimulating a systemic and a mucosal immune response in a subject. Administration of the RNA form of the recombinant poliovirus nucleic acid is preferred as it typically does not integrate into the host cell genome.

The encapsidated recombinant poliovirus nucleic acid or the non-encapsidated recombinant poliovirus nucleic acid can be administered to a subject in a physiologically acceptable carrier and in an amount effective to stimulate an immune response to at least the foreign protein or fragment thereof which is encoded (and its expression directed) by the recombinant poliovirus nucleic acid. Typically, a subject is immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject.

Physiologically acceptable carriers suitable for injectable use include sterile aqueous solutions (where water soluble) or dispersions and sterile powders for the extemporaneous preparation of sterile injectable solutions or dispersions. The composition should typically be sterile and fluid to the extent that easy syringability exists. The composition should further be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

Sterile injectable solutions can be prepared by incorporating the encapsidated recombinant poliovirus nucleic acid in the required amount in an appropriate solvent with one or a combination of ingredients enumerated above, as required, followed by filtered sterilization.

When the encapsidated or nonencapsidated recombinant poliovirus nucleic acid is suitably protected, as described above, the protein can be orally administered, for example, with an inert diluent or an assimilable edible carrier. The protein and other ingredients can also be enclosed in a hard or soft shell gelatin capsule, compressed into tablets, or incorporated directly into the individual's diet. For oral therapeutic administration, the active compound can be incorporated with excipients and used in the form of ingestible tablets, buccal tablets, troches, capsules, elixirs, suspensions, syrups, wafers, and the like.

As used herein "physiologically acceptable carrier" includes any and all solvents, dispersion media, coatings, antibacterial and antifungal agents, isotonic and absorption delaying agents, and the like. The use of such media and agents for physiologically active substances is well known in the art. Except insofar as any conventional media or agent is incompatible with the active compound, use thereof in the therapeutic compositions is contemplated.

Subjects who can be treated by the method of this invention include living organisms, e.g., mammals. Typically, subjects who can be treated by the method of this invention are susceptible to diseases, e.g., infectious diseases, cancer, or are susceptible to a detrimental condition which can be treated by the methods described herein, e.g., a detrimental condition resulting from a nonexistent, deficient, or nonfunctional supply of a protein which is normally produced in the subject. Infectious agents which initiate a variety of diseases include microorganisms such as viruses and bacteria. Examples of subjects include humans, monkeys, dogs, cats, rats, and mice.

The amount of the immunogenic composition which can stimulate an immune response in a subject can be determined on an individual basis and is typically based, at least in part, on consideration of the activity of the specific immunogenic composition used. Further, the effective amounts of the immunogenic composition can vary according to the age, sex, and weight of the subject being treated. Thus, an effective amount of the immunogenic composition can be determined by one of ordinary skill in the art employing such factors as described above using no more than routine experimentation.

The immunogenic composition is administered through a route which allows the composition to perform its intended function of stimulating an immune response to the protein encoded by the recombinant poliovirus nucleic acid. Examples of routes of administration which can be used in this method include parenteral (subcutaneous, intravenous, intramuscular, intra-arterial, intraperitoneal, intrathecal, intracardiac, and intrasternal), enteral administration (i.e. administration via the digestive tract, e.g. oral, intragastric, and intrarectal administration), and mucosal administration. It is important to note that the vaccine strains of poliovirus are routinely tested for attenuation by intramuscular and intracerebral injection into monkeys. Thus, it would probably pose no associated health risk if the recombinant poliovirus nucleic acid was given parenterally. Depending on the route of administration, the immunogenic composition can be coated with or in a material to protect it from the natural conditions which can detrimentally affect its ability to perform its intended function.

Cells that produce the encapsidated poliovirus nucleic acids of the present invention can be introduced into a subject, thereby stimulating an immune response to the foreign protein or fragment thereof encoded by the recombinant poliovirus nucleic acid. Generally, the cells that are introduced into the subject are first removed from the subject and contacted ex vivo with both the recombinant poliovirus nucleic acid and an expression vector as described above to generate modified cells that produce the foreign protein or fragment thereof. The modified cells that produce the foreign protein or fragment thereof can then be reintroduced into the subject by, for example, injection or implantation. Examples of cells that can be modified by this method and injected into a subject include peripheral blood mononuclear cells, such as B cells, T cells, monocytes and macrophages. Other cells, such as cutaneous cells and mucosal cells can be modified and implanted into a subject. Methods of introducing the recombinant poliovirus nucleic acid and the expression vectors of the invention are described above.

The invention is further illustrated by the following non-limiting examples. The contents of all references and issued patents cited throughout this application are expressly incorporated herein by reference.

MATERIALS AND METHODS I

The following materials and methods were used in Examples 1, 2, 3, and 4:

All chemicals were purchased from Sigma Chemical Co. (St. Louis, Mo.). Restriction enzymes were obtained from New England Bio-labs (Beverly, Mass.). Tissue culture media was purchased from Gibco/BRL Co. (Gaithersburg, Md.). $^{35}S$ Translabel (methionine-cysteine) and methionine-cysteine-free Dulbecco modified Eagle medium (DMEM) were purchased from ICN Biochemicals (Irvine, Calif.). T7 RNA polymerase was prepared in this laboratory by the method of Grodberg and Dunn. Grodberg, J. and Dunn, J. J. (1988) *J. Bacteriol.* 170:1245–1253.

Tissue culture cells and viruses

HeLa (human cervical carcinoma) and BSC-40 cells (African green monkey kidney cells) were grown in DMEM supplemented with 5% A-γ newborn calf serum and 5% fetal calf serum (complete medium). The stock of the poliovirus type 1 Mahoney used in this study was derived from transfection of an infectious cDNA clone obtained from B. Semler, University of California at Irvine. Semler, B. L. et al. (1984) *Nucleic Acids Res.* 12:5123–5141. The stock of type 1 Sabin poliovirus was obtained from the American Type Culture Collection (ATCC Accession No. VR-192). Wild-type vaccinia virus (wt VV) strain WR and the recombinant vaccinia virus VV-P1, which express the poliovirus P1 capsid precursor protein, have been previously described. Ansardi, D. C. et al. (1991) *J. Virol.* 65:2088–2092. Antisera to HIV-1 reverse transcriptase (RT) and HIV-1 p25/24 Gag (Steimer, K.S. et al. (1986) *Virology* 150:283–290) were obtained through the AIDS Research and Reference Reagent Program (Rockville, Md.). Pooled AIDS patient sera was obtained from the Center for AIDS Research, University of Alabama at Birmingham.

In vitro transcription reaction

The in vitro transcription reactions were performed by using T7 RNA polymerase as described previously. Choi, W. S. et al (1991) *J. Virol.* 65:2875–2883. Prior to in vitro transcription, DNA templates were linearized by restriction enzyme digestion, followed by successive phenol-chloroform (1:1) chloroform extractions and ethanol precipitation. Reaction mixtures (100 μl) contained 1 to 5 μg of linearized DNA template, 5×transcription buffer (100 mM Tris [pH 7.7], 50 mM $MgCl_2$, 20 mM spermidine, 250 mM NaCl), 10 mM dithiotheritol, 2mM each GTP, UTP, ATP, and CTP, 40 U of recombinant RNasin (Promega, Madison, Wis.), and approximately 5μg of purified T7 RNA polymerase per reaction mixture. After 60 min at 37° C., 5% of the in vitro-synthesized RNA was analyzed by agarose gel electrophoresis.

Encapsidation and serial passage of recombinant poliovirus nucleic acids by VV-P1

HeLa cells were infected with 20 PFU of VV-P1 (a recombinant virus which expresses the poliovirus capsid precursor protein P1) or wild type (wt) VV per cell. After 2 hours of infection, the cells were transfected (by using DEAE-dextran [500,000 Da] as a facilitator) with RNA transcribed in vitro from the chimeric HIV-1 poliovirus genomes as previously described. Choi, W. S. et al. (1991) *J. Virol.* 65:2875–2883. The cultures were harvested at 24 hours posttransfection. The cells were lysed with Triton X-100 at a concentration of 1%, treated with RNase A, and clarified by low-speed centrifugation at 14,000×g for 20 min at 4° C. as described previously. Li, G. et al. (1991) *J. Virol.* 65:6714–6723. The supernatants were adjusted to 0.25% sodium dodecyl sulfate (SDS), overlaid on a 30% sucrose cushion (30% sucrose, 30 mM Tris [pH 8.0], 1% Triton X-100, 0.1M NaCl), and centrifuged in a Beckman SW55Ti rotor at 45,000 rpm for 1.5 h. The pelleting procedure described above has been demonstrated to be effective for the removal of infectious vaccinia virus to below detectable levels. The supernatant was discarded, and the pellet was washed by recentrifugation for an additional 1.5 hours in a low salt buffer (30 mM Tris [pH 8.0], 0.1 M NaCl). The pellets were then resuspended in complete DMEM and designated passage 1 of the recombinant poliovirus nucleic acids encapsidated by VV-P 1.

For serial passage of the encapsidated recombinant poliovirus nucleic acids, BSC-40 cells were infected with 20 PFU of VV-P1 per cell. At 2 hours postinfection, the cells were infected with passage 1 of the encapsidated recombinant poliovirus nucleic acids. The cultures were harvested at 24 hours postinfection by three successive freeze-thaws, sonicated, and clarified by centrifugation at 14,000×g for 20 min. The supernatants were then stored at −70° C. or used immediately for additional passages following the same procedure.

Metabolic labeling and immunoprecipitation of viral proteins

To metabolically label viral proteins from infected-transfected or infected cells, the cultures were starved for methionine-cysteine at 6 hours postinfection by incubation in DMEM minus methionine-cysteine for 30 minutes. At the end of this time, $^{35}S$ Translabel was added for an additional hour. Cultures were then processed for immunoprecipitation of viral proteins by lysing the cells with radioimmunoprecipitation assay (RIPA) buffer (150 mM NaCl, 10 mM Tris [pH 7.8], 1% Triton X-100, 1% sodium deoxycholate, 0.2% SDS). Following centrifugation at 14,000 ×g for 10 min to pellet any debris, designated antibodies were added to the supernatants, which were incubated at 4° C. rocking for 24 hours. The immunoprecipitates were collected by addition of 100 μl of protein A-Sepharose (10% [wt/vol] in RIPA buffer). After 1 hour of rocking at room temperature, the protein A-Sepharose beads were collected by brief configuration and washed three times with RIPA buffer. The bound material was eluted by boiling for 5 minutes in gel sample buffer (50 mM Tris [pH 6.8], 5% SDS, 10% glycerol, 0.01% bromophenol blue, 10%βmercaptoethanol). The proteins were analyzed by SDS polyacrylamide gel electrophoresis, and radiolabeled proteins were visualized by fluorography.

Nucleic acid hvbridization

RNA from a stock of recombinant poliovirus nucleic acids encapsidated by VV-P1 was analyzed by Northern (RNA) blotting. Stocks of encapsidated recombinant poliovirus nucleic acids at passage 14 and a high-titer stock of type 1 Mahoney poliovirus were subjected to RNase A treatment and overlaid on 30% sucrose cushion (30% sucrose, 30 mM Tris [pH 8.0], 1% Triton X-100, 0.1M NaCl). The samples were centrifuged in a Beckman SW55Ti rotor at 45,000 rpm for 1.5 h. Pelleted virions were resuspended in TSE buffer (10 mM Tris-HC1 [pH 8.0], 50 mM EDTA) and adjusted to 1% SDS and 1% β-mercaptoethanol as previously described. Rico-Hesse, R. et al. (1987) *Virology* 160:311–322. The resuspended virions were disrupted by extraction three times with phenol-chloroform equilibrated to acidic buffer and one time with chloroform. The extracted RNA was precipitated with 0.2M $LiC1_2$, and 2.5 volumes 100% ethanol. The RNA was denatured and separated on a formaldehyde-agarose gel. The RNA was then transferred from the gel to a nitrocellulose filter by capillary elution (Sambrook, J. et al. (1989) Molecular Cloning: A Laboratory Manual, 2nd edition (Cold Spring Harbor Laboratory Press, N.Y.)) and cross-linked by using a UV Stratalinker (Stratagene, LaJolla, Calif.). The conditions used for prehybridization, hybridization, and washing of RNA immobilized on filters were previously described (Sambrook, J. et al. (1989) Molecular Cloning: A Laboratory Manual, 2nd edition (Cold Spring Harbor Laboratory Press, N.Y.)). Briefly, the blot was prehybridized in hybridization buffer (50% deionized formamide, 6×SSC [1×SSC is 0.15M NaCl plus 0.015 M sodium citrate], 1% SDS, 0.1% Tween 20, 100μg of yeast tRNA per ml). The blot was then incubated in hybridization buffer containing $10^6$ cpm of a [$^{32}P$] UTP-labeled riboprobe complementary to nucleotides 671 to 1174 of the poliovirus genome (Choi, W. S. et al (1991) *J. Virol.* 65:2875–2883) per ml. After hybridization, the blot was washed two times with 0.1×SSC-0.1% SDS at room temperature and one time at 65° C. The blot was then exposed to X-ray film with an intensifying screen.

Neutralization of the recombinant poliovirus nucleic acids encapsidated by VV-P1 using anti-poliovirus antibodies For antibody neutralization, encapsidated recombinant poliovirus nucleic acids at passage 9 were pelleted by ultracentrifugation and resuspended in 250 μl of phosphate-buffered saline (pH 7.0)-0.1% bovine serum albumin. Samples were preincubated with 25 μl of either rabbit anti-poliovirus type 1 Mahoney antisera or preimmune sera per sample at 37° C. for 2 hours. Neutralization experiments were conducted on the basis of the results of preliminary experiments analyzing the capacity of anti-poliovirus antisera to prevent infection of cells by $10^6$ total PFU of poliovirus under the experimental conditions. The preincubated samples were then analyzed for protein expression by infection of BSC-40 cells which were metabolically labeled at 6 hours postinfection followed by immunoprecipitation of viral proteins.

Encapsidation of the recombinant poliovirus nucleic acids by type 1 Sabin poliovirus BSC-40 cells were coinfected with 10 PFU of type 1 Sabin poliovirus and a stock of encapsidated recombinant poliovirus nucleic acids (passage 14) per cell. The infected cells were harvested at 24 hours postinfection by three successive freeze-thaws, sonicated and clarified by centrifugation at 14,000 ×g for 20 minutes as described previously (Li, G., et al. *J. Virol.* 65:6714–6723). Approximately one-half of the supernatant was used for serial passaging by reinfection of BSC-40 cells. After 24 hours, the cultures were harvested as described above, and the procedure was repeated for an additional 10 serial passages.

EXAMPLE 1
EXPRESSION OF RECOMBINANT POLIOVIRUS NUCLEIC ACID IN WHICH THE VP2 AND VP3 REGIONS OF THE POLIOVIRUS GENOME ARE REPLACED WITH A PORTION OF THE HIV-1 GAG OR POL GENES IN CELLS INFECTED WITH AN EXPRESSION VECTOR WHICH EXPRESSES THE POLIOVIRUS CAPSID PRECURSOR PROTEIN P1

Figure 2C:
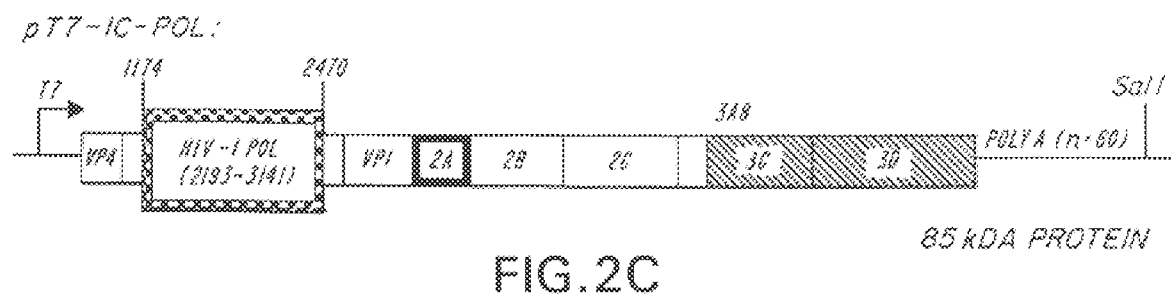

The construction and characterization of recombinant poliovirus nucleic acid in which the HIV-1 gag or pol gene was substituted for VP2 and VP3 regions of the poliovirus P1 protein in the infectious cDNA of poliovirus have previously been described. Choi, W. S. et al (1991) *J. Virol.* 65:2875–2883 (FIG. 2). FIG. 2 shows chimeric HIV-1-poliovirus genomes containing regions of the HIV-1 gag or pol gene substituted for the poliovirus P1 gene. Details of the construction of plasmids pT7-IC-GAG 1 and pT7-IC-POL have been described by Choi et al. and were presented as pT7IC-NheI-gag and pT7IC-NheI-pol, respectively. To construct pT7-IC-GAG 2, a unique SmaI site was created at nucleotide 1580 of the infectious cDNA or poliovirus, and the HIV-1 gag sequences were subcloned between nucleotides 1580 and 2470. Insertion of the HIV-1 genes maintains the translational reading frame with VP4 and VP1. In vitro transcription from these plasmids generates full-length RNA transcripts (linearized with SalI). Transfection of full-length transcripts into HeLa cells results in expression of the poliovirus 3CD protein, a fusion protein between the $3C^{pro}$ and the $3DP^{pol}$ proteins with a molecular mass of 72 kDa. The molecular masses of the HIV-1-P1 fusion proteins are indicated. In previous studies, transfection of these chimeric RNA genomes into type 1 Mahoney poliovirus-infected cells did not result in encapsidation of these RNA genomes (Choi, W. S. et al (1991) *J. Virol.* 65:2875–2883). Under the experimental conditions used, it was possible that the recombinant poliovirus nucleic acid did not efficiently compete with wild-type RNA genomes for capsid proteins. To circumvent this problem, a recombinant vaccinia virus (VV-P1) which expresses the poliovirus capsid precursor protein P1 upon infection was used, since recent studies have shown that in cells coinfected with VV-P1 and poliovirus, P1 protein expressed from VV-P1 can enter the encapsidation pathways of wild type poliovirus.

Figure 3:
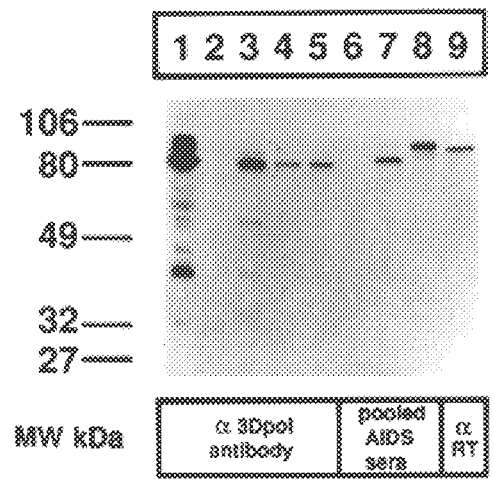
FIG. 3 shows an SDS-polyacrylamide gel on which 3D$^{pol}$ and HIV-1-P1 fusion protein expression from cells infected with VV–P1 and transfected with recombinant poliovirus RNA was analyzed.

Protein expression from the recombinant poliovirus nucleic acid transfected into cells previously infected with the recombinant vaccinia virus VV-P1 was analyzed. (FIG. 3) FIG. 3 shows an analysis of $3D^{pol}$ and HIV-1-P1 fusion protein expression from cells infected with VV-P1 and transfected with recombinant poliovirus nucleic acid RNAs. Cells were infected with VV-P1 at a multiplicity of infection of 20. At 2 hours postinfection, cells were transfected with RNA derived from in vitro transcription of the designated plasmids. Cells were metabolically labeled and cells extracts were incubated with anti-$3D^{pol}$ antibodies (lanes 1 to 5), pooled AIDS patient sera (lanes 6 to 8), or anti-RT antibodies (lane 9), and immunoreactive proteins were analyzed on SDS-polyacrylamide gels. Lanes: 1, cells infected with wild-type poliovirus: 2 and 6, mock-transfected cells: 3 and 7, cells transfected with RNA derived from pT7-IC-GAG 1: 4 and 8, cells transfected with RNA derived from pT7-IC-GAG 2; 5 and 9, cells transfected with RNA derived from pT7-IC-POL. The positions of molecular mass standards are indicated. A protein of molecular mass 72 kDa, corresponding to the 3CD protein of poliovirus, was immunoprecipitated by anti-$3D^{pol}$ antibodies from cells transfected with the recombinant poliovirus RNA but not from mock-transfected cells. Under the same conditions for metabolic labeling, the 3CD protein, which is a fusion protein between the $3C^{pol}$ and $3D^{pol}$ proteins of poliovirus, is predominately detected upon incubation of lysates from poliovirus infected cells with $3D^{pol}$ antisera to determine whether the appropriate HIV-1-P1 fusion proteins were also expressed, the extracts were incubated with pooled AIDS patient sera (gag) or rabbit anti-RT antibodies (Pol). Expression of the HIV-1-Gag-P1 fusion proteins corresponding to the predicted molecular masses 80 and 95 kDa were detected from cells transfected with RNA genomes derived by in vitro transcription of pT7-IC-GAG 1 and pT7-IC-GAG 2, respectively. Similarly, an HIV-1 Pol-P 1 fusion protein of the predicted molecular mass 85 kDa was immunoprecipitated from cells transfected with RNA derived from the in vitro transcription of pT7-IC-POL. These results demonstrate that transfection of the recombinant poliovirus RNA into VV-P1 infected cells results in the expression of appropriate HIV-1-P1 fusion proteins as well as $3D^{pol}$ related proteins.

EXAMPLE 2
ENCAPSIDATION AND SERIAL PASSAGE OF RECOMBINANT POLIOVIRUS NUCLEIC ACID IN WHICH THE VP2 AND VP3 REGIONS OF THE POLIOVIRUS GENOME ARE REPLACED WITH A PORTION OF THE HIV-1 GAG OR POL GENES IN CELLS WITH AN EXPRESSION VECTOR WHICH EXPRESSES THE POLIOVIRUS CAPSID PRECURSOR PROTEIN P1

Figure 4A:
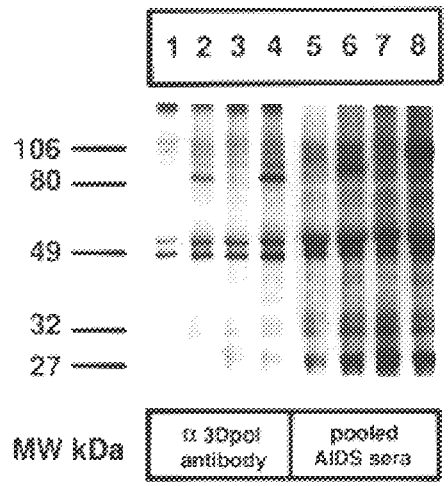
FIGS. 4A, 4B, and 4C show SDS-polyacrylamide gels on which poliovirus- and HIV-1-specific protein expression from cells infected with recombinant poliovirus RNA which were encapsidated and serially passaged with capsid proteins provided by VV-P1 were analyzed.
Figure 4B:
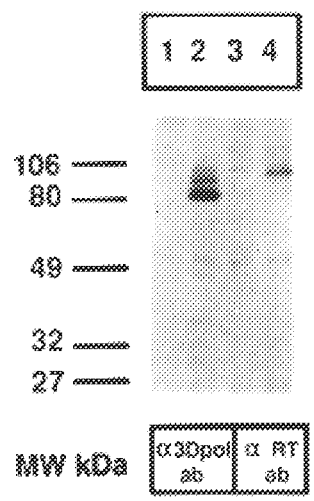

In order to determine whether transfection of the recombinant poliovirus nucleic acids encoding the HIV-1 gag and pol genes into VV-P1 infected cells would result in encapsidation of the recombinant poliovirus nucleic acid, the recombinant poliovirus RNA's were transfected into either VV-P1 or wt VV-infected cells, and the encapsidation genomes were isolated as described in Materials and Methods I. The pelleted material was then used to reinfect cells. This procedure was followed by metabolic labeling of viral proteins and incubation with anti-$3D^{pol}$ or HIV-1-antisera (FIGS. 4A and 4B). FIGS. 4A and 4B show an analysis of poliovirus- and HIV-1-specific protein expression from cells infected with recombinant poliovirus nucleic acids which were encapsidated and serially passaged with capsid proteins provided by VV-P1. Cells were infected with VV-P1 or wt VV at a multiplicity of infection of 20 and transfected with RNA derived from in vitro transcription of the designated plasmids. The cells were harvested for isolation of encapsidated genomes as described in Materials and Methods 1. The pelleted material was used to reinfect cells, which were metabolically labeled, and cell lysates were incubated with the designated antibodies. Immunoreactive proteins were analyzed on SDS-polyacrylamide gels. FIG. 4A: Lanes: 1 and 5, cells infected with pelleted material derived from cells infected with wt VV and transfected with RNA derived from pT7-IC-GAG 1; 2 and 6, cells infected with pelleted material derived from cells infected with VV-P1 and transfected with RNA derived from pT7-IC-GAG 1; 3 and 7, cells infected with pelleted material derived from cells infected with wt VV and transfected with RNA derived from pT7-IC-GAG 2; 4 and 8, cells infected with pelleted material derived from cells infected with VV-P1 and transfected with RNA derived from pT7-IC-GAG2. FIG. 4B: Lanes: 1 and 3, cells infected with pelleted material derived from cells infected with wt VV and transfected with RNA derived from pT7-IC-POL; 2 and 4, cells infected with pelleted material derived from cells infected with VV-P 1 and transfected with RNA derived from PT7-IC-POL.

The poliovirus 3CD protein was immunoprecipitated from cells infected with pelleted material derived from transfection of the recombinant poliovirus RNA into VV-P1 infected cells. The molecular masses of the HIV-1-P1 fusion proteins immunoprecipitated from the infected cells were consistent with the predicted molecular masses and those observed from expression of the recombinant poliovirus nucleic acid in transfected cells (FIG. 2). No 3D$^{pol}$ or HIV-1-P1 proteins were detected from cells infected with material derived from transfection of the chimeric genomes into wt VV-infected cells, demonstrating a requirement for the poliovirus P1 protein for encapsidation of the recombinant poliovirus nucleic acid.

Figure 4C:
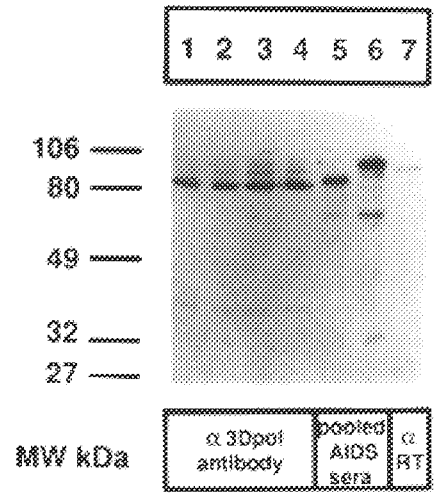

To determine whether the encapsidated recombinant poliovirus nucleic acid could be serially passaged, passage 1 stock of the encapsidated recombinant poliovirus nucleic acid was used to infect cells that had been previously infected with VV-P 1. After 24 hours, the encapsidated recombinant poliovirus nucleic acids were isolated as described in Materials and Methods I and subsequently used to reinfect cells which had been previously infected with VV-P1; this procedure was repeated for an additional nine passages. By convention the stocks of serially passaged recombinant poliovirus RNA are referred to as vIC-GAG 1, vIC-GAG 2, or vIC-POL. Cells were infected with passage 9 material and metabolically labeled and the lysates were incubated with antisera to poliovirus 3D$^{pol}$ protein or antibodies to HIV-1 proteins (FIG. 4C). In FIG. 4C, stocks of the encapsidated recombinant poliovirus nucleic acids were also used to infect cells which had been previously infected with VV-P1 for serial passage of the encapsidated genomes as described in Materials and Methods I. Cells were infected with serially passaged stocks of recombinant poliovirus nucleic acids at passage 9 and metabolically labeled, and cell extracts were incubated with the designated antibodies (ab). Immunoreactive proteins were analyzed on SDS-polyacrylamide gels. Lanes: 1, cells infected with wild-type poliovirus; 2 and 5, cells infected with vIC-GAG 1; 3 and 6, Cells infected with vIC-GAG2; 4 and 7, cells infected with vIC-POL. The positions of molecular mass standards are indicated.

The poliovirus 3CD protein was immunoprecipitated from cells infected with poliovirus and the encapsidated recombinant poliovirus nucleic acids. The HIV-1-Gag-P1 and HIV-1-Pol-P1 fusion proteins were also immunoprecipitated from cells infected with the serially passaged recombinant poliovirus nucleic acids. In contrast, no immunoreactive proteins were detected from cells which were infected with VV-P1 alone and immunoprecipitated with the same antisera (FIG. 3).

To determine whether the encapsidated recombinant poliovirus nucleic acids had undergone any significant deletion of genome size as a result of serial passage with VV-P1, RNA isolated from vIC-GAG 1 at passage 14 was analyzed by Northern blotting (FIG. 5). FIG. 5 shows a Northern blot analysis of RNA isolated from a stock of encapsidated recombinant poliovirus nucleic acids. Virions were isolated by ultracentrifugation from a stock of vIC-GAG 1 at passage 14 and from type 1 Mahoney poliovirus. The isolated virions were disrupted, and the RNA was precipitated, separated in a formaldehyde-agarose gel, and transferred to nitrocellulose. Lanes: 1, RNA isolated from vIC-GAG 1 stock; 2, RNA isolated from poliovirions. Note that the exposure time for the sample in lane 1 of the gel was six times longer than that for lane 2.

For these studies, a riboprobe complementary to nucleotides 671 to 1174 of poliovirus, present in the HIV-1-poliovirus chimeric genomes, was used. RNA isolated from vIC-GAG 1 was compared with RNA isolated from type 1 Mahoney poliovirions. The migration of the RNA isolated from vIC-GAG 1 was slightly faster than that of the wild-type poliovirus RNA, consistent with the predicted 7.0-kb size for RNA from pT7-IC-GAG 1 versus the 7.5-kb size for wild-type poliovirus RNA. Furthermore, a single predominant RNA species from vIC-GAG 1 was detected, indicating that no significant deletions of the RNA had occurred during the serial passages.

Antibody neutralization of recombinant poliovirus nucleic acid encapsidated by VV-P1

To confirm that the recombinant poliovirus nucleic acid RNA passaged with VV-P1 was encapsidated in poliovirions, the capacity of poliovirus-specific antisera to prevent expression of the HIV-1 P1 fusion proteins and poliovirus 3CD protein was analyzed. The results of this experiment are important to exclude the possibility that the recombinant poliovirus nucleic acids were being passaged by inclusion into VV-P1 rather than poliovirions. For these studies, passage 9 material of vIC-GAG 1 was preincubated with preimmune type 1 poliovirus antisera as described in Materials and Methods I. After incubation, the samples were used to infect cells, which were then metabolically labeled, and cell lysates were analyzed for expression of poliovirus- and HIV-1 specific proteins after incubation with anti-3D$^{pol}$ antisera and pooled AIDS patient sera, respectively (FIG. 6). FIG. 6 shows neutralization of recombinant poliovirus nucleic acids encapsidated by VV-P1 with anti-poliovirus antibodies. Cells were infected with a passage 9 stock of vIC-GAG 1 that had been preincubated with anti-poliovirus type 1 antisera or preimmune sera as described in Materials and Methods I. Infected cells were metabolically labeled, cell lysates were incubated with anti-3D$^{pol}$ antibodies (lanes 1 to 3) or pooled AIDS patient sera (lanes 4 and 5), and immunoreactive proteins were analyzed on SDS-polyacrylamide gels. Lanes: 1, cells infected with wild-type poliovirus (no neutralization); 2 and 4, cells infected with vIC-GAG 1 which had been preincubated with preimmune sera: 3 and 5, cells infected with vIC-GAG 1 which had been preincubated with anti-poliovirus type 1 antisera. The positions of molecular mass standards are indicated.

No expression of the poliovirus 3CD or HIV-1-Gag-P1 fusion protein was detected from cells infected with vIC-GAG 1 which had been preincubated with the anti-poliovirus antibodies. Expression of 3CD protein and HIV-1 Gag-P1 fusion protein was readily detected from cells infected with vIC-GAG 1 which had been preincubated with normal rabbit serum (preimmune). These results demonstrate that the recombinant poliovirus nucleic acids were encapsidated by P1 protein provided in trans by VV-P1 which could be neutralized by anti-poliovirus antibodies.

Encapsidation of serially passaged recombinant poliovirus nucleic acids by poliovirus To determine whether the recombinant poliovirus nucleic acid genomes could be encapsidated by P1 protein provided in trans from wild-type poliovirus, cells were coinfected with type 1 Sabin poliovirus and passage 14 stock of vIC-GAG 1. After 24 hours, the coinfected cells were harvested as described in Materials and Methods I, and the extracted material was serially passaged 10 additional times at a high multiplicity of infection. Cells were infected with passage 10 material of vIC-GAG 1 and type 1 Sabin poliovirus and metabolically labeled, and cell extracts were incubated with antibodies to type 1 Sabin poliovirus (FIG. 7A), pooled sera from AIDS patients (FIG. 7B), and anti-p24 antibodies (FIG. 7C) and the immunoreactive proteins were analyzed on SDS polyacrylamide gels. Lanes: 1, cells infected with type 1 Sabin poliovirus alone; 2, cells infected with material derived from passage 10 of vIC-GAG 1 and type 1 Sabin poliovirus. The positions of relevant proteins are indicated.

Poliovirus capsid proteins were detected from cells infected with type 1 Sabin poliovirus alone and from cells infected with material derived from passaging vIC-GAG 1 with type 1 Sabin poliovirus. No HIV-1 specific proteins were detected from cells infected with type 1 Sabin poliovirus alone. A slight cross-reactivity of the HIV-1-Gag-P1 fusion protein with anti-poliovirus antisera was detected in extracts of cells infected with material derived from passaging vIC-GAG 1 with type 1 Sabin poliovirus (FIG. 7A). Although the HIV-1-Gag-P1 fusion protein was clearly detected from cells with type 1 Sabin poliovirus after incubation with pooled AIDS patient sera, some cross-reactivity of the poliovirus capsid proteins were also detected (FIG. 7B). To confirm that the HIV-1-Gag-P1 fusion protein had been immunoprecipitated from extracts of cells infected with material derived from passaging vIC-Gag 1 with type 1 Sabin poliovirus, the extracts were incubated with rabbit anti-p24 antiserum (FIG. 7C). Again, detection of the HIV-1-Gag-P1 fusion protein was evident from cells infected with material derived from passaging vIC-GAG 1 with type 1 Sabin poliovirus but not from cells infected with type 1 Sabin alone. Furthermore, HIV-1-Gap-P1 fusion protein expression was detected after each serial passage (1 to 10) of vIC-GAG 1 with type 1 Sabin poliovirus. These results demonstrate that the chimeric recombinant poliovirus nucleic acids can be encapsidated by P1 protein provided in trans from type 1 Sabin poliovirus under the appropriate experimental conditions and are stable upon serial passage.

EXAMPLE 3
PRODUCTION OF ANTI-POLIOVIRUS AND ANTI-GAG ANTIBODIES IN MICE IMMUNIZED WITH ENCAPSIDATED RECOMBINANT POLIOVIRUS NUCLEIC ACID CONTAINING A PORTION OF THE HIV-1 GAG GENE

The construction and characterization of chimeric HIV-1 poliovirus nucleic acid in which the HIV-1 gag gene was substituted for VP2 and VP3 regions of the poliovirus P1 protein in the infectious cDNA of poliovirus was performed as described previously. Choi, W. S. et al. (1991) *J. Virol.* 65:2875–2883. To evaluate both qualitatively and quantitatively the immune responses against HIV-1 gag expressed from recombinant poliovirus nucleic acid, BALB/c mice (5 animals in each of three groups) were immunized by parenteral (intramuscular), oral (intragastric) or intrarectal routes. The doses were $2.5 \times 10^5$ virus PFU poliovirus/mouse for systemic immunization (intramuscular) and $2.5 \times 10^6$ PFU poliovirus/mouse for oral immunization. It is important to note that the titer refers only to the type II Lansing in the virus preparation, since the encapsidated recombinant poliovirus nucleic acid alone does not form plaques due to deletion of the P1 capsids. For oral immunization, the antigen was resuspended in 0.5 ml of RPMI 1640 and administered by means of an animal feeding tube (Moldoveanu et al. (1993) *J. Infect. Dis.* 167:84–90). Intrarectal immunization was accomplished by application of a small dose of virus in solution (10 $\mu$l/mouse intrarectally). Serum, saliva, fecal extract and vaginal lavage were collected before immunization, and two weeks after the initial dose of the virus.

Collection of Biological Fluids

Biological fluids were collected two weeks after the primary immunization, and one week after the secondary immunization. The methods for obtaining biological fluids are as follows:

Blood was collected from the tail vein with heparinized glass capillary tubes before and at selected times after immunization. The blood was centrifuged and plasma collected and stored at −70° C.

Stimulated saliva was collected with capillary tubes after injection with carbamyl-choline (1–2$\mu$g/mouse). Two $\mu$g each of soybean trypsin inhibitor and phenylmethylsulfonyl fluoride (PMSF) was added to the sample followed by clarification by centrifugation at 800×g for 15 minutes. Sodium azide (0.1% final concentration) and FCS (1% final concentration) was added after clarification and the sample stored at −70° C. until the assay.

Vaginal lavages were performed in mice by applying approximately 50 $\mu$l sterile PBS into the vagina and then aspirating the outcoming fluid.

Intestinal lavages were performed according to the methods previously described by Elson et al. (Elson, C. O. et al. (1984) *J. Immunol. Meth.* 67:101–108). For those studies, four doses of 0.5 ml lavage solution (isoosmotic for mouse gastrointestinal secretion) was administered at 15 minute intervals using an intubation needle. Fifteen minutes after the last dose of lavage, 0.1 $\mu$g of polycarbine was administered by intraperitoneal injection to the anesthetized mouse. Over the next 10 to 15 minutes the discharge of intestinal contents was collected into a petri dish containing a 5 ml solution of 0.1 mg/ml trypsin soybean inhibitor and 5 mM EDTA. The solid material was removed by centrifugation (650 ×g for 10 minutes at 4° C.) and the supernatant collected. Thirty $\mu$l of 100 mM PMSF was then added followed by further clarification at 27,000 ×g for 20 minutes at 4° C. An aliquot of 10$\mu$l of 0.1% sodium azide and 10% fetal calf serum was added before storage at −70° C.

Fecal Extract was prepared as previously described (Keller, R., and Dwyer, J. E. (1968) *J. Immunol.* 101: 192–202).

Enzyme-Linked Immunoabsorbant Assay

An ELISA was used for determining antigen-specific antibodies as well as for total levels of immunoglobulins. The assay was performed in 96-well polystyrene microtiter plates (Dynatech, Alexandria, Va.). For coating, purified poliovirus (1 $\mu$g/well) or HIV specific proteins, or solid phase adsorbed, and affinity-purified polyclonal goat IgG antibodies specific for mouse IgG, IgA or IgM (Southern Biotechnology Associates, Birmingham, Ala. (SBA)(1 $\mu$g/well)) were employed. Dilutions of serum or secretions were incubated overnight at 4° C. on the coated and blocked ELISA plates and the bound immunoglobulins were detected with horseradish peroxidase-labeled goat IgG against mouse Ig, IgA, IgG, or IgM (SBA). At the end of the incubation time (3 hours at 37° C.), the peroxidase substrate 2,2-azino bis. (3-ethylbenzthiazoline) sulfonic acid (ABTS) (Sigma, St. Louis, Mo.) in citrate buffer pH 4.2 containing 0.0075% $H_2O_2$ was added. The color developed was measured in a Titertek Multiscan photometer (Molecular Devices, Palo Alto, Calif.) at 414 nm. To calibrate the total level of mouse IgA, IgG, IgM levels, purified mouse myeloma proteins served as standards. For antigen-specific ELISA, the optical densities were converted to ELISA units, using calibration curves obtained from optical density values obtained from reference pools of sera or secretions. The calibration curves were constructed using a computer program on either 4-parameter logistic or weighed logit-log models. End point titration values were an alternative way of expressing the results. The fold increase values were calculated by dividing post-immunization by pre-immunization values expressed in ELISA units.

Anti-poliovirus antibodies

Figure 8A:
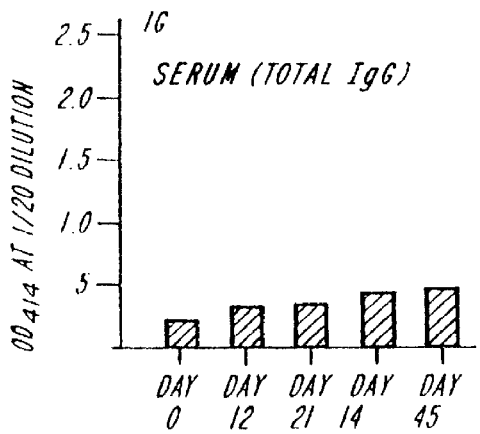
FIGS. 8A, 8B, and 8C show total anti-poliovirus IgG levels in serum from mice after intragastric, intrarectal, and intramuscular administration of an encapsidated recombinant poliovirus nucleic acid encoding and expressing at least a portion of the gag protein of human immunodeficiency virus type 1.
Figure 8B:
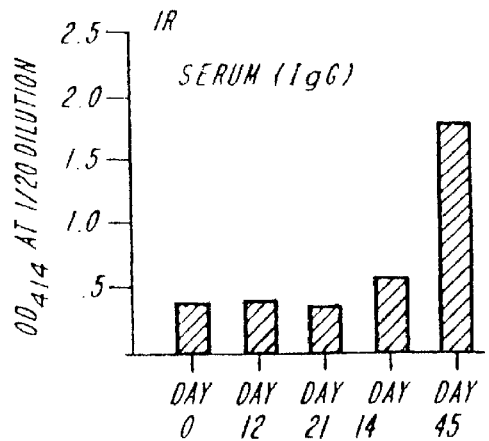
Figure 8C:
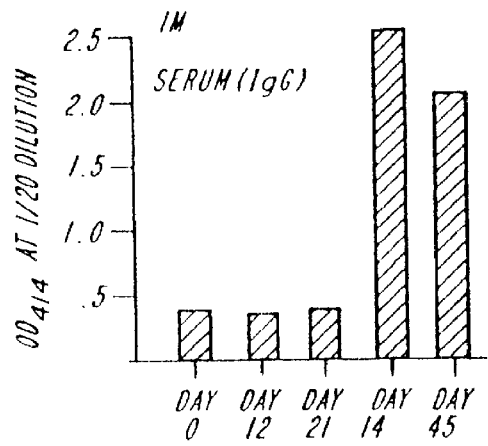

The levels of anti-poliovirus antibodies were determined by ELISA at Day 0 (pre-immune), Days 12, and 21 post immunization. A second administration of encapsidated recombinant poliovirus nucleic acid was given by the same route at day 21, and samples were collected 14 days post to second booster and 45 days post second booster. FIGS. 8A, 8B, and 8C show serum anti-poliovirus antibodies (designated total IgG, representing predominantly IgG, with minor contribution of IgM and IgA) for animals immunized via the intragastric, intrarectal, or intramuscular route. The samples from each of the 5 animals within the group were pooled, and the ELISA was used to determine the amounts of anti-poliovirus antibodies at a 1:20 dilution. A very slight increase in the anti-poliovirus antibodies present in the serum of mice immunized via the intragastric route was observed at Day 45 post booster immunization when compared to the pre-immune levels at Day 0. A clear increase in the serum anti-poliovirus antibodies was observed in the animals immunized via the intragastric or intramuscular route at Day 14 and Day 45 post booster immunization. The levels at Day 14 and 45 post booster immunization were approximately 5-fold over that observed for the background levels at Day 0.

Figure 9A:
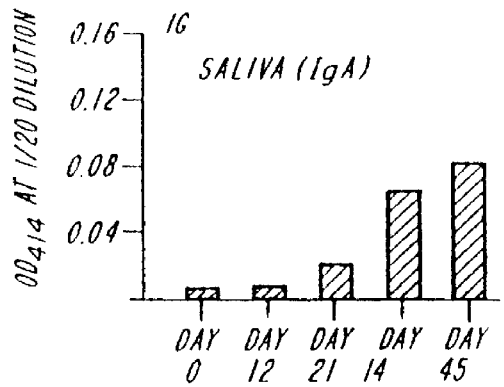
FIGS. 9A, 9B, and 9C show anti-poliovirus IgA levels in saliva from mice after intragastric, intrarectal, and intramuscular administration of an encapsidated recombinant poliovirus nucleic acid encoding and expressing at least a portion of the gag protein of human immunodeficiency virus type 1.
Figure 9B:
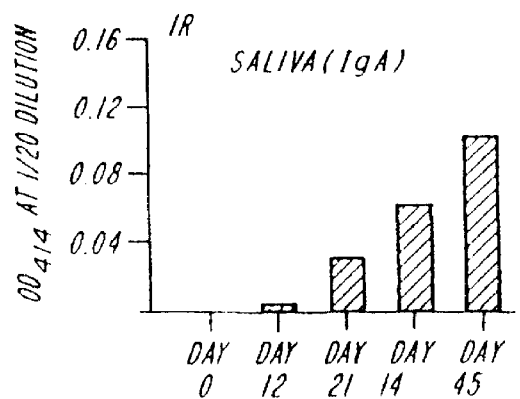
Figure 9C:
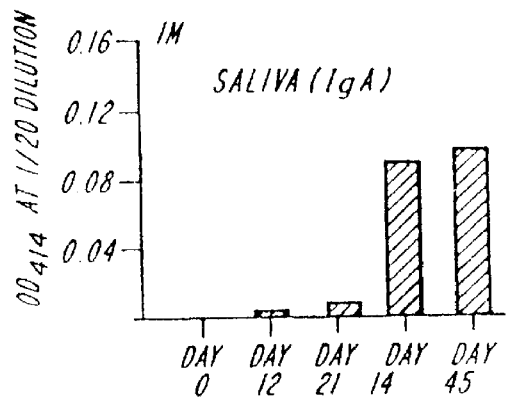
Figure 10A:
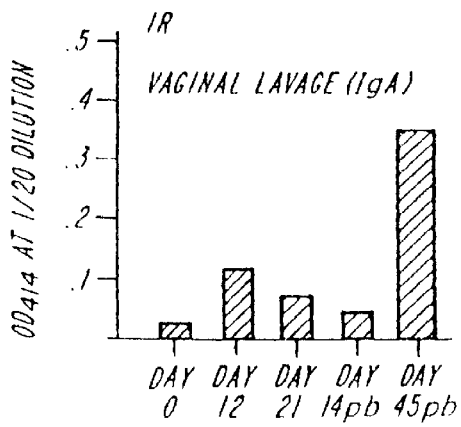
FIGS. 10A and 10B show anti-poliovirus IgA in vaginal lavages after intrarectal, and intramuscular administration of an encapsidated recombinant poliovirus nucleic acid encoding and expressing at least a portion of the gag protein of human immunodeficiency virus type 1.
Figure 10B:
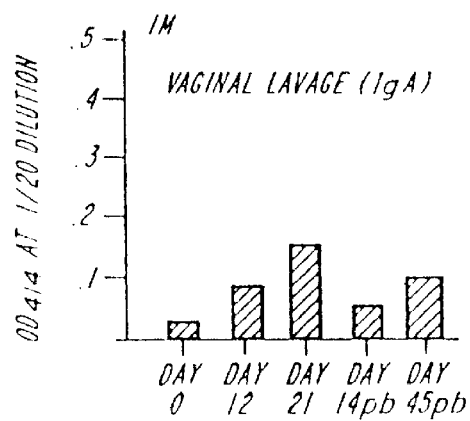
Figure 11A:
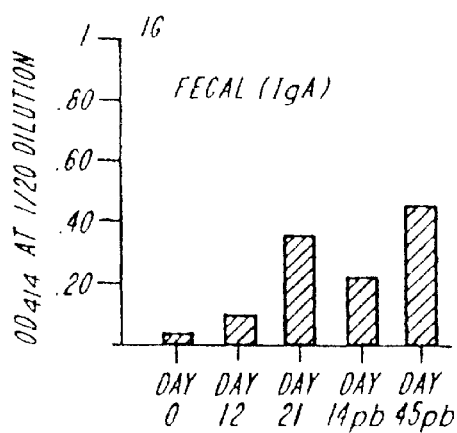
FIGS. 11A, 11B, and 11C show anti-poliovirus IgA in feces from mice after intragastric, intrarectal, and intramuscular administration of an encapsidated recombinant poliovirus nucleic acid encoding and expressing at least a portion of the gag protein of human immunodeficiency virus type 1.
Figure 11B:
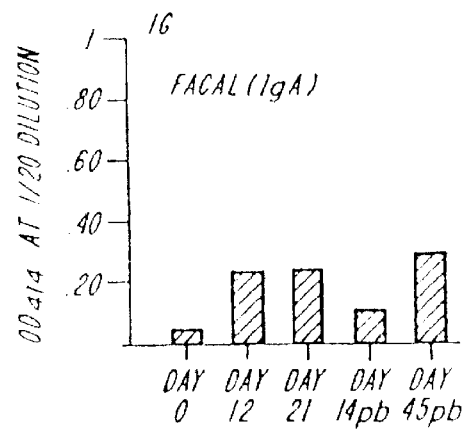
Figure 11C:
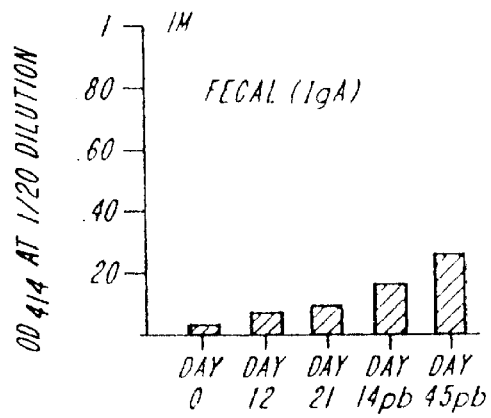
Figure 12A:
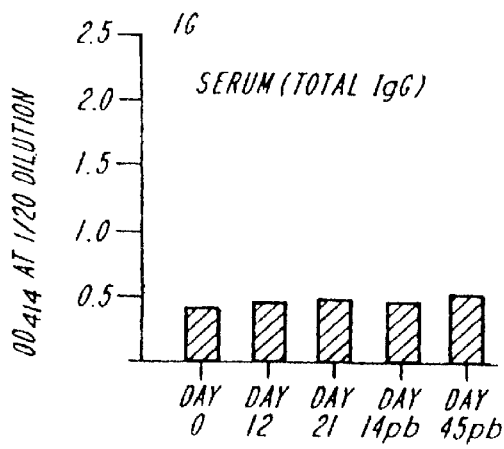
FIGS. 12A, 12B, and 12C show anti-HIV-1-Gag IgG in serum from mice after intragastric, intrarectal, and intramuscular administration of an encapsidated recombinant poliovirus nucleic acid encoding and expressing at least a portion of the gag protein of human immunodeficiency virus type 1.
Figure 12B:
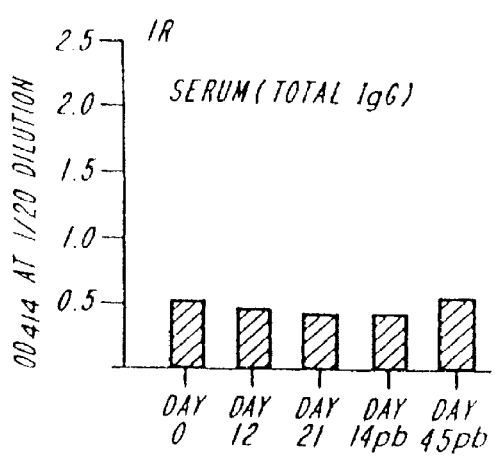
Figure 12C:
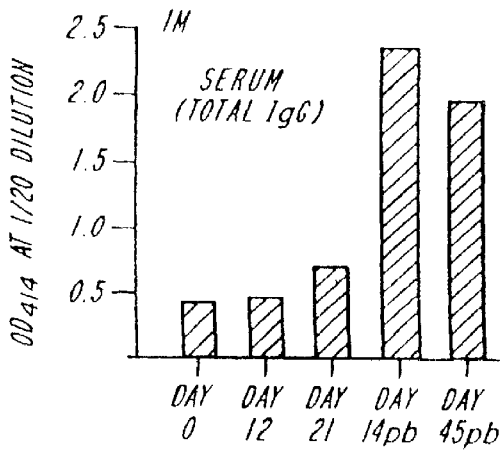
Figure 13A:
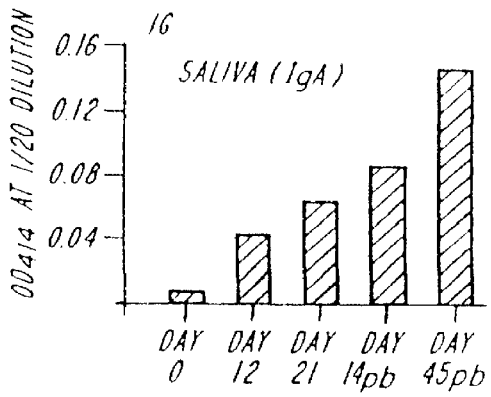
FIGS. 13A, 13B, and 13C show anti-HIV-1-Gag IgA in saliva from mice after intragastric, intrarectal, and intramuscular administration of an encapsidated recombinant poliovirus nucleic acid encoding and expressing at least a portion of the gag protein of human immunodeficiency virus type 1.
Figure 13B:
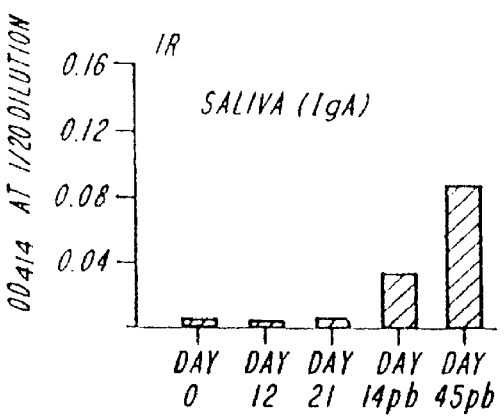
Figure 13C:
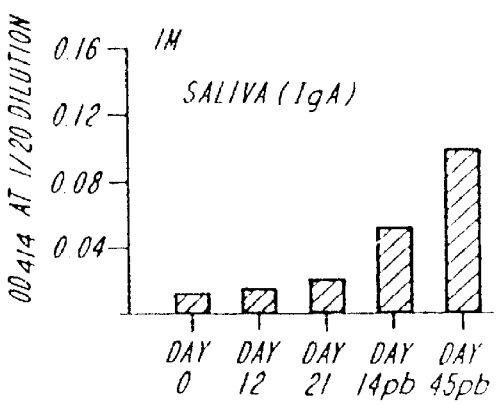
Figure 16:
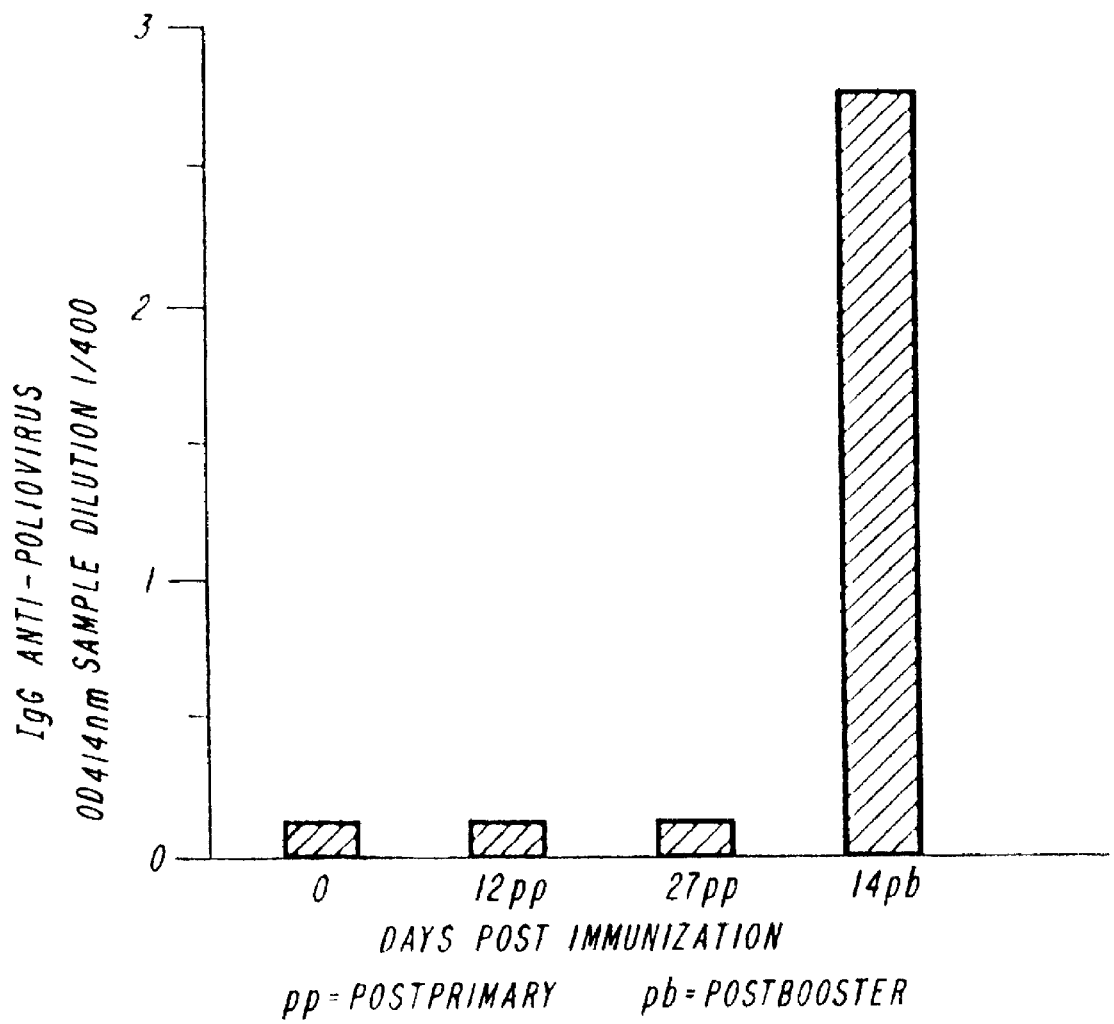
FIG. 16 shows anti-poliovirus IgG from serum of a pigtail macaque after intrarectal administration of an encapsidated recombinant poliovirus nucleic acid encoding and expressing at least a portion of the gag protein of human immunodeficiency virus type 1.
Figure 17A:
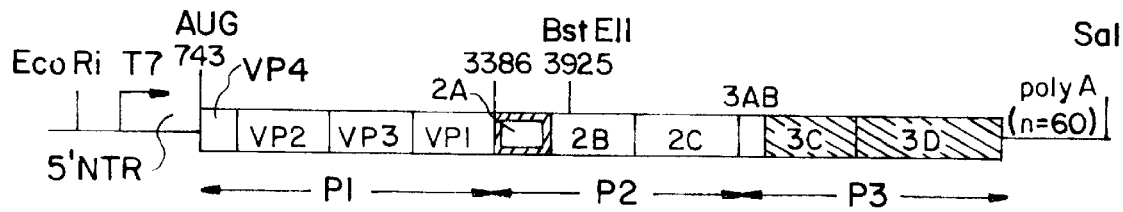
FIGS. 17A, 17B, and 17C show recombinant poliovirus nucleic acids which contain the complete gag gene of HIV-1.
Figure 17B:
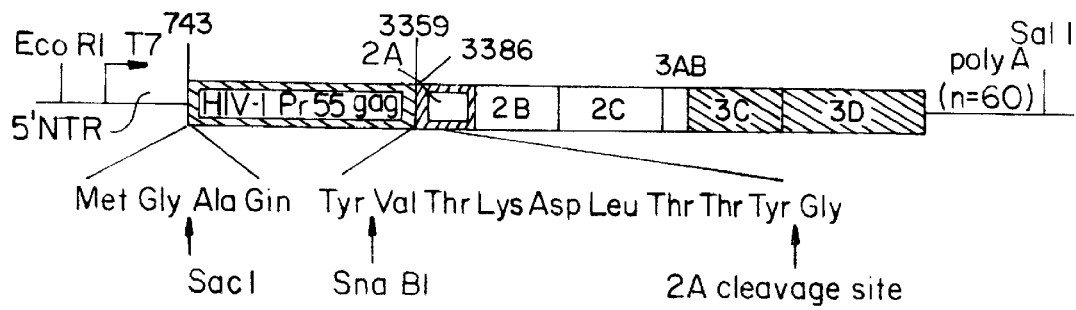
Figure 17C:
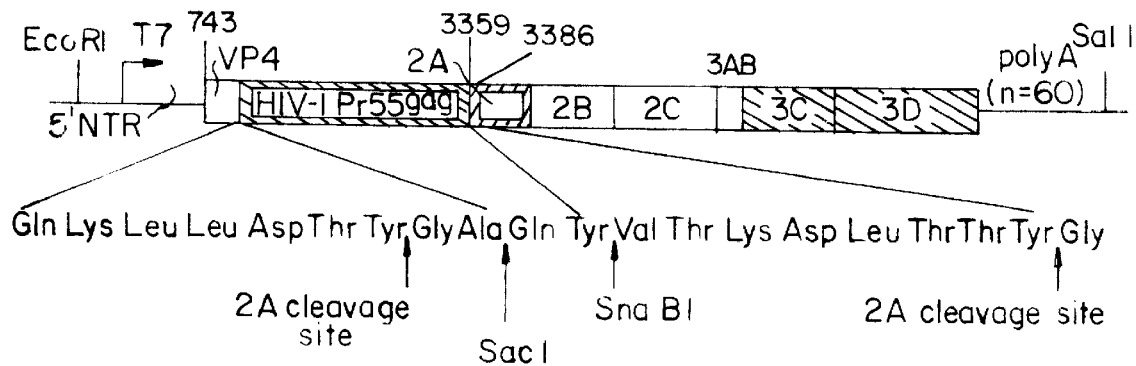
Figure 18A:
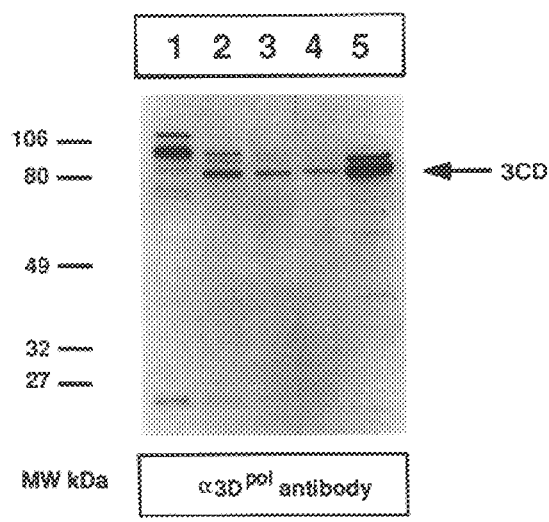
FIGS. 18A and 18B show an analysis of protein expression from cells transfected with RNA derived from recombinant poliovirus nucleic acid containing the gag gene of HIV-1.
Figure 18B:
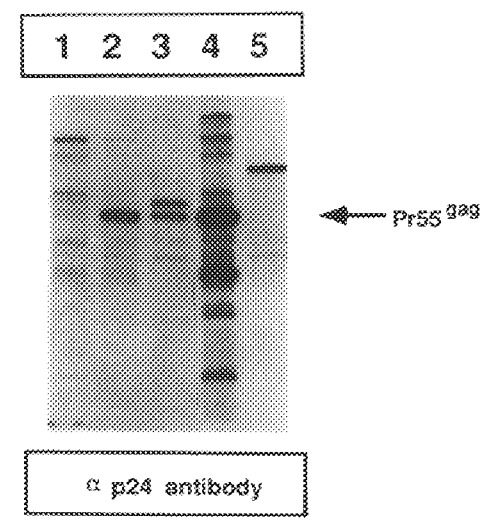
Figures 19A, 19B:
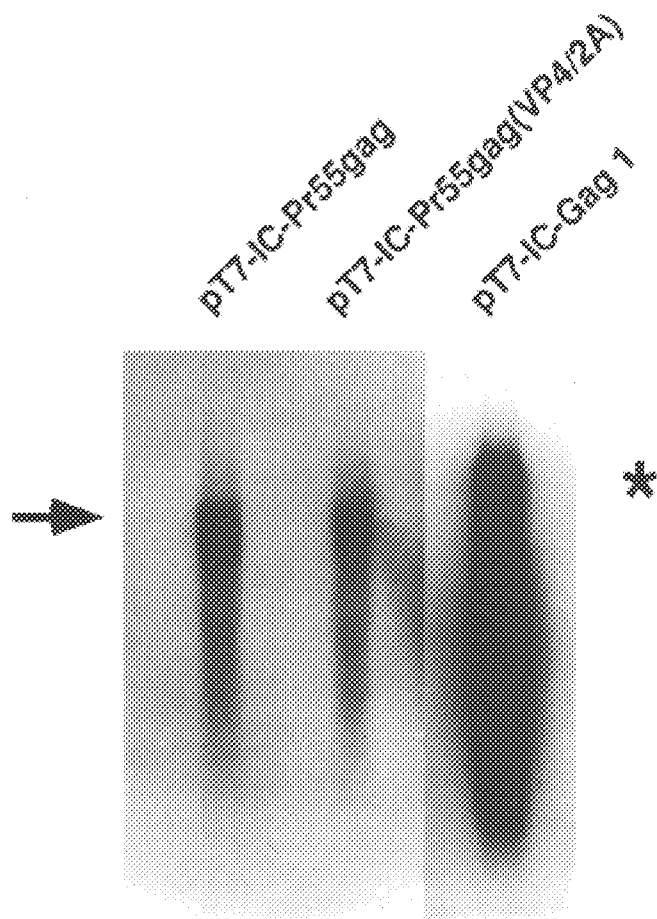
FIGS. 19A and 19B show quantitation of recombinant poliovirus RNA from transfected cells by Northern blot.

In FIGS. 9A, 9B, and 9C, IgA anti-poliovirus antibodies present in the saliva of animals immunized with the encapsidated recombinant poliovirus nucleic acids were analyzed. In this case, there was a clear increase in the levels of IgA anti-poliovirus antibodies in animals immunized via the intragastric, intrarectal, or intramuscular route at Day 14 and 45 post booster immunization. In FIGS. 10A and 10B, IgA anti-poliovirus antibodies from the vaginal lavage samples taken from mice immunized via the intrarectal or intramuscular route were analyzed. In this case, there was a clear increase over the pre-immune values at Day 45 post booster immunization with animals immunized via the intrarectal route. In contrast, there was not a significant increase in the levels of IgA anti-poliovirus antibodies in animals immunized via the intramuscular route. Finally, as shown in FIGS. 11A, 11B, and 11C, IgA anti-poliovirus antibodies were present in extracts from feces obtained from animals immunized via the intragastric, intrarectal or intramuscular route. In all cases, there was an increase of the IgA anti-poliovirus antibodies at Day 21, Day 14 post booster immunization and Day 45 post booster immunization. Levels were approximately 5-fold over the pre-immune levels taken at Day 0. It is possible that the levels of anti-poliovirus detected have been underestimated due to the possibility that the animals are also shedding poliovirus in the feces at this time. The shed poliovirus as well as anti-poliovirus antibodies form an immune complex which would not be detected in the ELISA assay.

Anti-HIV-1-gag Antibodies

Portions of the same samples that were collected to analyze anti-poliovirus antibodies were analyzed for the presence of anti-HIV-1-gag-antibodies. FIGS. 12A, 12B, and 12C show the serum levels of total IgG (representing IgG as the major species and IgM and IgA as the minor species) anti-HIV-1-gag antibodies in the serum of animals immunized via the intragastric, intrarectal, or intramuscular route. No consistent increase in the levels of serum antibodies directed against HIV-1-gag antibodies in animals immunized via the intragastric or intrarectal route was observed. This is represented by the fact that there was no increase in the levels above that observed at Day 0 (pre-immune) value. In contrast, there was an increase in the anti-HIV-1-gag antibodies levels in mice immunized via the intramuscular route. On Day 21 post immunization, there was a clear increase over the background value. The levels of anti-HIV-1-gag antibodies in the serum at Days 14 post boost and 45 post boost were clearly above the pre-immune values in the animals immunized via the intramuscular route.

In FIGS. 13A, 13B, and 13C, IgA anti-HIV-1-gag antibodies present in the saliva of animals immunized via the intragastric, intrarectal or intramuscular route. In this case, there was a clear increase over the pre-immune levels (Day 0) in animals immunized by all three routes of immunization. The highest levels of IgA anti-HIV-1-gag antibodies in the saliva were found at Day 45 post booster immunization. FIGS. 14A and 14B show a similar pattern for the samples obtained from vaginal lavage of animals immunized via the intrarectal or intramuscular route. In this instance, there was a clear increase at Days 14 and 45 post booster immunization in the levels of IgA anti-HIV-1-gag antibodies from animals immunized via the intrarectal route of immunization. The animals immunized via the intramuscular route exhibited an increase of IgA anti-HIV-1-gag antibodies in vaginal lavage samples starting at Day 12 through Day 21. The levels increased following the booster immunization at Day 21 resulting in the highest levels observed at Day 45 post booster immunization. In FIGS. 15A, 15B, and 15C, IgA anti-HIV-1-gag antibodies present in fecal extracts obtained from animals immunized via the three different routes were analyzed. In general, there was an increase of the pre-immune levels using all three routes of immunization that was most evident at Days 14 and 45 post booster immunization. The results of these studies clearly establish that administration of the encapsidated recombinant HIV-1-poliovirus nucleic acids via the intragastric, intrarectal, or intramuscular route results in the generation of anti-HIV-1-gag antibodies in serum, saliva, vaginal lavage, as well as fecal extracts. A greater serum anti-HIV-1-gag antibody response was obtained by immunization of the animals via the intramuscular route rather than the intragastric or intrarectal routes. However, IgA anti-HIV-1-gag antibodies in secretions of animal immunized via all three routes were observed.

EXAMPLE 4

PRODUCTION OF ANTI-POLIOVIRUS ANTIBODIES IN PIGTAIL MACAQUE IMMUNIZED WITH ENCAPSIDATED RECOMBINANT POLIOVIRUS NUCLEIC ACID CONTAINING A PORTION OF THE HIV-1 GAG GENE

A pigtail macaque was immunized with $5\times10^8$ PFU of a virus stock of type I attenuated poliovirus containing the encapsidated recombinant nucleic acid from pT7IC-Gag #2 (FIG. 2). For these studies, intrarectal immunization was performed because of the high concentration of gut associated lymphoid tissue in the rectum of primates. The virus was deposited in a volume of 1 ml using a syringe filter with soft plastic tubing and inserted 1 inch into the rectum. The analysis of the anti-poliovirus and anti-gag antibodies was as described in Example 2 except that anti-monkey-specific reagents were substituted for anti-murine-specific reagents.

Serum from the macaque prior to immunization (Day 0), 12 days post primary immunization (12 pp), 27 days post primary immunization (27 pp) were collected. A second administration of virus consisting of 1 ml of $5\times10^8$ PFU given intrarectally and $2.5\times10^7$ PFU of virus administered intranasally at 27 days post primary immunization. Fourteen days after the second administration of virus (14 days post booster) serum was collected.

All serum samples were diluted 1:400 in PBS and the levels of IgG anti-poliovirus antibody were determined by ELISA as described above. As shown in FIG. 16, there was a clear increase in the serum IgG anti-poliovirus antibodies, as measured by $OD_{414}$ in the ELISA, in the immunized macaque at 14 days post booster immunization. The levels were approximately 10-fold higher than the previous levels (Day 0). This study shows that intrarectal primary followed by intrarectal-intranasal booster immunization results in clear increase in the IgG anti-poliovirus antibodies.

MATERIALS AND METHODS II

The following materials and methods were used in Examples 5 and 6:

All chemicals were purchased from Sigma Chemical Company. Tissue culture media and supplements were purchased from Gibco/BRL Company. The [$^{35}$S] Translabel (methionine/cysteine) and methionine/cysteine-free DMEM were purchased from ICN Biochemicals. Restriction enzymes were obtained from New England Biolabs. The T7 RNA by the method of Grodberg and Dunn ((1988) *J. Bacteriol.* 170:1245–1253). Synthetic DNA primers were prepared at the University of Alabama Comprehensive Cancer Center facility or obtained from Cruachem, Fisher Co. Tri Reagent-LS was obtained from Molecular Research Center, Inc.

Tissue Culture Cells and Viruses

HeLa T4 and BSC-40 (African green monkey kidney/cell line derived from BSC 1 cells) cell monolayers were grown in Dulbecco's modified Eagle's medium (DMEM) supplemented with 5% fetal calf serum and 1×GMS-G supplement (complete medium). The stock of the poliovirus type 1 Mahoney was derived from transfection of an infectious cDNA clone of poliovirus obtained from B Semler, University of California at Irvine (Semler, B. L. et al. (1984) *Nucleic Acids Res*. 12:5123–5141). The stock of poliovirus type 1 Sabin was obtained from American Type Culture Collection. The recombinant vaccinia virus VV-P1, which expresses the poliovirus P1 capsid precursor protein upon infection, has also been previously described (Ansardi, D. C. et al. (1991) *J. Virol*. 65:2088–2092). Antisera (recombinant) to HIV-1 p25/24 Gag (Steimer, K. S. et al. (1986) *Virol.* 150:283–290) and a recombinant vaccinia virus vVKI (Karacostas, V. K. et al. (1989) *Proc. Natl. Acad. Sci*. (USA) 86:8964–8967), which expresses the Pr55$^{gag}$ protein upon infection, was obtained through the AIDS Research and Reference Reagent Program. The antisera to 3D$^{pol}$ has been previously described (Jablonski, S. A. et al. (1991) *J. Virol.* 65:4565–4572).

Construction of recombinant poliovirus nucleic acid containing the HIV-1 gag gene To subclone the HIV-1 recombinant poliovirus genomes, modifications were made to the poliovirus cDNA plasmid pT7-IC, which contains the poliovirus CDNA, and has been described previously (Choi, W. S. et al. (1991) *J. Virol.* 65:2875–2883). A unique Sac I restriction site was generated at the 5' end of the P1 region in the plasmid pT7-IC by a conservative single base change at nucleotide 748 by site-directed mutagenesis to generate the plasmid pT7-IC-Sac I (Sambrook, J. et al. Molecular Cloning: A Laboratory Manual, 2nd ed. (Cold Spring Harbor Laboratory Press, Cold Spring Harbor, N.Y., 1989). The mutation was confirmed by sequence analysis of ds DNA (Sambrook, J. et al. Molecular Cloning: A Laboratory Manual, 2nd ed. (Cold Spring Harbor Laboratory Press, Cold Spring Harbor, N.Y., 1989). A unique SnaBI restriction site was then generated in the same plasmid by PCR, at nucleotide 3359, using the following synthetic DNA primers: 5'-CAC-CCC-TCT-CCT-ACG-TAA-CCA-AGG-ATC-3' (SEQ ID NO: 9), and 5'-GTA-CTG-GTC-ACC-ATA-TTG-GTC-AAC-3' (SEQ ID NO: 10). The amplified DNA fragment was precipitated and digested with SnaBI and BstEII. After digestion of the plasmid pT7-IC-Sac I with SnaBI and BstEII, the PCR fragment was ligated into the plasmid. The resultant plasmid was designated pT7-IC-Sac I-SnaBI.

To construct recombinant poliovirus nucleic acid which contains the complete HIV-1 Pr55$^{gag}$ gene, nucleotides 345 to 1837 were amplified from the plasmid pHXB2 (Ratner, L. et al. (1985) *Nature* 313:277–284) by PCR using the following DNA primers: 5'-GGA-GAG-AGA-TGG-GAG-CTC-GAG-CGT-C-3' (SEQ ID NO: 11), and 5'-GCC- CCC-CTA-TAC-GTA-TTG-TG-3' (SEQ ID NO: 12). The DNA fragment was ligated into the plasmid pT7-IC-Sac I-SnaBI after digestion of the fragment DNA and pT7-IC-Sac I-SnaBI with Sac I and SnaBI DNA sequencing confirmed that the translational reading frame was maintained between the foreign gene and poliovirus. The final construct was designated as pT7-IC-Pr55$^{gag}$ .

A second recombinant poliovirus nucleic acid containing the HIV-1 gag gene was constructed to position nucleotides 1–949 of the poliovirus genome 5' to the HIV-1 gag gene. The following primers were designed to amplify a DNA fragment from the plasmid pT7-IC from a unique EcoRi site, located upstream of the T7 RNA polymerase promoter, to nucleotide 949: 5'-CCA-GTG-AAT-TCC-TAA-TAC-GAC-TCA-CTA-TAG-GTT-AAA-ACA-GC-3' (SEQ ID NO: 13) and 5'-CTC-TAT-CCT-GAG-CTC-CAT-ATG-TGT-CGA-GCA-GTT-TTT-GGT-TTA-GCA-TTG-3' (SEQ ID NO: 14). primers were designed to include a 2A protease cleavage site (tyrosine-glycine amino acid pair (underlined) preceded by six wild-type amino acids: Thr-Lys-Asp-Leu-Thr-Thr-Tyr-Gly) (SEQ ID NO: 15), corresponding to the authentic 2A cleavage site in the 3DP$^{pol}$ gene at nucleotide 6430 in the poliovirus genome, followed by a Sac I restriction site at the 3' end of the VP4 gene in the amplified fragment. The DNA fragment was ligated into pT7-IC-Pr55$^{gag}$ after digestion with EcoRI and Sac I. The final construct was designated pT7-IC-Pr55$^{gag}$(VP4/2A).

The construction and characterization of the pT7-IC-Gag 1 has been described in previous studies (Choi, W. S. et al. (1991) *J. Virol.* 65:2875–2883; Porter, D. C. et al. (1993) *J. Virol.* 67:3712–3719). Briefly, pT7-IC-Gag 1 was constructed by substitution of nucleotides 718 to 1549 of the HIV-1 gag gene (amplified using PCR) for the P1 coding region between nucleotides 1174 and 2470 in the infectious cDNA plasmid pT7-IC. This substitution encompasses most of the VP2 and VP3 capsid sequences while maintaining the VP4 and VP1 coding regions.

Encapsidation and serial passage of recombinant poliovirus nucleic acid containing the HIV-1 gag gene The encapsidation and serial passage of recombinant poliovirus nucleic acid using VV-P1 has been previously described (Morrow, C. D. et al. (1994) "New Approaches for Mucosal Vaccines for AIDS: Encapsidation and Serial Passage of Poliovirus Replicons that Express HIV-1 Proteins Upon Infection" AIDS *Res. and human Retroviruses* 10(2); Porter, D. C. et al. (1993) *J. Virol.* 67:3712–3719). Briefly, HeLa T4 cells were infected with 5 PFU/cell of VV-P1, which expresses the poliovirus capsid precursor protein P1. At 2 hours post-infection, the cells were transfected using the DEAE-Dextran method with RNA transcribed from the chimeric genomes in vitro as previously described (Choi, W. S. et al. (1991) *J. Virol.* 65:2875–2883; Pal-Ghosh, R. et al. (1993) *J. Virol.* 67:4621–4629; Porter, D. C. et al. (1993) *J. Virol.* 67:3712–3719). The cultures were harvested at 24 hours post-transfection by detergent lysis, overlaid on a 30% sucrose cushion (30% sucrose, 30 mM Tris pH 8 0, 1% Triton X-100, 0.1M NaCl), and centrifuged in a Beckman SW55Ti rotor at 55,000 rpms for 1.5 hours (Ansardi, D. C. et al. (1993) *J. Virol.* 67:3684–3690; Porter, D. C. et al. (1993) *J. Virol.* 67:3712–3719). The supernatant was discarded and the pellet washed under the same conditions in a low salt buffer (30 mM Tris pH 8.0, 0.1M NaCl) for an additional 1.5 hours. The pellets were then resuspended in complete DMEM and used for serial passage immediately or stored at −70° C. until used.

For serial passage of the encapsidated recombinant poliovirus nucleic acid and generation of virus stocks, BSC-40 cells were first infected with 10–20 PFU/cell of VV-P1. At 2 hours post-infection, the cells were infected with passage 1 of the encapsidated recombinant poliovirus nucleic acid. The cultures were harvested at 24 hours post-infection by three successive freeze/thaws, sonicated, and clarified by low speed centrifugation at 14,000×g for 20 minutes. The supernatants were then stored at −70° C. or used immediately for additional passages following the same procedure.

Metabolic labeling and immunoprecipitation of viral proteins from infected cells To metabolically label proteins from infected cells, the cultures were starved for methionine/cysteine at the times indicated post-infection by incubation in DMEM minus methionine/cysteine for 30 minutes. At the end of this time, [$^{35}$S] Translabel was added for an additional one hour. Cultures were then processed for immunoprecipitation of viral proteins by lysing the cells with RIPA buffer (150 mM NaCI, 10 mM Tris pH 7.8, 1% Triton X-100, 1% sodium deoxycholate, 0.2% sodium dodecyl sulfate). Following centrifugation at 14,000×g for 10 minutes, the designated antibodies were added to the supernatants which were then incubated at 4° C. for 24 hours. The immunoprecipitates were collected by addition of 100 μl protein A-Sepharose (10% weight/volume in RIPA buffer). After a 1 hour incubation at room temperature, the protein A-Sepharose beads were collected by brief centrifugation and washed 3 times with RIPA buffer. The bound material was eluted by boiling 5 minutes in gel sample buffer (62.5 mM Tris pH 6.8, 2% SDS, 20% glycerol, 0.05% bromophenol blue, and 0.7M 13-mercaptoethanol). The proteins were analyzed by SDS-polyacrylamide gel electrophoresis and radiolabeled proteins were visualized by fluorography using sodium salicylate as previously described (Ansardi, D. C. et al. (1993) *J. ViroL* 67:3684–3690; Porter, D. C. etal. (1993) *J. Virol.* 67:3712–3719). The immunoprecipitated proteins were quantitated by phosphorimagery where indicated (Molecular Dynamics).

Nucleic acid hybridization of RNA

Total cellular RNA was prepared from cells transfected with equivalent amounts of in vitro transcribed RNA as described by the manufacturer using Tri Reagent-LS (Molecular Research Center, Inc.). The amounts of full length RNA transcripts were estimated by agarose gel electrophoresis prior to transfection (Choi, W. S. et al. (1991) *J. Virol.* 65:2875–1883). The RNA was then denatured, separated on a formaldehyde-1.0% agarose gel, and transferred from the gel to a nitrocellulose filter by capillary action. Equivalent amounts of RNA, as measured by levels of rRNA, were loaded into each lane of the gel. For analysis of encapsidated recombinant poliovirus RNA, the RNA was isolated from virions (Ricco-Hesse, R. M. et al. (1987) *Virol.* 160:311–322) which had been concentrated through a sucrose cushion as previously described (Ansardi, D. C. et al. (1993) *J. Virol.* 67:3684–3690; Porter, D. C. et al. (1993) *J. Virol.* 67:3712–3719). The RNA was denatured and spotted onto nitrocellulose using a dot blot apparatus according to established protocols (Sambrook, J. et al. Molecular Cloning: A Laboratory Manual, 2nd ed. (Cold Spring Harbor Laboratory Press, Cold Spring Harbor, N.Y., 1989). The RNA was immobilized onto the nitrocellulose by baking in a vacuum oven at 80° C. for 1 hour.

The conditions for prehybridization, hybridization and washing of RNA immobilized onto nitrocellulose were as described previously (Choi, W. S. et al. (1991) *J. Virol.* 65:2875–2883; Pal-Ghosh, R. et al. (1993) *J. Virol.* 67:4621–4629; Porter, D. C. et al. (1993) *J. Virol.* 67:3712–3719). Briefly, the blot was prehybridized in hybridization buffer (50% deionized formamide, 6X SSC, 1% SDS, 0.1% Tween 20, and 100 μg/mL yeast tRNA). The blot was then incubated in hybridization buffer containing $1\times10^6$ cpm/mL of a [$^{32}$P] labeled riboprobe complementary to nucleotides 671–1174 of the poliovirus genome (Choi, W. S. et al. (1991) *J. Virol.* 65:2875–2883; Pal-Ghosh, R. et al. (1993) *J. Virol.* 67:4621–4629; Porter, D. C. et al. (1993) *J. Virol.* 67:3712–3719). After hybridization, the blot was washed two times with 0.1×SSC 0.1% SDS at room temperature and at 65° C. The blot was then exposed to X-ray film with an intensifying screen. The levels of RNA from each sample were quantitated by phosphorimagery (Molecular Dynamics).

Passage of recombinant poliovirus nucleic acid containing the HIV-1 gag gene with type 1 attenuated poliovirus Virus stocks of encapsidated recombinant poliovirus nucleic acid containing HIV-1 gag gene were serially passaged with wild-type poliovirus as previously described (Morrow, C. D. et al. (1994) "New Approaches for Mucosal Vaccines for AIDS: Encapsidation and Serial Passage of Poliovirus Replicons that Express HIV-1 Proteins Upon Infection" *AIDS Res. and Human Retroviruses* 10(2); Porter, D. C. et al. (1993) *J. Virol.* 67:3712–3719). Briefly, BSC-40 cells were co-infected with 10 PFU/cell of type 1 Sabin poliovirus and a virus stock of encapsidated recombinant poliovirus nucleic acid at pass 21. The infected cells were harvested at 24 hours post-infection by three successive freeze/thaws, sonicated, and clarified by low speed centrifugation. Approximately one-half of the supernatant was used for serial passaging by re-infection of BSC-40 cells. After 24 hours, the cultures were harvested as described above and the procedure was repeated for an additional 2 serial passages.

EXAMPLE 5

CONSTRUCTION, EXPRESSION, AND REPLICATION OF RECOMBINANT POLIOVIRUS NUCLEIC ACIDS CONTAINING THE ENTIRE HIV-1 GAG GENE

To further define the requirements of the P1 region for the replication and encapsidation of poliovirus RNA, the complete gag gene of HIV-1 was substituted for the P1 capsid coding sequences. For these studies the plasmid pT7-IC (FIG. 17A), which contains the promoter sequences for T7 RNA polymerase positioned 5' to the complete poliovirus CDNA, was used (Choi, W. S. et al. (1991) *J. Virol.* 65:2875–2883). A unique Sal I restriction site is located after the poly (A) tract that can be used to linearize the cDNA before in vitro transcription; the RNA transcripts from this cDNA are infectious upon transfection into tissue culture cells (Choi, W. S. et al. (1991) *J. Virol.* 65:2875–2883). In order to substitute the entire P1 capsid region with the HIV-1 gag gene, a unique Sac I restriction site was generated at nucleotide 748, immediately following the translational start site of poliovirus. A unique SnaBI restriction site was generated at nucleotide 3359, which is positioned eight amino acids prior to the 2A protease cleavage site (tyrosine-glycine) located at nucleotide 3386; previous studies have suggested a requirement for the amino acid at the P4 position for autocatalytic processing of the polyprotein by the 2A protease (Harris, K. et al. (1990) *Sem. in Virol.* 1:323–333). The resultant plasmid, pT7-IC-Sac I-SnaBI was then used for insertion of the HIV-1 gag gene. pT7-IC-Pr55$^{gag}$ (FIG.

17B) was constructed by insertion of the complete HIV-1 gag gene from nucleotides 345 to 1837; the Sac I and SnaBI restriction sites were introduced at the 5' and 3' ends of the gene. Substitution of the entire P1 region from the translational start site of poliovirus to the 2A protease (3386), which autocatalytically cleaves from the polyprotein upon translation (Toyoda, H. et al. (1986) Cell 45:761–770), results in expression of Pr55$^{gag}$ protein after proteolytic processing of the polyprotein.

Figure 20:
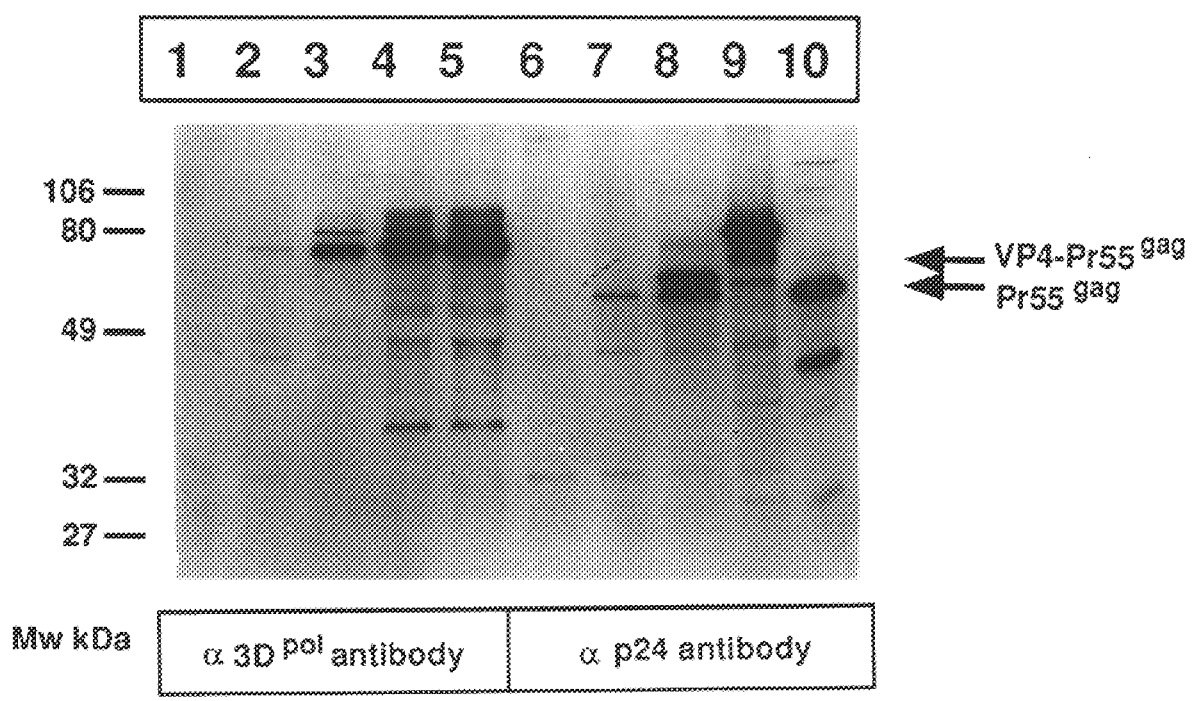
FIG. 20 shows an analysis of poliovirus and HIV-1 specific protein expression from cells infected with recombinant poliovirus nucleic acid encapsidated in trans using VV-P1.
Figures 21A, 21B:
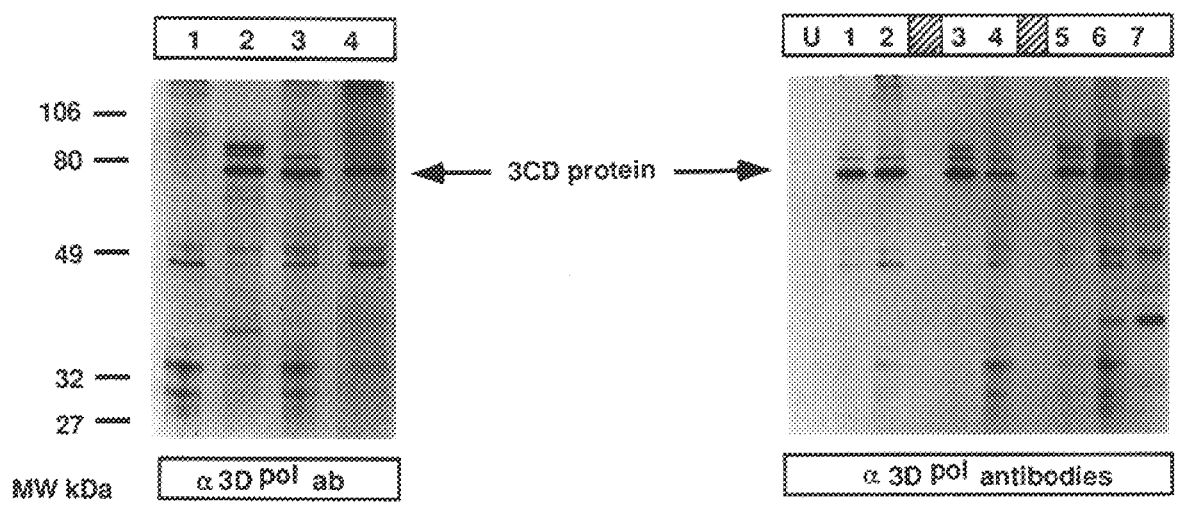
FIGS. 21 A and 21B show an analysis of protein expression from cells infected with normalized amounts of encapsidated recombinant poliovirus nucleic acid stocks and material derived from serial passage of equivalent amounts of encapsidated recombinant poliovirus nucleic acid virus stocks with VV-P1.
Figure 22:
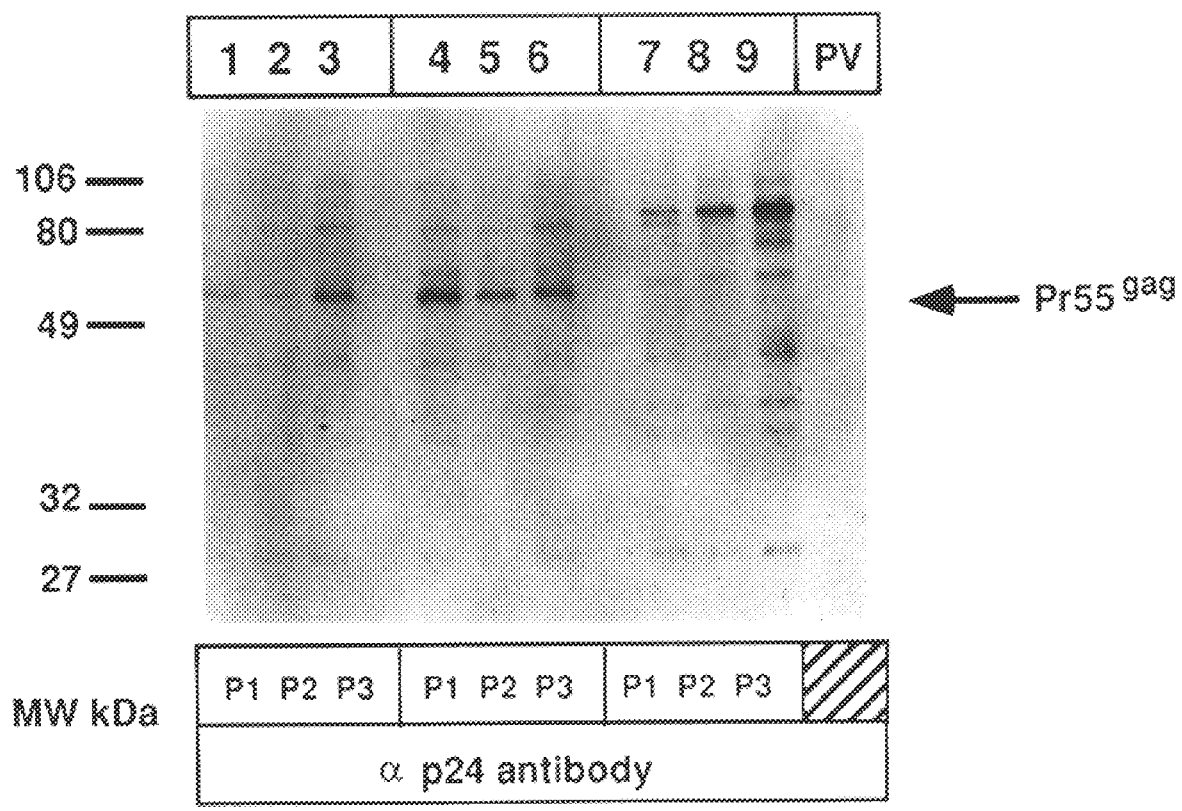
FIG. 22 shows an analysis of protein expression from cells infected with material derived from the serial passage of encapsidated recombinant poliovirus nucleic acid with wild-type poliovirus.

Naturally occurring defective interfering (DI) genomes of poliovirus contain heterologous deletions of the P1 coding region that encompass the VP3, VP1 and VP2 capsid sequences. All known poliovirus D1 genomes maintain an intact VP4 coding region (Kuge, S. et al. (1986) *J. Mol. Biol.* 192:473–487). A second recombinant poliovirus nucleic acid was generated in which the gag gene was substituted in frame for the VP2, VP3 and VP1 capsid sequences, from nucleotides 949 to 3359 to maintain the VP4 coding region. For this construct, a DNA fragment was amplified by PCR from the plasmid pT7-IC containing sequences encoding VP4 followed by the codons for eight amino acids containing a tyrosine-glycine amino acid pair. Substitution of the EcoRI to Sac I fragment into pT7-IC-$Pr55^{gag}$ results in the final plasmid, pT7-IC-$Pr55^{gag}$ (VP4/2A), which contains the VP4 coding sequences fused in-frame at the 5' end of the complete gag gene (FIG. 17C). In each construct, the insertion of HIV-1 gag gene sequences maintains the translational reading frame with poliovirus.

Poliovirus and HIV-1-specific protein expression from the recombinant poliovirus nucleic acids which contain the HIV-1 gag gene was analyzed after transfection of recombinant poliovirus RNA into cells which had been previously infected with VV-P1 (FIGS. 18A and 18B). Briefly, Cells were infected with VV-P1 at a multiplicity of infection of 5. At 2 hours post infection, the cells were transfected with RNA derived from in vitro transcription of the designated plasmids. Cells were metabolically labeled, and cell extracts were incubated with the antibodies indicated and immunoreactive proteins were analyzed on SDS-polyacrylamide gels: (FIG. 18A) Lane 1, mock-transfected cells; Lane 2, cells transfected with RNA derived from pT7-IC-$Pr55^{gag}$; Lane 3, cells transfected with RNA derived from pT7-IC-$Pr55^{gag}$ (VP4/2A); Lane 4, cells transfected with RNA derived from pT7-IC-Gag 1; Lane 5, cells infected with type 1 Mahoney poliovirus at a multiplicity of infection of 30. (FIG. 18B): Lane 1, mock-transfected cells; Lane 2, cells transfected with RNA derived from pT7-IC-$Pr55^{gag}$; Lane 3, cells transfected with RNA derived from pT7-IC-$Pr55^{gag}$(VP4/2A); Lane 4, cells infected with vVK1 at a multiplicity of infection of 10; Lane 5, cells transfected with RNA derived from pT7-IC-Gag 1. The molecular mass standards and positions of relevant proteins are indicated.

Under the conditions for metabolic labeling, the 3CD protein, which is a fusion between the $3C^{pro}$ and $3D^{pol}$ proteins, is the predominant 3D containing viral protein detected from poliovirus-infected cells (Porter, D. C. et al (1993) *Virus. Res.* 29:241–254). A protein with an approximate molecular mass of 72 kDa, corresponding to the 3CD protein of poliovirus, was detected from cells transfected with RNA from pT7-IC-$Pr55^{gag}$ and pT7-IC-$Pr55^{gag}$(VP4/2A) (FIG. 18A, lanes 2 and 3), but not from mock-transfected cells (FIG. 18A, lane 1). The 3CD protein was also immunoprecipitated from cells transfected with RNA derived from pT7-IC-Gag I (FIG. 18A, lane 4), which was used as a positive control for transfections in these studies (Porter, D. C. et al. (1993) *J. Virol.* 3712–3719).

For analysis of the expression of HIV-1 Gag protein, the extracts were incubated with antip25/24 antibodies (FIG. 18B). A lysate from cells infected with the recombinant vaccinia virus vVK 1, which contains the HIV-1 gene sequences encoding the complete gag and pol genes, was used as a control for $Pr55^{gag}$ protein expression (Karacostas, V. K. et al. (1989) *Proc. Natl. Acad. Sci.* (USA) 86:8964–8967). A protein with an apparent molecular mass of 55 kDa that co-migrated with protein immunoprecipitated from cells infected with vVK1 (FIG. 18B, lane 4) was detected from cells transfected with RNA from pT7-IC-$Pr55^{gag}$ and pT7-IC-$Pr55^{gag}$(VP4/2A) (FIG. 18B, lanes 2 and 3). In addition, a protein of higher molecular mass was immunoprecipitated from cells transfected with RNA from pT7-IC-$Pr55^{gag}$(VP4/2A) (FIG. 18B, lane 3). This protein probably is a VP4-$Pr55^{gag}$ precursor protein.

The replication of the transfected RNA derived from the recombinant poliovirus nucleic acid was also analyzed by Northern blot (FIGS. 19A and 19B). HeLa T4 cells were transfected with RNA transcribed in vitro from pT7-IC-$Pr55^{gag}$, pT7-IC-$Pr55^{gag}$(VP4/2A) and pT7-IC-Gag 1. At 9 hours postransfection, total cellular RNA was prepared, separated in a 1% formaldehyde-agarose gel, blotted onto nitrocellulose and analyzed using a riboprobe complementary to nucleotides 671–1174 of the poliovirus genome. (Choi, W. S. et al. (1991) *J. Virol.* 65:2875–2883; Pal-Ghosh, R. et al. (1993) *J. Virol.* 67:4621–4629; Porter, D. C. et al. (1993) *J. Virol.* 67:3712–3719) (FIG. 19A) The order of the samples is indicated. The migration of RNA of the predicted size, which was derived from in vitro transcription of pT7IC-$Pr55^{gag}$ and pT7-IC-$Pr55^{gag}$(VP4/2A), is indicated by an arrow. The asterisk indicates the migration of RNA of the expected size which was derived from pT7-IC-Gag 1 (Porter, D. C. et al. (1993) *J. Virol.* 67:3712–3719). The radioactivity of the Northern blot was quantitated using phosphorimagery.

The migration of RNA from pT7-IC-$Pr55^{gag}$ and pT7-IC-$Pr55^{gag}$(VP4/2A) transfected cells was slightly faster on the formaldehyde-agarose gel than RNA from pT7-IC-Gag 1, which is consistent with the predicted 6.3–6.4 kb size for RNA from pT7-IC-$Pr55^{gag}$ and pT7-IC-$Pr55^{gag}$(VP4/2A) versus the 7.0 kb size for RNA from pT7-IC-Gag 1 (FIG. 19A). Quantitation of the major bands of radioactivity from each sample by phosphorimagery indicated that the values for pT7-IC-$Pr55^{gag}$ and pT7-IC-$Pr55^{gag}$(VP4/2A) were similar although the amounts of RNA detected from both recombinant poliovirus nucleic acids were lower than that for RNA obtained from pT7-IC-Gag 1 (FIG. 19B). Together, these results demonstrate that the RNA from pT7-IC-$Pr55^{gag}$ and pT7-IC-$Pr55^{gag}$(VP4/2A) replicate to similar levels in transfected cells.

EXAMPLE 6

ENCAPSIDATION AND SERIAL PASSAGE OF RECOMBINANT POLIOVIRUS NUCLEIC ACID CONTAINING THE ENTIRE HIV-1 GAG GENE

Cells were infected with VV-P1 and then transfected with RNA transcribed in vitro from pT7-IC-$Pr55^{gag}$, pT7-IC-$Pr55^{gag}$(VP4/2A) and pT7-IC-Gag 1. The encapsidated recombinant poliovirus genomes were passaged in cells which had been previously infected with VV-P1 for a total of 21 serial passes. Consistent with the nomenclature used herein, the encapsidated virus stocks of pT7-IC-$Pr55^{gag}$ and pT7-IC-$Pr55^{gag}$(VP4/2A) are referred to as vIC-$Pr55^{gag}$ and vIC-$Pr55^{gag}$(VP4/2A), respectively.

For analysis of poliovirus and HIV-1-specific protein expression, pass 21 virus stocks of encapsidated recombinant poliovirus nucleic acid were used to infect cells. After metabolic labeling, lysates from the cells were incubated with anti-$3D^{pol}$ and anti-p24 antibodies (FIG. 20). With reference to FIG. 20, cells were transfected with RNA derived from in vitro transcription of the designated plasmids at 2 hours post-infection with VV-P1. Encapsidated genomes were harvested from cells as described in Materials and Methods II and used to re-infect cells which had been previously infected with VV-P1. The encapsidated recombinant poliovirus genomes were subsequently serially passaged in VV-P1-infected cells for 21 serial passes. Cells were infected with virus stocks at pass 21 and metabolically labeled. Cell lysates were incubated with the designated antibodies and immunoreactive proteins were analyzed SDS-polyacrylamide gel; Lanes 1 and 6, mock-infected cells; Lanes 2 and 7, cells infected with vIC-Pr55$^{gag}$; Lanes 3 and 8, cells infected with vIC-Pr55$^{gag}$(VP4/2A); Lanes 4 and 9, cells infected with vIC-Gagl; Lane 5, cells infected with type 1 Mahoney poliovirus; Lane 10, cells infected with vVK1. The molecular mass standards and positions of relevant proteins are indicated.

Although the 3CD protein was detected from each of the recombinant poliovirus nucleic acid virus stocks, decreased levels of 3CD protein were consistently detected from cells infected with virus stocks of vIC-Pr55$^{gag}$ (FIG. 20, lane 2) as compared to cells infected with virus stocks of vIC-Pr55gag(VP4/2A) (FIG. 20, lane 3) and vIC-Gag 1 (FIG. 20, lane 4). Upon incubation of the lysates with anti-p24 antibodies, a protein with an apparent molecular mass of 55 kDa was detected from the vIC-Pr55$^{gag}$ (FIG. 20, lane 7) and vIC-Pr55$^{gag}$(VP4/2A) (FIG. 20, lane 8) virus stocks; this protein co-migrated with Pr55$^{gag}$ expressed from cells infected with the recombinant vaccinia virus vVK1 (FIG. 20, lane 10) (Karacostas, V. et al. (1989) *Proc. Natl. Acad. Sci.* (USA) 86:8964–8967). Again, infection of cells with the vIC-Pr55$^{gag}$(VP4/2A) virus stock resulted in an increased level of the 55 kDa protein, compared to cells infected with vIC-Pr55$^{gag}$. Consistent with previous studies, vIC-Gag 1 expressed an 80 kDa Gag-P1 fusion protein in infected cells (FIG. 20, lane 9) (Porter, D. C. et al. (1993) *J. Virol.* 67:3712–3719).

Since it has been demonstrated that after transfection that RNA from each of the recombinant poliovirus nucleic acids resulted in similar levels of replication and protein expression, detection of reduced levels of protein expression from cells infected with vIC-Pr55$^{gag}$ as compared to vIC-Pr55$^{gag}$(VP4/2A) could be the result of a difference in infectivity (i.e., interaction with receptor, uncoating) between the recombinant poliovirus nucleic acids. To address this question, RNA was isolated from equivalent amounts of vIC-Pr55$^{gag}$ and vIC-Pr55$^{gag}$ (VP4/2A) virus stocks, which had been serially passaged with VV-P1 for 21 passes. Serial dilutions of the RNA were then spotted onto nitrocellulose and analyzed using a riboprobe as described in Materials and Methods II. Quantitation of the radioactivity from each sample by phosphorimagery indicated values from vIC-Pr55$^{gag}$(VP4/2A) virus stocks which were approximately 15 times higher than the values obtained for RNA from vIC-Pr55$^{gag}$. The results of these studies corroborate the differences in expression of 3CD and HIV-1 Gag protein observed for the recombinant poliovirus nucleic acids. To address the possibility that the recombinant poliovirus nucleic acids might have differences in infectious potential, cells were infected with equivalent amounts of encapsidated recombinant poliovirus nucleic acids, as determined by RNA hybridization, and metabolically labeled followed by immunoprecipitation with anti-3D$^{pol}$ antibodies (FIG. 21 A). Equivalent amounts of a 72 kDa protein, corresponding to the 3CD protein, were detected from each of the recombinant poliovirus nucleic acid virus stocks. Quantitation of the radioactivity from each sample by phosphorimagery confirmed that the levels of 3CD were similar.

With reference to FIG. 21 A, cells were infected with normalized amounts of encapsidated poliovirus nucleic acid virus stocks and metabolically labeled. Cells lysates were incubated with the designated antibodies and immunoreactive proteins were analyzed on an SDS-polyacrylamide gel: Lane 1, mock infected cells; Lane 2, cells infected with vIC-Pr55$^{gag}$ recombinant poliovirus stock; Lane 3, cells infected with vIC-Pr55$^{gag}$(VP4/2A) recombinant poliovirus stock; Lane 4, cells infected with vIC-Gag1 recombinant poliovirus stock. With reference to FIG. 21 B, equivalent amounts of each of the recombinant poliovirus stocks were serially passaged in VV-P1-infected cells for 2 passes as described in Materials and Methods II. Cells were infected with material derived from passes 1 and 2 and metabolically labeled. Cells lysates were incubated with the designated antibodies and immunoreactive proteins were analyzed on an SDS-polyacrylamide gel; Lane U, mock-infected cells; Lane 1, cells infected with material from pass 1 of vIC-Pr55$^{gag}$ with VV-P1; Lane 3 cells infected with material from pass 1 of vIC-Pr55$^{gag}$(VP4/2A) with VV-P1; Lane 4, cells infected with material from pass 2 of vIC-Pr55$^{gag}$(VP4/2A) with VV-P1; Lane 5, cells infected with material from pass 1 of vIC-Gag 1 with VV-P1; Lane 6, cells infected with material from pass 2 of viC-Gag 1 with VV-P1; Lane 7, cells infected with type 1 Mahoney poliovirus. The molecular mass standards and positions of relevant proteins are indicated.

To determine whether the decreased levels of RNA isolated from the vIC-Pr55$^{gag}$ virus stock at pass 21 as compared to the vIC-Pr55$^{gag}$(VP4/2A) and vIC-Gag 1 virus stocks were attributable to differences in the efficiency of encapsidation of RNA which contains the VP4 coding sequences versus the encapsidation of RNA which has a complete deletion of the P1 region, cells which had been previously infected with VV-P1 were infected with normalized amounts of each of the encapsidated recombinant poliovirus nucleic acid virus stocks. After 24 hours, complete cell lysis had occurred and the supernatant was processed as described in Materials and Methods II; one additional passage was performed in cells previously infected with VV-P1. For analysis of protein expression from the serially passaged material, cells were infected with material from passages 1 and 2, metabolically labeled, and the cell lysates were incubated with anti-3D$^{pol}$ antibodies (FIG. 21B). Similar amounts of the 3CD protein were detected from each of the passages of equivalent amounts of vIC-Pr55$^{gag}$ (FIG. 21B, lanes 1 and 2), vIC-Pr55$^{gag}$(VP4/2A) (FIG. 21B, lanes 3 and 4) and vIC-Gag 1 recombinant poliovirus nucleic acid virus stocks (FIG. 21 B, lanes 5 and 6) with VV-P1. Thus, the reduced levels of RNA and 3CD protein expression detected from the vIC-Pr55$^{gag}$ recombinant poliovirus nucleic acid virus stocks as compared to vIC-Pr55$^{gag}$(VP4/2A) and vIC-Gag 1 after 21 serial passes with VV-P1 (FIG. 20) were not apparent after passage of the recombinant poliovirus nucleic acids with VV-P1 for 2 serial passes.

Since all known DIs of poliovirus contain an intact VP4 coding region, it was examined whether the recombinant poliovirus nucleic acid which contains the VP4 coding sequences might have an advantage if the recombinant poliovirus nucleic acid had to compete with the wild type genome for capsid proteins. To determine whether vIC-Pr55$^{gag}$ and vIC-Pr55$^{gag}$(VP4/2A) could also be maintained upon passage with wild-type poliovirus, cells were co-infected with equal amounts of either the vIC-Pr55$^{gag}$, vIC-Pr55$^{gag}$ (VP4/2A) or vIC-Gag 1 and type 1 Sabin poliovirus. After 24 hours, complete cell lysis had occurred and the supernatant was processed as described in Materials and Methods II; two additional passages were performed. Cells were infected with material from each serial passage, metabolically labeled and the cell extracts were incubated with antibodies to p24/25 protein (FIG. 22). With reference to FIG. 22, cells were co-infected with equal amounts of either the vIC-Pr55$^{gag}$, vIC-Pr55$^{gag}$ (VP4/2A) or vIC-Gag 1 and type 1 Sabin poliovirus. The cells were harvested at 24 hours post-infection and the supernatant was processed as described in Materials and Methods II; two additional passages were performed. Cells were infected from each of the serial passages and metabolically labeled. The cell lysates incubated with the designated antibody and immunoreactive proteins were analyzed on an SDS-polyacrylamide gel: Lane U, uninfected cells; Lanes 1, 2 and 3, cells infected with material derived from the indicated passes of vIC-Pr55$^{gag}$ with type 1 Sabin poliovirus; Lanes 4, 5 and 6, cells infected with material derived from the indicated passes of vIC-PR55$^{gag}$(VP4/2A) with type 1 Sabin poliovirus; Lanes 7, 8 and 9, cells infected with material derived from the indicated passes of vIC-Gag 1 with type 1 Sabin poliovirus; Lane PV, cells infected with type 1 Sabin poliovirus. Each passage is denoted as follows: P1, pass 1; P2, pass 2; and P3, pass 3. The molecular mass standards and positions of relevant proteins are indicated.

No HIV-1-specific protein was cells infected with type 1 Sabin poliovirus alone (FIG. 22, lane PV); the 80 kDa gag-P1 fusion protein was detected from cells infected with material from passages 1, 2 and 3 of the vIC-Gag 1 recombinant poliovirus nucleic acid and wild-type poliovirus (FIG. 22, lanes 7–9) (Porter, D. C. et al. (1993)*J. Virol.* 67:3712–3719). Upon serial passage of vIC-Pr55$^{gag}$ (FIG. 22, lanes 1–3) and vIC-Pr55$^{gag}$(VP4/2A) (FIG. 22, lanes 4–6) virus stocks with type 1 Sabin, a protein which migrated at approximately 55 kDa was detected from cells infected with material from passages 1, 2, and 3. There was no consistent difference detected between the levels of Pr55$^{gag}$ expression from either recombinant poliovirus nucleic acid. Thus, the presence or absence of the VP4 coding region did not effect the capability of the recombinant poliovirus nucleic acid to compete with the wild-type poliovirus genomes for the P1 protein that was evident after three serial passages.

The construction and characterization of a first poliovirus genome which contains the complete 1.5 kb gag gene of HIV-1 substituted for the entire P1 region, and a second poliovirus genome in which the gag gene is positioned 3' to the VP4 coding region of the P1 capsid region are described herein. Transfection of RNA from each of the constructs into cells resulted in similar levels of protein expression and RNA replication. Both genomes were encapsidated upon transfection into cells previously infected with VV-P1 . Serial passage of the recombinant poliovirus nucleic acids with VV-P1 resulted in the production of virus stocks of each of the encapsidated genomes. Analysis of the levels of encapsidated recombinant poliovirus nucleic acids after extended serial passage revealed that the recombinant poliovirus nucleic acids which contain the VP4 coding region were present at higher levels in the encapsidated virus stocks than the recombinant poliovirus nucleic acids which contain the gag gene substituted for the entire P1 region; no difference was detected in the levels of encapsidation of either recombinant poliovirus genome following limited serial passages in the presence of VV-P1 or Sabin type 1 poliovirus. The results of this study are significant because this is the first demonstration that poliovirus genomes which contain a foreign gene substituted for the entire P1 region can be encapsidated by P1 provided in trans.

Although the presence of the VP4 coding region was not absolutely required for RNA encapsidation, it was evident that recombinant poliovirus nucleic acids which contain a complete substitution of the P1 region with the HIV-1gag gene were encapsidated less efficiently than recombinant poliovirus nucleic acids which maintain the VP4 coding sequences (nucleotides 743 to 949) positioned 5' to the gag gene. When RNA derived from each of the encapsidated recombinant poliovirus nucleic acid virus stocks after 21 serial passes with VV-P1 was isolated and quantitated by nucleic acid hybridization, the RNA from vIC-Pr55$^{gag}$(VP4/2A) and vIC-Gag 1 recombinant poliovirus nucleic acid virus stocks, which contained VP4, were present at levels that were 15 and 50 times higher, respectively, than RNA from vIC-Pr55$^{gag}$ virus stocks. Although it is clear from these results that VP4 is not required for encapsidation, the presence of VP4 might enhance RNA encapsidation. Since limited passage of equivalent amounts of each of the recombinant poliovirus nucleic acid virus stocks with VV-P1 indicated no significant difference in the encapsidation of recombinant poliovirus nucleic acids containing VP4 versus recombinant poliovirus nucleic acids which contain a deletion of the entire P1 coding region, it was possible that the effect of VP4 on encapsidation would be more apparent if the recombinant poliovirus RNA had to compete with the wild-type genomes for the P1 capsid protein. This situation would be analogous to the encapsidation of defective interfering (DI) genomes in that the defective genome must compete effectively with the wild-type genome to be maintained in the virus stock. However, it was determined that RNA from vIC-Pr55$^{gag}$ and vIC-Pr55$^{gag}$(VP4/2A) was maintained in virus stocks for 3 serial passages in the presence of type 1 poliovirus. Thus, during limited serial passage the recombinant poliovirus genomes did compete effectively with type 1 Sabin poliovirus RNA for capsid proteins.

Using the complementation system described herein, it is possible to substitute the entire P1 region with at least 1.5 kb of foreign DNA. One feature of the expression system described herein is that the foreign protein is expressed as a polyprotein which is processed by 2A$^{pro}$. Thus, it is possible to express foreign proteins in a native conformation from poliovirus genomes if the residual amino acids at the amino or carboxy termini do not interfere with proper folding. Preliminary experiments have demonstrated the 55 kDa HIV-1 Gag protein expressed from poliovirus recombinant poliovirus nucleic acids is biologically active (i.e. formation of virus-like particles). If the exact protein sequence is required for protein function, the desired protein can be expressed using internal ribosomal entry sites positioned within the recombinant poliovirus nucleic acid.

MATERIALS AND METHODS III

The following materials and methods were used in Examples 7, 8, and 9:

Plasmid Constructions

All manipulation of recombinant DNA was carried out according to standard procedures (Maniatis, T. et al. Molecular Cloning: A Laboratory Manual (Cold Spring Harbor Laboratory Press, Cold Spring Harbor, N.Y., 1982). The starting plasmid for these studies, pT7-IC, contains the entire full-length poliovirus infectious cDNA positioned immediately downstream from the phage T7 promoter (Choi, W. S. et al. (1991) *J. Virol.* 65:2875–2883). The full-length cDNA encoding CEA (shown in SEQ ID NO: 16, the amino acid sequence of CEA is shown in SEQ ID NO: 17), subcloned into pGEM plasmid (Beauchemin, N. et al. (1987) *Mol. Cell. Biol.* 7:3221–3230), was obtained from Dr. David Curiel, University of Alabama at Birmingham (originally obtained from Dr. Judy Kantor, NIH, Bethesda, Md.).

For construction of the backbone poliovirus vector used for insertion of the carcinoembryonic antigen (CEA) gene, two independent PCR reactions were performed. The first was used to amplify the region from nucleotides 1 to 743 of the poliovirus genome using the following PCR primers: 5'-CCA-GTG-AAT-TCC-TAA-TAC-GAC-TAC-CTA-TAG-GTT-AAA-ACA-GC-3' (5' primer) (SEQ ID NO: 18) and 5'-GA-TGA-ACC-CTC-GAG-ACC-CAT-TAT-G-3' (3' primer) (SEQ ID NO: 19).

A second set of PCR primers were designed to amplify a region of the poliovirus genome from 3370 to 6117. The PCR primers were designed so that a unique SnaBI restriction site would be created 12 nuclcotides from the end of the P1 gene, resulting in an additional four amino acids upstream from the tyrosine-glycine cleavage site. For subsequent subcloning, the PCR product was digested with SnaBI and BglII, which cuts at nucleotide 5601 in the poliovirus genome. The PCR primers used were as follows: 5'-CCA-CCA-AGT-ACG-TAA-CCA-CAT-ATG-G (5' primer) (SEQ ID NO: 20) and 5'-GTG-AGG-ACTG-CT-GG-3' (3' primer) (SEQ ID NO: 21).

The conditions for PCR were as follows: 1 min at 94° C., 3 min at 37° C., and 3 min at 72° C. After 30 cycles, a 7-min incubation at 72° C. was included prior to cessation of the PCR reaction. PCR reactions were extracted successively with phenol:chloroform (1:1) and chloroform:isoamyl alcohol (24:1), and then DNA was precipitated with ethanol. After collection of the precipitate by centrifugation, the DNA was dried and resuspended in water. The DNA was then digested with the appropriate restriction endonuclease enzymes at the 5' and 3' end of the PCR-amplified products.

Construction of pT7-IC-CEA-sig$^-$

To obtain a signal minus version of the CEA gene, PCR was used to amplify a region from the CEA cDNA. The primers used for this PCR reaction were as follows: 5'-CAC-CAC-TGC-CCT-CGA-GAA-GCT-CAC-TAT-TG-3' (5' primer) (SEQ ID NO: 22) and 5'-CAC-CAC-TGC-CCT-CGA-GAA-GCT-CAC-TAT-TG-3' (3' primer) (SEQ ID NO: 23).

The DNA primers were chosen to create an XhoI site at the 5' end and a SnaBI site at the 3' terminus of the amplified DNA. The length of the amplified DNA was approximately 100 base pairs less than that of the full-length amplified product for the CEA DNA, corresponding to a loss of 34 amino acids from the amino terminus representing the signal sequence. The conditions for PCR and isolation of the amplified product are as described in Materials and Methods III. Prior to ligation, the amplified product was digested with XhoI and SnaBI.

The plasmid pT7-IC was digested with EcoRI and BglII. The DNA fragment which contains the poliovirus genome from nucleotides 56012 to the SalI site (1.8 kilobases plus the 3.7 kilobases of the vector=5.5 kilobases) was isolated. In the same ligation, this 5.8-kilobase fragment was ligated with the PCR-amplified products from nucleotides 1–743 (EcoRI-XhoI), the CEA gene (XhoI-SnaBI), and the PCR-amplified product containing poliovirus nucleotides 3370 (SnaBI) to 5601 (BglII). After incubation at 15° C. overnight, the ligated products were transformed into *Escherichia coli* DH5α and the colonies were selected on ampicillin-containing plates. Plasmids isolated from individual colonies were screened for the desired insert by restriction enzyme digestion. The final plasmid was designated pT7-IC-CEA-sig$^-$.

Cell Culture and Viruses.

HeLa cells were purchased from the American Type Culture Collection and were maintained in monolayer culture in DMEM (GIBCO/BRL) supplemented with 5% fetal bovine serum. BSC-40 cells were maintained in DMEM with 5% fetal bovine serum as described previously (Ansardi, D. A. et al. (1991) *J. Virol.* 65:2088–2092).

The vaccinia viruses used for these studies were grown in TK-143-B cells (American Type Culture Collection) and were concentrated for experimental use as previously described (Ansardi, D. A. et al. (1991) *J. Virol.* 65:2088–2092). The titers of vaccinia virus were determined by plaque assay on BSC-40 cell monolayers. The recombinant vaccinia virus used for the encapsidation experiments (VV-P1) was constructed as described previously (Ansardi, D. A. et al. (1991) *J. Virol.* 65:2088–2092). The recombinant vaccinia virus which expresses the CEA (rV-CEA) has been previously described (Kantor, J. et al. (1992) *J. Natl. Cancer Inst.*84:1084–1091; Kantor, J. et al. (1992) *Cancer Res.* 52:6917–6925).

In Vitro Transcription, Transfections, and Metabolic Labeling

In vitro transcription was carried out as described previously (Choi, W. S. et al. (1991) *J. Virol.* 65:2875–2883). The in vitro transcribed RNA was transfected into HeLa cells with DEAE-dextran (molecular mass, 500 kDa) as a facilitator as described previously (Choi, W. S. et al. (1991) *J. Virol* 65:2875–2883). The cells were first infected with vaccinia virus for 2 h prior to transfection. After the 2 hour infection period, the cells were washed once with DMEM without methionine-cysteine or leucine (depending on the metabolic label), and incubated in this medium for an additional 45 min to 1 hour. In the case of recombinant poliovirus nucleic acid-infected cells, the infections were allowed to proceed 4–6 hours prior to metabolic labeling. For [$^{35}$S]methionine-cysteine labelings, the cells were washed once and incubated in DMEM without methionine-cysteine plus [$^{35}$S]methionine-cysteine (Translabel;ICN) 150 μCi/mi final concentration. In the case of metabolic labeling with [$^{3}$H]leucine, cells were labeled for 1.5 h using [$^{3}$H]leucine (Amersham) (350 μCi/ml) in a final volume of 0.2 ml leucine-free DMEM. After the labeling period, the cells were washed once with PBS and processed for radioimmunoprecipitation as described previously (Ansardi, D. A. et al. (1991) *J. Virol.* 65:2088–2092). To detect CEA protein, a CEA-specific monoclonal antibody (Col-1) at a concentration of 3 μg/ml was used.

Encapsidation and Serial Passage of Recombinant poliovirus nucleic acids by VV-P1

Procedures for encapsidation of the recombinant poliovirus nucleic acids have been described previously (Porter, D. C. et al. ((1993) *J. Virol.* 67:3712–2719; Ansardi, D. A. et al. (1993) *J. Virol.* 67:3684–3690). Briefly, HeLa cells were infected with 20 PFUs/cell of VV-P1 for 2 hours. The cells were then transfected with in vitro transcribed RNA using DEAE-dextran (Choi, W. S. et al. (1991) *J. Virol.* 65:2875–2883). Sixteen hours after transfection, the cells and medium were harvested by directly adding Triton X-100 to the medium, at a final concentration of 1%. The medium-cell lysate was clarified in a microcentrifuge for 20 min at 14,000 ×g. The clarified lysate was treated with 20 μg/ml of RNase A at 37° C. for 15 min, then diluted to 4 ml with 30 mM Tris-HCl (pH 8.0, 0.1M NaCl, 1% Triton X-100), and overlaid on a 0.5 ml-sucrose cushion (30% sucrose, 30 mM Tris-HCl pH 8.0, 1M NaCl, 0.1% BSA) in SW 55 tubes. The sucrose cushion was centrifuged at 45,000 rpm for 2 h. Pelleted material was washed with PBS-0.1% BSA and recentrifuged at 45,000 rpm for 2 h. The final pellet was resuspended in 0.6 ml complete medium. BSC-40 cells were infected for 2 hours with 20 PFUs/cell of VV-P1 , and 0.25 ml of the 0.6 ml was used to infect cells infected with VV-P1; after 24 hours, the cells and media were harvested. This was designated Pass 1.

For serial passage of the encapsidated recombinant poliovirus nucleic acids, BSC-40 cells were infected with 20 PFUs of VV-P1 /cell. At 2 hours posttransfection, the cells were infected with Pass 1 of the encapsidated recombinant poliovirus nucleic acids. The cultures were harvested at 24 hours postinfection by three successive freeze-thaws, sonicated, and clarified by centrifugation at 14,000 –g for 20 min. The supernatants were stored at x70° C. or used immediately for additional passages, following the same procedure.

Estimation of the Titer of Encapsidated Recombinant poliovirus nucleic acids

Since the encapsidated recombinant poliovirus nucleic acids have the capacity to infect cells, but lack capsid proteins, they cannot form plaques and therefore virus titers cannot be quantified by traditional assays. To overcome this problem, a method to estimate the titer of the encapsidated recombinant poliovirus nucleic acids by comparison with wild-type poliovirus of known titer (Porter, D. C. et al. ((1993) *J. Virol.* 67:3712–2719; Ansardi, D. A. et al. (1993) *J. Virol.* 67:3684–3690) was used. The resulting titer is then expressed in infectious units of recombinant poliovirus nucleic acids, since the infection of cells with the recombinant poliovirus nucleic acids does not lead to plaque formation due to the absence of P1 capsid genes. It was determined experimentally that the infectivity of equal amounts of infectious units of encapsidated recombinant poliovirus nucleic acids correlates with equal amounts of PFUs of wild-type poliovirus.

Immunization of Mice and Analysis of CEA-Specific Antibody Response

The encapsidated recombinant poliovirus nucleic acids contain a type I Mahoney capsid. Since the type I strain of poliovirus does not infect mice, transgenic mice (designated as Tg PVR1) which express the receptor for poliovirus and are susceptible to poliovirus and are susceptible to poliovirus infection (Ren, R. et al. (1990) *Cell* 63:353–362) were used. Mice (4–5-week old) were immunized by i.m. infection at monthly intervals with recombinant poliovirus nucleic acids expressing CEA; each mouse received 3 doses containing approximately 3 ×10$^4$ infectious units/mouse in 50 µl sterile PBS. To remove residual VV-P1, the recombinant poliovirus nucleic acid preparations were incubated with anti-vaccinia virus antibodies (Lee Biomolecular, San Diego, Calif.). The complete removal of residual VV-P1 was confirmed by the lack of vaccinia virus plaques after a 3-day plaque assay. Blood was collected from the tail veins of mice before and at selected times after immunization, centrifuged, and the plasma was collected and frozen until assay. ELISA was used for the determination of antigen-specific antibodies. The assays were performed in 96-well polystyrene microtiter plates (Dynatech, Alexandria, Va.) coated with recombinant CEA or whole poliovirus type I at a concentration of 5 and 1 µg/ml, respectively. The CEA used for these studies was expressed in *E. coli*, using a pET vector with a 6-histidine affinity tag to facilitate purification (Novagen). The majority of the CEA product isolated from the nickel column used for purification was an 80-kDa protein corresponding to the nonglycosylated CEA. The poliovirus type I (Sabin) used was grown in tissue culture cells and purified by centrifugation (Ansardi, D. A. et al. (1993) *J. Virol.* 67:3684–3690). Dilutions of sera were incubated overnight at 4° C. on coated and blocked ELISA plates, and the bound immunoglobulins were detected with horseradish peroxidase-labeled antimouse immunoglobulins (Southern Biotechnology Associates, Birmingham, Ala.). At the end of the incubation time (3 hours at 37° C.), the peroxidase substrate 2,2'-azino-bis-(3-ethylbenzthiazoline) sulfonic acid (Sigma, St. Louis, Mo.) in citrate buffer (pH 4.2) containing 0.0075% $H_2O_2$ was added. The color developed was measured in $V_{max}$ kinetic microplate reader (Molecular Devices, Palo Alto, Calif.) at 414 nm. The results were expressed as absorbance values at a fixed dilution or as end point titration values.

EXAMPLE 7

CONSTRUCTION OF RECOMBINANT POLIOVIRUS NUCLEIC ACID CONTAINING THE GENE FOR CARCINOEMBRYONIC ANTIGEN

Figure 23A:
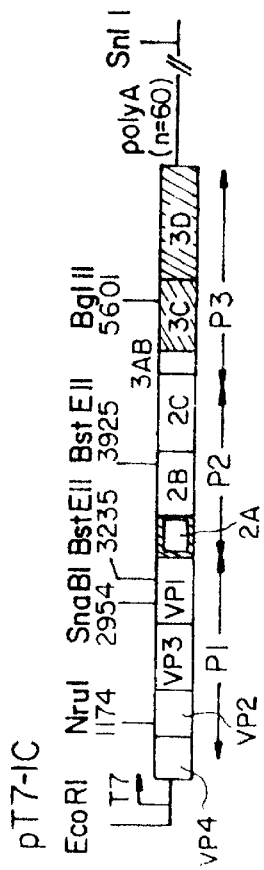
FIGS. 23A, 23B, and 23C show construction of recombinant poliovirus nucleic acid containing the gene for carcinoembryonic antigen.
Figure 23B:
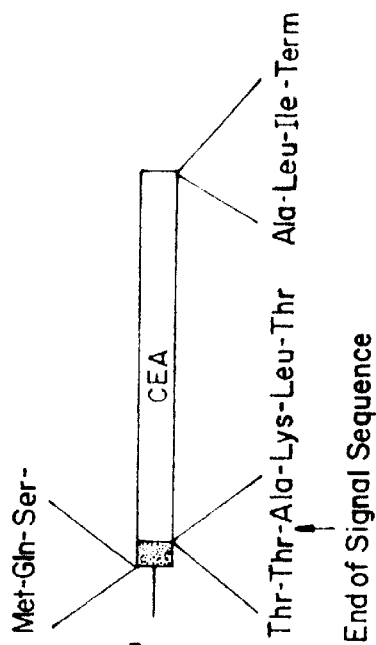
Figure 23C:
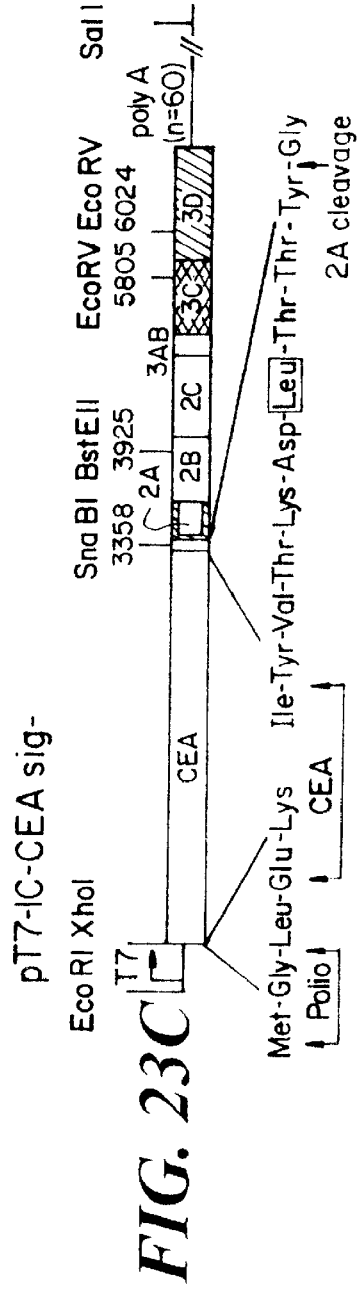

The starting plasmid for the experiments described herein contains the full-length infectious poliovirus CDNA positioned downstream from a phage T7 promoter, designated pT7-IC (Choi, W. S. et al. (1991) *J. Virol.* 65:2875–2883) (FIG. 23A). With reference to FIG. 23A, the poliovirus capsid proteins (VP4, VP3, VP2, and VP1) are encoded in the P1 region of the poliovirus genome; the viral proteinase 2A and viral proteins 2B and 2C are encoded in the P2 region; and the viral proteins 3AB, 3C, and 3D (RNA polymerase) are encoded in the P3 region. The relevant restriction sites used for construction of the recombinant poliovirus nucleic acid containing the gene for CEA are indicated. With reference to FIG. 23B, which is a schematic of the CEA protein, the signal sequence of the CEA protein consists of 34 amino acids (black box). The signal peptidase cleavage site occurs between the alanine and lysine amino acids. The codon for the carboxyl terminal isoleucine amino acid is followed by a TAA termination codon. Construction of the recombinant poliovirus nucleic acid containing the signal-minus CEA gene occurred as follows: PCR was used to amplify the CEA-gene encoding amino acids from the lysine at the amino terminus of signal-minus CEA to the isoleucine at the COOH terminus of CEA as shown in FIG. 23B. To subclone the gene encoding the signal-minus CEA protein, XhoI and SnaBI restriction endonuclease sites were positioned within the PCR primers. The final construct encodes the first two amino acids of the poliovirus P1 protein (Met-Gly) followed by two amino acids, leucine and glutamic acid (encoded by the XhoI restriction site) followed by the lysine amino acid of the signal-minus CEA protein. The CEA gene was positioned so that nine amino acids will be spaced between the C-terminal isoleucine of CEA and the tyrosine-glycine cleavage site for the 2A proteinase; the leucine amino acid required for 2A cleavage is boxed in FIG. 23C. This final construct, as shown in FIG. 23C, was designated pT7-IC-CEA-sig⁻.

Figure 25A:
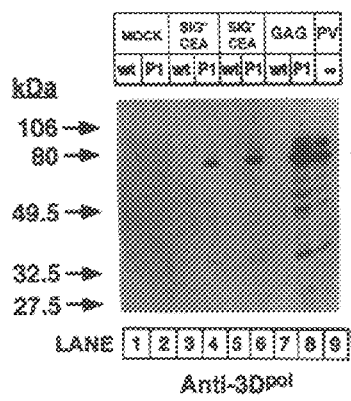
FIGS. 25A, 25B, and 25C show an analysis of poliovirus and carcinoembryonic expression from cells infected with recombinant poliovirus nucleic acid containing the gene for carcinoembryonic antigen; the recombinant poliovirus nucleic acid was encapsidated and serially passaged with capsid proteins provided by VV-P1.
Figure 25B:
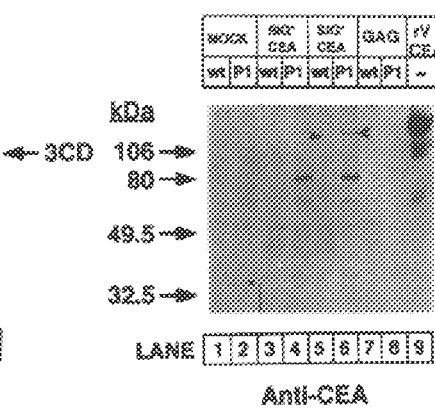
Figure 25C:
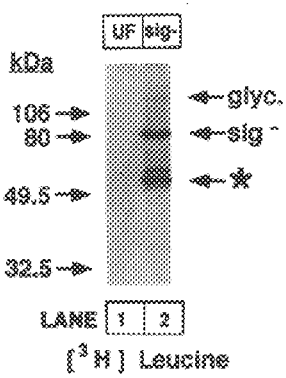
Figure 26A:
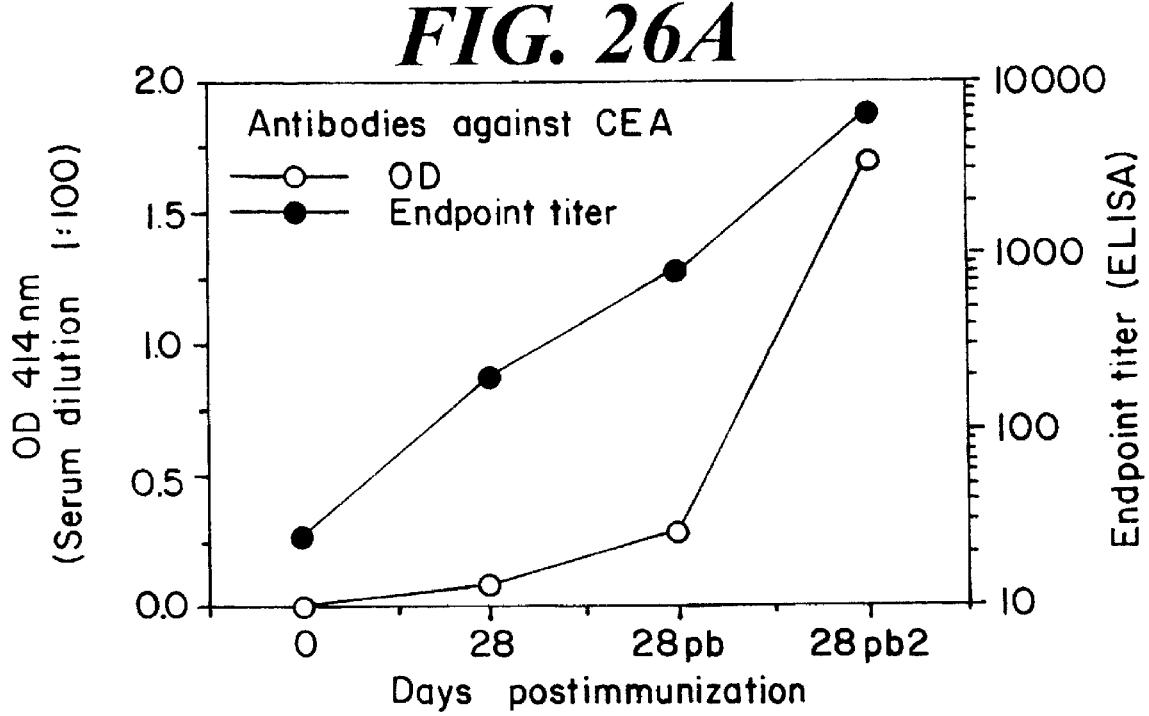
FIGS. 26A and 26B show antibody response to encapsidated recombinant poliovirus nucleic acid expressing carcinoembryonic antigen.
Figure 26B:
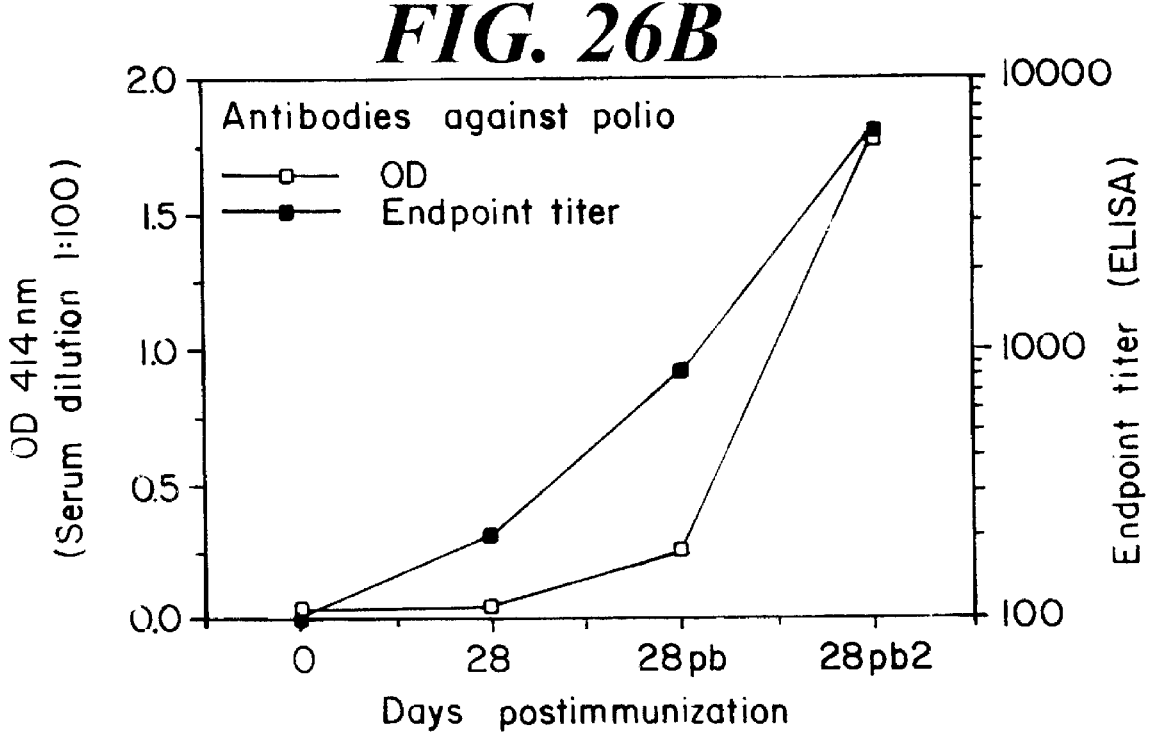

After the pT7-IC plasmid is linearized at the unique Sal I restriction site, in vitro transcription mediated by phage T7 RNA polymerase is used to generate RNA transcripts for transfection. Transfection of the in vitro RNA transcript into tissue culture cells (i.e., HeLa cells) results in translation and replication of the RNA, which leads to production of infectious poliovirus. It has been found that the infectivity of the RNA derived from this plasmid is in the range of 10$^6$ PFUs/µg transfected RNA (Choi, W. S. et al. (1991) *J. Virol.* 65:2875–2883). Previous studies have found that the majority of the P1 region of the poliovirus cDNA can be deleted without affecting the capacity of the resulting RNA genome to replicate when transfected into cells (Kaplan, G. et al. (1988) *J. Virol.* 62:1687–1696). To extend these studies, it was investigated whether the entire P1 region can be substituted with the 2.4-kilobase cDNA for CEA (FIG. 23B; Beauchemin, N. et al. (1987) *Mol. Cell. Biol.* 7:3221–3230; Oikawa, S. et al. (1987) *Biochim. Biophys. Acta.* 142:511–518).

In preliminary studies, it was found that RNA containing full-length CEA was not replication competent. It was possible that the signal sequence (amino acids 1–34) of the CEA protein was directing the CEA-P2-P3 fusion protein to the endoplasmic reticulum and in doing so prevented replication of the RNA. To test this possibility, the CEA gene was engineered to remove the first 34 amino acids of the CEA protein, which has been postulated to be the signal sequence (Oikawa, S. et al. (1987) *Biochim. Biophys. Acta.* 142:511–518; Thompson, J. et al. (1988) *Tumor Biol.* 9:63–83). PCR was used to amplify a region from amino acids 35–688 of the CEA gene that was then subcloned into the poliovirus recombinant poliovirus nucleic acid. The resulting DNA encoded the first two amino acids of the poliovirus P1 protein (Met-Gly) followed by two amino acids (Leu-Glu) derived from the XhoI restriction endonuclease site, followed by amino acid 35 (Lys) of the CEA protein. The isoleucine in CEA was fused to an additional nine amino acids (Tyr-Val-Thr-Lys-Asp-Leu-Thr-Thr-Tyr) in the predicted protein product. In this CEA protein, a leucine residue at the P4 position was included for optimal 2A autocatalytic cleavage (Harris, K. S. et al. (1990) *Semin. Virol.* 1:323–333).

Following in vitro transcription of pT7-IC-CEA-sig$^-$, the RNA transcripts were transfected into cells previously infected with VV-P1. For these studies five independent clones containing the signal-minus CEA gene (designated as sig$^-$CEA) were tested. As a positive control, a recombinant poliovirus nucleic acid which contains the HIV-1 gag gene (corresponding to the capsid, p24 protein) positioned between nucleotides 1174 and 2470 of the poliovirus genome was used. Cells were also infected with poliovirus to serve as a control in these experiments. At 6 hours posttransfection, the cells were metabolically labeled and $^{35}$S-labeled proteins were immunoprecipitated with either anti-3D$^{pol}$ (FIG. 24A) of anti-CEA (Col-1 monoclonal antibody (FIG. 24B). The immunoprecipitated proteins were separated on SDS-10% polyacrylamide gels, and autoradiograms of these gels were generated (shown in FIGS. 24A and 24B). Additional sets of cells were either infected with poliovirus (FIG. 24A) or a recombinant vaccinia virus which expresses CEA (rV-CEA, FIG. 24B) to serve as a source of marker proteins. The origins of the samples in each of the lanes for both FIG. 24A and FIG. 24B are as follows: Lane 1, mock transfected cells; Lane 2, cells transfected with RNA derived from clone 1 of PT7-IC-CEA-sig$^-$; Lane 3, cells transfected with RNA derived from clone 2 of pT7-IC-CEA-sig$^-$; Lane 4, cells transfected with RNA derived from clone 3 of pT7-IC-CEA-sig$^-$; Lane 5, cells transfected with RNA derived from clone 4 of pT7-IC-CEA-sig$^-$; Lane 6, cells transfected with RNA derived from clone 5 of pT7-IC-CEA-sig$^-$; Lane 7, cells transfected with RNA derived from transcription of pT7-IC-Gag 1; Lane 8, cells infected with either poliovirus (FIG. 24A) or rV-CEA (FIG. 24B). The migration of the molecular mass markers is noted. The migration of 3CD (FIG. 24A) and glycosylated and unglycosylated forms of CEA (FIG. 24B) are also noted.

In contrast to the results with the CEA recombinant poliovirus nucleic acids encoding the signal sequence, the 3CD protein from cells transfected with RNA derived from five individual clones of pT7-IC-CEA-sig$^-$was detected. The levels of 3CD expression in this experiment were comparable to those of cells transfected with RNA derived from in vitro transcription of pT7-IC-Gag 1, which was known from previous studies to be replication competent (Porter, D. C. et al. (1993) *J. Virol.* 67:3712–3719; FIG. 24A). To determine if the CEA protein was expressed in the transfected cells, the lysates were also incubated with the Col-1 antibody to immunoprecipitate CEA-related proteins (FIG. 24B). Since the CEA protein should not be glycosylated, it was expected that the CEA product would be approximately 80 kDa in molecular mass. In each of the transfections with RNA derived the five independent clones, an 80-kDa protein was immunoprecipitated; this protein was not detected in cells transfected with recombinant poliovirus nucleic acids containing the HIV-1 gag gene.

EXAMPLE 8

ENCAPSIDATION AND SERIAL PASSAGE OF RECOMBINANT POLIOVIRUS NUCLEIC ACID CONTAINING THE GENE FOR CARCINOEMBRYONIC ANTIGEN

To determine whether the recombinant poliovirus nucleic acids containing the CEA sig$^-$gene could be encapsidated if provided the poliovirus capsid proteins, cells were infected first with VV-P 1, followed by transfection with either the RNA derived pT7-IC-CEA-sig$^-$or PT7-IC-Gag 1. A mock transfection was also included as an additional control. At 24 h posttransfection, extracts of the cells were generated by addition of detergents to the culture medium, and poliovirus-like particles were concentrated from the extracts by centrifugation through a 30% sucrose cushion. After resuspension, the concentrated material was used to infect cells that had been infected previously with either wild-type vaccinia virus or VV-P1 (passage 1). This coinfection was allowed to proceed overnight, after which extracts of the cells were generated by repeated freezing and thawing. The freeze-thaw extracts were clarified and used to repeat the coinfection procedure. This process was repeated for an additional nine serial passages to generate stocks of the encapsidated recombinant poliovirus nucleic acids. For the experiment shown in FIGS. 25A-C, the lysates from Pass 10 material were used to infect BSC-40 cells. At 6.5 hours postinfection, the cells were starved for 30 min in methionine-cysteine-free DMEM, and then were metabolically labeled for an additional 90 min. The cell lysates were then analyzed by immunoprecipitation with either anti-3D$^{pol}$ antibody (FIG. 25A) or antibody to the CEA protein (Col-1, FIG. 25B). The origins of the samples in the lanes for FIGS. 25A and 25B are as follows: Lane 1, cells that were infected with wild-type vaccinia virus and then mock-transfected; Lane 2, cells that were infected with VV-P1 and then mock-transfected; Lane 3, cells that were infected with wild-type vaccinia virus and then transfected with RNA derived from in vitro transcription of pT7-IC-CEA-sig$^-$; Lane 4, cells that were infected with VV-P1 and then transfected with RNA derived from pT7-IC-CEA-sig$^-$; Lane 5, cells that were infected with wild-type vaccinia virus and then transfected with RNA derived from pT7-IC-CEA-sig$^-$(a second independent clone); Lane 6, cells were infected with VV-P1 and then transfected with RNA derived from pT7-IC-CEA-sig$^-$(a second independent clone); Lane 7, cells that were infected with wild-type vaccinia virus and then transfected with RNA derived from in vitro transcription of pT7-IC-Gag 1; Lane 8, cells that were infected with VV-P1 and then transfected with RNA derived from in vitro transcription of pT7-IC-Gag 1; Lane 9, cells that were infected with poliovirus (FIG. 25A) or recombinant vaccinia virus CEA (rV-CEA, FIG. 25B). The migration of the molecular mass markers is noted. In FIG. 25A, the migration of 3CD protein is noted, whereas in FIG. 25B, the migrations of the glycosylated (gly) and nonglycosylated (sig⁻) forms of CEA are noted. Arrows note the position of the anti-CEA immunoreactive proteins of larger molecular mass observed in cells infected with encapsidated poliovirus nucleic acid containing the signal-minus CEA gene. In FIG. 25C, cells were infected with a Pass 20 stock of encapsidated recombinant poliovirus nucleic acid containing the signal-minus CEA gene and then metabolically labeled with [$^3$H]leucine. The origins of the samples in the lanes for FIG. 25C are as follows: Lane 1 includes uninfected cells metabolically labeled, followed by immunoprecipitation with Col-1 antibody; Lane 2, cells infected with encapsidated recombinant poliovirus nucleic acid containing the signal-minus CEA gene, followed by immunoprecipitation with Col-1 antibody. The molecular mass standards are noted as well as the migration of glycosylated CEA (glyc.), nonglycosylated CEA ($sig^-$), and breakdown product (asterisk).

No expression of 3CD proteins was detected upon infection of cells with the sample originating from the mock-transfected cells and serially passaged 10 times with either wild-type vaccinia virus of VV-P1 (FIG. 25A). From analysis of 3CD expression, it was concluded that RNA derived from transcription of pT7-IC-CEA-$sig^-$was encapsidated when passaged in the presence of VV-P 1, but not in the presence of wild-type vaccinia virus.

To determine if the CEA protein was expressed from the encapsidated recombinant poliovirus nucleic acids, the extracts from infected cells that had been metabolically labeled followed by immunoprecipitation with the Col-1 antibody (FIG. 25B) were analyzed. Again, in samples from mock-transfected cells that had been subsequently passaged in the presence of either wild-type vaccinia virus or VV-P 1, no immunoreactive protein was detected. A protein of molecular mass 80 kDa was immunoprecipitated from cells infected with the extracts originating from cells transfected with the RNA derived from pT7-IC-CEA $sig^-$which has been passaged in the presence of VV-P1, but not in the presence of wild-type virus. As expected, no Col-1 immunoreactive material was detected in cells infected with the RNA derived from pT7-IC-Gag 1, although this RNA was encapsidated in cells in the presence of VV-P1 (FIG. 25A).

Although the majority of the CEA protein immunoprecipitated from the cells infected with either stock of the encapsidated recombinant poliovirus RNA was the 80-kDa protein corresponding to the expected molecular mass of unglycosylated CEA, it was noted there was a small amount of protein immunoprecipitated corresponding to the molecular mass for the fully glycosylated CEA protein (180 kDa). To further explore this result, a concentrated stock of the signal-minus CEA recombinant poliovirus nucleic acid that had been passaged an additional 10 times (20 serial passages in all) and concentrated by pelleting through a 30% sucrose cushion prior to use in these experiments was used. Cells were infected with the encapsidated recombinant poliovirus nucleic acids, followed by metabolic radiolabeling for 1.5 h with [$^3$H]leucine since CEA contains more leucine amino acids than methionine or cysteine (Oikawa, S. et al. (1987) *Biochim. Biophys. Acta.* 142:511–518). This should increase the sensitivity of detection of the higher molecular mass CEA proteins. Three proteins were immunoprecipitated using the Col-1 antibody from [$^3$H]leucine-labeled cells infected with the stock of the encapsidated recombinant poliovirus nucleic acid (FIG. 25C). One of these proteins corresponded to the unglycosylated protein of a smaller molecular mass of approximately 80 kDa, while a protein of a smaller molecular mass, corresponding to approximately 52 kDa, was also immunoprecipitated. This protein is believed to represent a breakdown product of the CEA protein that was not detected previously because of the relatively few methionine or cysteine amino acids found in the CEA protein. A third protein of approximately 180 kDa was also immunoprecipitated, suggesting that glycosylated CEA protein might be produced in cells infected with the encapsidated recombinant poliovirus nucleic acids at low levels.

EXAMPLE 9

PRODUCTION OF ANTI-POLIOVIRIJS AND ANTI-CARCINOEMBRYONIC ANTIGEN ANTIBODIES IN MICE IMMUNIZED WITH ENCAPSIDATED RECOMBINANT POLIOVIRUS NUCLEIC ACID CONTAINING THE GENE FOR CARCINOEMBRYONIC ANTIGEN

To evaluate the immunogenicity of the encapsidated recombinant poliovirus nucleic acids which express the CEA protein, transgenic mice that express the receptor for poliovirus and are susceptible to infection with poliovirus were used (Ren, R. et al. (1990) *Cell* 63:353–362). The mice were bred in a germ-free environment until use in the experiments. The four mice used in the experiment were bled prior to i.m. immunization with approximately $10^4$ infectious units of the encapsidated recombinant poliovirus nucleic acid which expresses CEA. The serum samples from the mice at each of the pre- and postimmune time points were pooled and assayed using a solid-phase ELISA with whole poliovirus or recombinant CEA expressed in *E. coli* as the coating solution. The results are presented as absorbance 414-nm values at a fixed dilution and as end point titration values for anti-CEA (FIG. 26A) an antipoliovirus (FIG. 26B). By 28 days after the second booster immunization, a pronounced CEA-specific antibody response was detected as measured by the ELISA assay. The end point titer had increased from 1:25 (preimmune) to 1:6400 (FIG. 26A). A similar increase was observed in the antipoliovirus in the serum samples (FIG. 26B). As a control, no increase in anti-CEA antibodies in the sera from mice immunized with the recombinant poliovirus nucleic acid expressing IHIV-1 Gag was found. Taken together, these results demonstrate that the recombinant poliovirus nucleic acids infect cells, presumably the muscle myofibers at the site of injection, and express sufficient amounts of CEA to stimulate an anti-CEA antibody response.

The construction and characterization of RNA recombinant poliovirus nucleic acids which express the CEA protein when infected is described herein. A recombinant poliovirus nucleic acid encoding the signal-minus CEA protein was replication competent and expressed nonglycosylated CEA protein when transfected into cells. Using the methods of encapsidating recombinant poliovirus nucleic acids described herein, stocks of encapsidated recombinant poliovirus nucleic acids containing the signal-minus CEA gene were generated. The use of encapsidated poliovirus recombinant poliovirus nucleic acids as a vaccine vehicle has several distinguishing features: (a) this is one of the few vector systems based entirely on an RNA virus. Since poliovirus replication does not involve DNA intermediates, in contrast to retroviruses, the possibility of recombination in the host cell DNA is virtually eliminated; (b) infection of cells with encapsidated recombinant poliovirus nucleic acids results in an amplification of the recombinant poliovirus nucleic acid RNA and preferential expression of the foreign gene over cellular gene products since poliovirus has evolved mechanisms to promote the synthesis of its own viral proteins (Ehrenfeld, E. et al. (1982) *Cell* 28:435–436); and (c) the encapsidated poliovirus recombinant poliovirus nucleic acids are noninfectious because they do not encode the viral P1 capsid proteins. The recombinant poliovirus nucleic acid requires capsid proteins to be propagated and transmitted from cell to cell. Infection of cells or an animal with the encapsidated recombinant poliovirus nucleic acids alone then results in a single round of infection without a chance for further spread. Because of this feature, the encapsidated recombinant poliovirus nucleic acids can be exploited to deliver nucleic acids to cells without risk of viral spread.

Equivalents

Those skilled in the art will recognize, or be able to ascertain using no more than routine experimentation, many equivalents to the specific embodiments of the invention described herein. Such equivalents are intended to be encompassed by the following claims.

All referenced patents and publications are hereby incorporated by reference in their entirety.

What is claimed is:

1. An encapsidated recombinant poliovirus nucleic acid which does not express proteins sufficient for encapsidation, wherein the encapsidated poliovirus nucleic acid
   is substantially free of nucleic acid which competes with the encapsidated recombinant poliovirus nucleic acid for encapsidation by proteins sufficient for encapsidation of the recombinant poliovirus nucleic acid; and
   includes a nucleotide sequence which encodes amino acids which allow for processing of a foreign protein or fragment thereof encoded by a foreign nucleotide sequence inserted in the poliovirus nucleic acid.

2. A method for encapsidating a recombinant poliovirus nucleic acid, comprising the steps of:
   providing
   a recombinant poliovirus nucleic acid which does not express proteins sufficient for encapsidation, the recombinant poliovirus nucleic acid further comprising a nucleotide sequence which encodes amino acids which allow for processing of a foreign protein or fragment thereof encoded by a foreign nucleotide sequence inserted in the poliovirus nucleic acid; and an expression vector the nucleic acid of which does not compete with the recombinant poliovirus nucleic acid for encapsidation by proteins sufficient for encapsidation of the recombinant poliovirus nucleic acid and which encodes at least a portion of a protein necessary for encapsidating the recombinant poliovirus nucleic acid and directs expression of at least a portion of a protein necessary for encapsidating the recombinant poliovirus nucleic acid; and contacting a host cell with the recombinant poliovirus nucleic acid and the expression vector under conditions appropriate for introduction of the recombinant poliovirus nucleic acid and the expression vector into the host cell; and obtaining a yield of encapsidated viruses which substantially comprises encapsidated recombinant poliovirus nucleic acid.

3. The encapsidated recombinant poliovirus nucleic acid of claim 1, which lacks the nucleotide sequence encoding at least a portion of the capsid precursor protein P1.

4. The encapsidated recombinant poliovirus nucleic acid of claim 1, which lacks the nucleotide sequence encoding at least a portion of the capsid proteins VP1 and VP2, VP1 and VP3, VP1 and VP4, VP2 and VP3, VP2 and VP4, or VP3 and VP4.

5. The encapsidated recombinant poliovirus nucleic acid of claim 1, which lacks the nucleotide sequence encoding the entire capsid precursor protein P1.

6. The encapsidated recombinant poliovirus nucleic acid of claim 1, wherein a nucleotide sequence of the encapsidated recombinant poliovirus nucleic acid which encodes at least a portion of a protein necessary for encapsidating the recombinant poliovirus nucleic acid is replaced by a foreign nucleotide sequence encoding, in an expressible form, a foreign protein or fragment thereof.

7. The encapsidated recombinant poliovirus nucleic acid of claim 1, wherein the amino acids which allow for processing of the foreign protein or fragment comprise a cleavage site for an enzyme.

8. The encapsidated recombinant poliovirus nucleic acid of claim 7, wherein the enzyme is poliovirus 2A protease.

9. The encapsidated recombinant poliovirus nucleic acid of claim 1, wherein the amino acids which allow for processing of the foreign protein or fragment comprise spacing for processing of the foreign protein or fragment thereof.

10. The encapsidated recombinant poliovirus nucleic acid of claim 6, wherein the foreign nucleotide sequence encodes a protein or fragment thereof selected from the group consisting of a viral antigen or a fragment thereof, a bacterial antigen or a fragment thereof, a tumor antigen or a fragment thereof, an immunological response modifier or a fragment thereof, and a protein with enzymatic activity or a fragment thereof.

11. The encapsidated recombinant poliovirus nucleic acid of claim 10, wherein the viral antigen or fragment thereof is selected from the group consisting of a human immunodeficiency viral antigen or a fragment thereof, a hepatitis viral antigen or a fragment thereof, an influenza viral antigen or a fragment thereof, a respiratory syncytial viral antigen or a fragment thereof, and a rotaviral antigen or a fragment thereof.

12. The encapsidated recombinant poliovirus nucleic acid of claim 11, wherein the human immunodeficiency viral antigen is selected from the group consisting of the gag protein or a fragment thereof, the pol protein or a fragment thereof, and the env protein or a fragment thereof.

13. The encapsidated recombinant poliovirus nucleic acid of claim 10, wherein the bacterial antigen or fragment thereof is selected from the group consisting of tetanus toxin or a fragment thereof, diphtheria toxin or a fragment thereof, cholera toxin or a fragment thereof, mycobacterium tuberculosis protein antigen B or a fragment thereof, and a protein from *Helicobactor pylori* or a fragment thereof.

14. The encapsidated recombinant poliovirus nucleic acid of claim 10, wherein the tumor antigen or fragment thereof is selected from the group consisting of carcinoembryonic antigen or fragment thereof, melanoma ganglioside antigen GM2 or a fragment thereof, melanoma ganglioside antigen GD2 or a fragment thereof, melanoma ganglioside antigen GD3 or a fragment thereof, antigen Jen CRG from colorectal and lung cancer cells or a fragment thereof, a synthetic peptide of immunoglobulin epitope from B cell malignancies or a fragment thereof, and an antigen which is a product of the oncogene erb, neu, or sis.

15. The encapsidated recombinant poliovirus nucleic acid of claim 10, wherein the immunological response modifier or fragment thereof is a cytokine or fragment thereof or a linear B or T cell epitope or a fragment thereof.

16. The encapsidated recombinant poliovirus nucleic acid of claim 6, wherein the foreign nucleotide sequence encodes a ribozyme.

17. The encapsidated recombinant poliovirus nucleic acid of claim 6, wherein the foreign nucleotide sequence encodes an antisense nucleic acid.

18. An immunogenic composition comprising the recombinant poliovirus nucleic acid of claim 1 and a physiologically acceptable carrier.

19. An immunogenic composition comprising the recombinant poliovirus nucleic acid of claim 6 and a physiologically acceptable carrier.

20. The method of claim 2 wherein the expression vector is introduced into the host cell prior to the introduction of the recombinant poliovirus nucleic acid.

21. The method of claim 2 wherein a nucleotide sequence of the encapsidated recombinant poliovirus nucleic acid which encodes at least a portion of a protein necessary for encapsidating the recombinant poliovirus nucleic acid is replaced by a foreign nucleotide sequence encoding, in an expressible form, a foreign protein or fragment thereof.

22. The method of claim 2 wherein the expression vector comprises a virus.

23. The method of claim 22 wherein the virus is a recombinant vaccinia virus.

24. The method of claim 2 wherein the expression vector comprises a plasmid.

25. The method of claim 2, wherein the amino acids which allow for processing of the foreign protein or fragment comprise a cleavage site for an enzyme.

26. The method of claim 25, wherein the enzyme is poliovirus 2A protease.

27. The method of claim 2, wherein the amino acids which allow for processing of the foreign protein or fragment provide spacing for processing of the foreign protein or fragment thereof.

28. The method of claim 21, wherein the foreign nucleotide sequence encodes a protein or fragment thereof selected from the group consisting of a viral antigen or a fragment thereof, a bacterial antigen or a fragment thereof, a tumor antigen or a fragment thereof, an immunological response modifier or a fragment thereof, and a protein with enzymatic activity or a fragment thereof.

29. The method of claim 28, wherein the viral antigen or fragment thereof is selected from the group consisting of a human immunodeficiency viral antigen or a fragment thereof, a hepatitis viral antigen or a fragment thereof, an influenza viral antigen or a fragment thereof, a respiratory syncytial viral antigen or a fragment thereof, and a rotaviral antigen or a fragment thereof.

30. The method of claim 29, wherein the human immunodeficiency viral antigen or fragment thereof is selected from the group consisting of the gag protein or a fragment thereof, the pol protein or a fragment thereof, and the env protein or a fragment thereof.

31. The method of claim 28, wherein the bacterial antigen or fragment thereof is selected from the group consisting of tetanus toxin or a fragment thereof, diphtheria toxin or a fragment thereof, cholera toxin or a fragment thereof, mycobacterium tuberculosis protein antigen B or a fragment thereof, and a protein from *Helicobactor pylori* or a fragment thereof.

32. The method of claim 28, wherein the tumor antigen or fragment thereof is selected from the group consisting of carcinoembryonic antigen or a fragment thereof, melanoma ganglioside antigen GM2 or a fragment thereof, melanoma ganglioside antigen GD2 or a fragment thereof, melanoma ganglioside antigen GD3 or a fragment thereof, antigen Jen CRG from colorectal and lung cancer cells or a fragment thereof, a synthetic peptide of immunoglobulin epitope from B cell malignancies or a fragment thereof, and an antigen which is a product of the oncogene erb, neu, or sis.

33. The method of claim 28, wherein the immunological response modifier or fragment thereof is a cytokine or fragment thereof or a linear B or T cell epitope or fragment thereof.

34. The method of claim 21, wherein the foreign nucleotide sequence encodes a ribozyme.

35. The method of claim 21, wherein the foreign nucleotide sequence encodes an antisense nucleic acid.

36. The method of claim 2 wherein the host cell is a mammalian host cell.

37. An encapsidated recombinant poliovirus nucleic acid produced by the method of claim 2.

* * * * *

UNITED STATES PATENT AND TRADEMARK OFFICE
CERTIFICATE OF CORRECTION

PATENT NO. : 5,817,512
DATED : October 6, 1998
INVENTOR(S) : Casey D. MORROW, et al.

It is certified that error appears in the above-identified patent and that said Letters Patent is hereby corrected as shown below:

On the title page, left column, please insert between [73] and [21] --[*] Note: The term of this patent shall not extend beyond the expiration date of the full statutory term of U.S. Patent No. 5,614,413.--

On the title page of the patent, right column, at [45], change "Oct. 6, 1998" to -- *Oct. 6, 1998--.

At column 1, line 14, delete "AI125005" and insert therefor --AI25005--.

At column 4, line 38, delete "orpol" and insert therefor --or pol--, and italicize both "gag" and "pol".

At column 76, line 20, italicize "erb".

At column 76, line 20, italicize "neu".

At column 76, line 20, italicize "sis".

At column 78, line 7, italicize "erb".

At column 78, line 7, italicize "neu".

UNITED STATES PATENT AND TRADEMARK OFFICE
CERTIFICATE OF CORRECTION

PATENT NO. : 5,817,512
DATED : October 6, 1998
INVENTOR(S) : Casey D. MORROW, et al.

It is certified that error appears in the above-identified patent and that said Letters Patent is hereby corrected as shown below:

At column 78, line 7, italicize "sis".

Signed and Sealed this

Twentieth Day of April, 1999

Q. TODD DICKINSON

*Attest:*

*Attesting Officer*    *Acting Commissioner of Patents and Trademarks*